(12) United States Patent
Kim et al.

(10) Patent No.: US 11,573,019 B2
(45) Date of Patent: Feb. 7, 2023

(54) INDOOR UNIT FOR AIR CONDITIONER

(71) Applicant: LG ELECTRONICS INC., Seoul (KR)

(72) Inventors: Yongnam Kim, Seoul (KR); Sunggyu Choi, Seoul (KR); Sehwan Bae, Seoul (KR); Junseok Bae, Seoul (KR); Kyunam Lee, Seoul (KR); Ilseop So, Seoul (KR); Sangyoon Lee, Seoul (KR); Hyesun Lee, Seoul (KR); Hosik Jang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 870 days.

(21) Appl. No.: 16/391,058

(22) Filed: Apr. 22, 2019

(65) Prior Publication Data

US 2019/0321769 A1    Oct. 24, 2019

(30) Foreign Application Priority Data

Apr. 23, 2018  (KR) .......................... 10-2018-0046796
Feb. 14, 2019  (KR) .......................... 10-2019-0017447

(51) Int. Cl.
*B01D 46/42* (2006.01)
*B03C 3/011* (2006.01)
(Continued)

(52) U.S. Cl.
CPC ................. *F24F 8/30* (2021.01); *A61L 9/18* (2013.01); *A61L 9/22* (2013.01); *B01D 46/0032* (2013.01);
(Continued)

(58) Field of Classification Search
CPC ........ F24F 3/1603; F24F 13/28; F24F 1/0007; F24F 2011/0064; F24F 1/38; F24F 1/48;
(Continued)

(56) References Cited

U.S. PATENT DOCUMENTS 5,958,114 A    9/1999  Sunahara et al.
7,596,960 B2  10/2009  Bae
(Continued)

FOREIGN PATENT DOCUMENTS

CN    1183533 A    6/1998
CN    1603696 A    4/2005
(Continued)

*Primary Examiner* — Minh Chau T Pham
(74) *Attorney, Agent, or Firm* — Dentons US LLP

(57) ABSTRACT

An indoor unit for an air conditioner including: a cabinet assembly forming an external appearance of the indoor unit and having a suction port formed in a rear surface of the cabinet; a filter module movably disposed in rear of the cabinet assembly; a filter module mounted to the filter mounting member and filtering foreign substances in air flowing into the suction port; a mobile member connected to the filter mounting member and moving a position of the filter mounting member; a driving device pressing the mobile member to change the position of the filter mounting member; and a controller configured to, in response to receiving a control command to change the position of the filter mounting member, operate the driving device that presses the mobile member.

20 Claims, 36 Drawing Sheets

(51) Int. Cl.
*B03C 3/019* (2006.01)
*F24F 1/0073* (2019.01)
*F24F 13/28* (2006.01)
*F24F 8/30* (2021.01)
*B01D 46/00* (2022.01)
*B03C 3/04* (2006.01)
*B01D 53/88* (2006.01)
*B01D 53/86* (2006.01)
*A61L 9/22* (2006.01)
*A61L 9/18* (2006.01)
*F24F 8/108* (2021.01)
*F24F 8/167* (2021.01)

(52) U.S. Cl.
CPC ..... *B01D 46/0038* (2013.01); *B01D 46/4227* (2013.01); *B01D 53/8678* (2013.01); *B01D 53/885* (2013.01); *B03C 3/011* (2013.01); *B03C 3/019* (2013.01); *B03C 3/04* (2013.01); *F24F 1/0073* (2019.02); *F24F 8/108* (2021.01); *F24F 8/167* (2021.01); *F24F 13/28* (2013.01); *A61L 2209/111* (2013.01); *A61L 2209/14* (2013.01); *A61L 2209/15* (2013.01); *B01D 2255/702* (2013.01); *B01D 2255/802* (2013.01); *B01D 2257/90* (2013.01); *B01D 2258/06* (2013.01); *B01D 2279/50* (2013.01)

(58) Field of Classification Search
CPC ... F24F 1/56; B01D 46/0023; B01D 46/0028; B01D 46/003; B01D 46/0032; F25B 31/006; F25D 23/003; B05B 3/105; F04D 29/326
USPC ........ 55/385.2; 96/66, 77, 82; 210/106, 225; 62/181, 272, 259.1, 277, 419, 426, 507; 165/59; 415/208.1
See application file for complete search history.

(56) References Cited

U.S. PATENT DOCUMENTS

| | | | |
|---|---|---|---|
| 8,631,664 B2 * | 1/2014 | Shibuya | F24F 1/0073 62/317 |
| 8,951,319 B2 | 2/2015 | Kim et al. | |
| 2005/0076671 A1 | 4/2005 | Bae | |
| 2010/0192768 A1 | 8/2010 | Kim et al. | |
| 2015/0224516 A1 * | 8/2015 | Tanaka | B03C 3/88 96/24 |
| 2017/0328590 A1 * | 11/2017 | Ke | B01D 46/46 |
| 2017/0363306 A1 * | 12/2017 | Cur | F24F 8/10 |
| 2019/0381435 A1 * | 12/2019 | Heilig | B01D 46/04 |
| 2021/0356168 A1 * | 11/2021 | Lu | B01D 46/44 |

FOREIGN PATENT DOCUMENTS

| | | |
|---|---|---|
| CN | 1605804 A | 4/2005 |
| CN | 1654888 A | 8/2005 |
| CN | 1740683 A | 3/2006 |
| CN | 101122404 A | 2/2008 |
| CN | 101476756 A | 7/2009 |
| CN | 101578485 A | 11/2009 |
| CN | 201448942 U | 5/2010 |
| CN | 101808711 A | 8/2010 |
| CN | 102345926 A | 2/2012 |
| CN | 103080664 A | 5/2013 |
| CN | 203310006 U | 11/2013 |
| CN | 105698360 A | 6/2016 |
| CN | 205351497 U | 6/2016 |
| CN | 105765317 A | 7/2016 |
| CN | 205448204 U | 8/2016 |
| CN | 105953361 A | 9/2016 |
| CN | 106413847 A | 2/2017 |
| CN | 206291324 U | 6/2017 |
| CN | 206724349 U | 12/2017 |
| CN | 207146667 U | 3/2018 |
| JP | 10110966 A | 4/1998 |
| JP | 2005-106457 A | 4/2005 |
| KR | 1020100036919 A | 4/2010 |

* cited by examiner

INDOOR UNIT FOR AIR CONDITIONER

CROSS-REFERENCE TO RELATED APPLICATIONS

This application claims the priority benefit of Korean Patent Application No. 10-2018-0046796, filed on Apr. 23, 2018, and 10-2019-0017447, filed on Feb. 14, 2019 in the Korean Intellectual Property Office, the disclosure of which are incorporated herein by reference.

BACKGROUND OF THE INVENTION

1. Field of the Invention

The present invention relates to an indoor unit for an air conditioner, and more particularly to a filter installed in the indoor unit.

2. Description of the Related Art

An indoor unit for an air conditioner may adjust required indoor temperature by discharging air heat-exchanged with a refrigerant to an indoor space. The indoor unit for the air conditioner suctions indoor air through an suction port, make the suctioned air to exchange heat with a refrigerant, and discharge the heat-exchanged air to an discharge port.

An indoor unit for the air conditioner may be divided into a ceiling-mounted type, a wall-mounted type, and a stand-alone type. In a standalone indoor unit, an outlet may be formed at the front side or either side (right or left) of a cabinet, and an suction port may be formed at the rear side of the cabinet.

Since the stand-alone indoor unit is disposed with an outlet facing an indoor space, an outlet disposed at the rear side of cabinet is disposed to face a wall surface or an edge of the indoor space. Therefore, even a filter disposed at the suction port to filter foreign substances may be disposed at a rear surface of the cabinet.

It is difficult to change an installation position of the stand-alone indoor unit due to size and/or weight of the product or arrangement of a refrigerant tube. Thus, a user should separate or install the filter from the back of the cabinet. This may cause inconvenience to the user due to limitation in a space where the air suction unit is installed.

Korean Patent Application Publication No. 10-2017-0076015 discloses a conventional structure in which a suction port is formed in the rear and a filter member disposed at the suction port is mounted to an installation bracket. The structure has the filter member disposed at the rear side where the suction port is formed, and the filter member is inserted into or drawn from a detachment hole formed in a lateral direction of the installation bracket.

This structure requires a user to be positioned at a rear side of the indoor unit when inserting the filter member into a case of the indoor unit or drawing the filter member therefrom. In addition, this structure has a limitation in terms of installation in that a separate space is needed to draw the filter member from a side surface of the indoor unit.

Multiple types of filters can be installed at a suction port to improve cleanness of an indoor space, remove fine dust, or remove odor. Such filters should be installed or detached at a rear side of a cabinet where the suction port is formed. There is a spatial limitation in forming a suction port, and thus, multiple structures should be coupled to install multiple types of filters, which requires more complicated operations.

SUMMARY OF THE INVENTION

The present disclosure solves the above-mentioned problems. One object of the present invention is to provide an indoor unit in which a filter is capable of being easily mounted to a suction port formed in rear of the indoor unit.

Another object of the present invention is to provide an indoor unit in which a suction port and a filter are installed in different areas.

Yet another object of the present invention is to provide an indoor unit in which a plurality of filters is capable of being easily mounted at a suction port formed in rear of the indoor unit.

Yet another object of the present invention is to provide an indoor unit in which a plurality of filters are capable of being easily managed and stably mounted.

Still yet another object of the present invention is to provide an indoor unit that minimizes a thickness of a filter module mounted in rear of the indoor unit and performing a plurality of filter functions.

Objects of the present invention are not limited to the aforementioned objects, and other objects not mentioned in the above may be clearly comprehended to those of ordinary skill in the art to which the embodiment pertains through the following description.

To achieve the aforementioned objects, an indoor unit for an air conditioner according to the present invention may be configured such that a suction port is formed on a rear surface, a filter module disposed at the suction port is mounted to a filter mounting member, the position of the filter mounting member is changed by a mobile member, and arrangement of a filter module mounted to the filter mounting member is changed in response to a force applied by a driving device to the mobile member, so that the filter mounting member with the filter module mounted thereto may move to an area other than the suction port.

In addition, when a control command is received via a controller to change the position of the filter mounting member, the driving device may be operated to change the position of the filter module, so that the position of the filter module may be moved to an area of the suction port or an area other than the suction port in accordance to a specific signal.

The indoor unit for the air conditioner according to the present invention may further include an input unit configured to receive a control command form a user, and, when the input unit receives the control command from the user to change the position of the filter mounting member, the driving device pressing the mobile member, so that the filter module mounting member with the filter module mounted thereto may move to an area other than the suction port in accordance to the control command from the user.

The mobile member may position the filter mounting member such that the filter module covers the suction port, or such that a direction of drawing the filter module faces forward. Accordingly, the filter module, disposed at the suction port formed on the rear surface, may be inserted or drawn from an area in front of the cabinet assembly.

The filter module may be inserted into or drawn from the filter mounting member in a lateral direction of the filter module, and the filter mounting member may move between a first position and a second position, the first position at which the filter module is positioned at the suction port, and the second position at which the filter module is positioned with the lateral direction of the filter module facing forward. Accordingly, the filter module, disposed at the suction port formed on the rear surface, may be inserted or drawn from an area in front of the cabinet assembly.

The mobile member may include: dual links having different length, and rotatably connected to the cabinet assembly and the filter mounting member, respectively; and drive transmission links transferring forces generated by the driving device to the dual links. Accordingly, the filter mounting member, disposed on a rear side of the cabinet assembly, may be moved to a lateral side of the cabinet assembly.

The dual links may include: a first link rotatably connected to the cabinet assembly and the filter mounting member, respectively; and a second link spaced apart from the first link and rotatably connected to the cabinet assembly and the filter mounting member, respectively, and a length of the first link may be longer than a length of the second link. Accordingly, the filter mounting member, disposed on a rear side of the cabinet assembly, may be moved to a lateral side of the cabinet assembly.

A gap between one end of the first link connected to the filter mounting member and one end of the second link connected to the filter mounting member may be longer than a gap between the other end of the first link connected to the cabinet assembly and the other end of the second link connected to the cabinet assembly. Accordingly, the filter mounting member, disposed on a rear side of the cabinet assembly, may be moved to a lateral side of the cabinet assembly.

The second link may be disposed closer to a lateral side of the cabinet assembly than the first link is, and the first link may be disposed closer to the driving device than the second link is. Accordingly, the filter mounting member, disposed on a rear side of the cabinet assembly, may be moved to a lateral side of the cabinet assembly.

The drive transmission links may include: a motor link fixedly connected to the driving device; and a bending link having one end rotatably connected to the motor link and the other end rotatably connected to the first link. Accordingly, positions of the dual links may be changed.

The bending link may include a bending portion vertically bent between one end and the other end, and the bending portion may be disposed closer to one end of the bending link being connected to the motor link than the other end of the bending link being connected to the first link. Accordingly, the dual links may be moved to an outer side of the cabinet assembly.

The filter mounting member may include: a filter module mounting part forming a space where to install the filter module, and being open rearward; and a mobile member fastening part disposed above or below the filter module mounting part, forming a space where the mobile member is disposed, and being open forward. Accordingly, a space where the filter module is disposed may be separated from a space where the mobile member is disposed.

The cabinet assembly may further include a rearward protruding member that protrudes rearward, and the filter mounting member is in close contact with the rear protruding member when the filter module is positioned at the suction port.

The rearward protruding member includes: a filter module recognition sensor that protrudes in a direction in which the filter mounting member is mounted so that the filter module recognition sensor is pressed by the filter module, and the filter mounting member includes: a filter module recognition hole that is penetrated by the filter module recognition sensor when the filter mounting member is in close contact with the rearward protruding member. Accordingly, it is possible to recognize mounting of the filter module when the filter mounting member with the filter module mounted thereto is disposed at a side of the suction port of the cabinet assembly.

The rearward protruding member may include an ionization part having an electrode that ionizes molecules in air flowing into the suction port, and the electrode may be disposed to protrude rearward vertically to a rear surface on which the suction port is formed, so that the air flowing into the suction port are ionized in a large area. The filter module may include: a pre-filter configured to filter large-sized dust in the air flowing into the suction port; a dust collecting filter unit configured to collect air particles, ionized by the ionization part, to filter the air; a deodorization filter unit configured to remove odor from the air flowing into the suction port; and a filter case with the pre-filter being fixed thereto and the dust collecting filter unit and the deodorization filter unit being mounted thereto. Accordingly, a plurality of filters may be disposed while coupled to each other.

A power terminal configured to supply a voltage to the dust collecting filter unit, and a ground terminal configured to provide a ground to the dust collecting filter unit may be formed in the rearward protruding member in a direction in which the filter mounting member is mounted. A power terminal hole penetrated by the power terminal in response to the filter mounting member being in close contact with the rearward protruding member, and a ground terminal hole penetrated by the ground terminal in response to the filter mounting member being in close contact with the rearward protruding member may be formed in the filter mounting member. A ground receiving terminal configured to provide a ground to the dust collecting filter unit in response to contact with the ground terminal, and a power receiving terminal configured to supply power to the dust collecting filter unit in response to contact with the power terminal may be formed in the dust collecting filter unit. Accordingly, the dust collecting filter part may be operated when the filter mounting member with the filter module mounted thereto is mounted to the cabinet assembly.

Details of other embodiments are included in the following description and the accompanying drawings.

According to an indoor unit of an air conditioner of the present invention, there are one or more effects as described below.

The above solutions have advantages in that a filter module is capable of being easily mounted and separated because a filter mounting member to be mounted with the filter module and a mobile member for changing a position of the filter mounting member are included.

The filter mounting member has a structure to be moved by the mobile member, and thus, there is an advantage in that a user is capable of mounting the filter module to the filter mounting member at a position easily approached because a position of the filter module to be mounted to the filter mounting member and a position of a suction port is disposed are different.

The mobile member has dual links having different lengths and spaced apart from each other, and the filter module is disposed to be drawn in a forward direction from an outer side of a cabinet, and thus, there is an advantage in that the filter module is capable of being easily mounted and separated.

A plurality of filters is mounted to the filter mounting member disposed to be easily approached by a user, and the filter mounting member is positioned in rear of the suction port, and thus, there is an advantage in that bothersome operation required to mount the plurality of filters is not necessary.

The plurality of filters may maintain a state of being coupled to one another with protrusions thereof using magnetic members, and thus, there is an advantage in that the filter module is capable of being managed and used stably.

Specifically, as a filter case has a protrusion on one side to fix the plurality of filters, and a magnetic member on the other side to fix the plurality of filters, there is an advantage in that the plurality of filters is capable of being easily coupled to and separated from each other.

An electric charge unit for ionizing molecules in air collected by a dust collecting device in the filter member is additionally installed in a cabinet, and an additional electric charge unit is not included in a dust collecting filter unit in the filter module, and thus, there is an advantage in that the filter module has a slim shape.

Effects of the present invention may not be limited to the above and other objects and other objects which are not described may be clearly comprehended to those of skill in the art to which the embodiment pertains through the following description.

BRIEF DESCRIPTION OF THE DRAWINGS

The accompanying drawings constitute a part of this specification and illustrate an embodiment of the present disclosure and together with the specification, explain the present disclosure.

DETAILED DESCRIPTION OF THE PREFERRED EMBODIMENTS

Figure 1A:
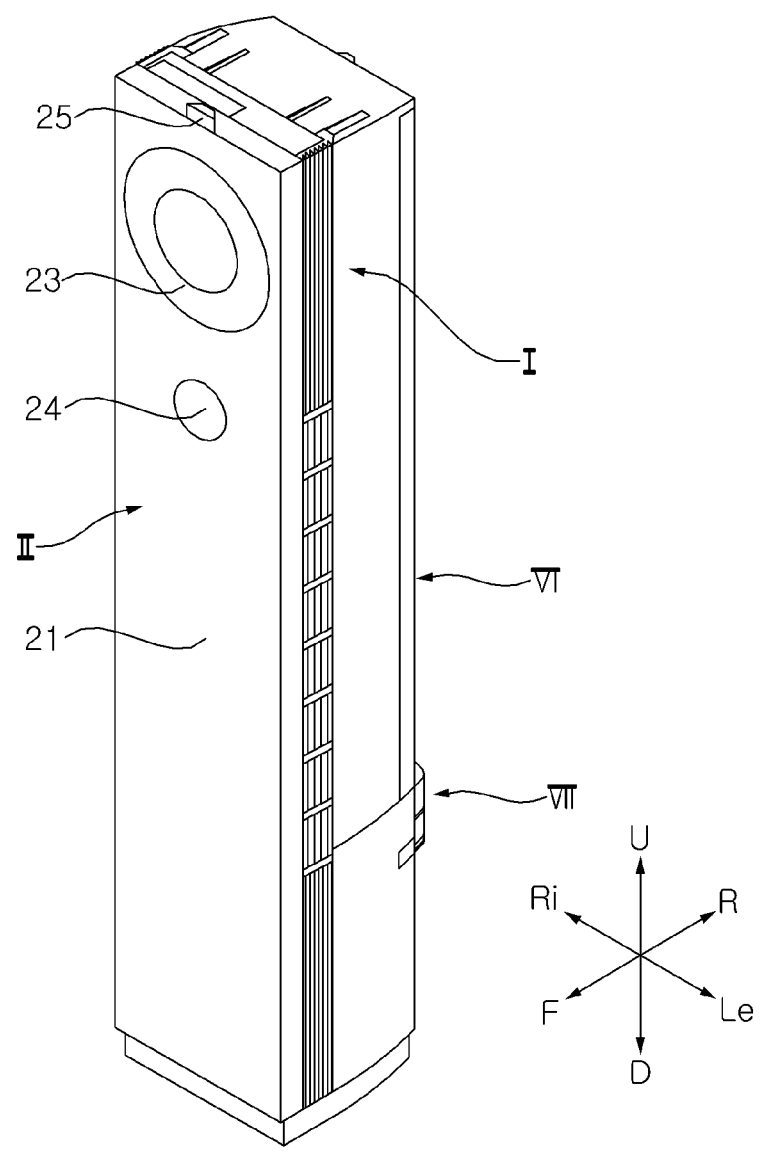
FIG. 1A is a front perspective view of an indoor unit according to an embodiment of the present invention.
Figure 1B:
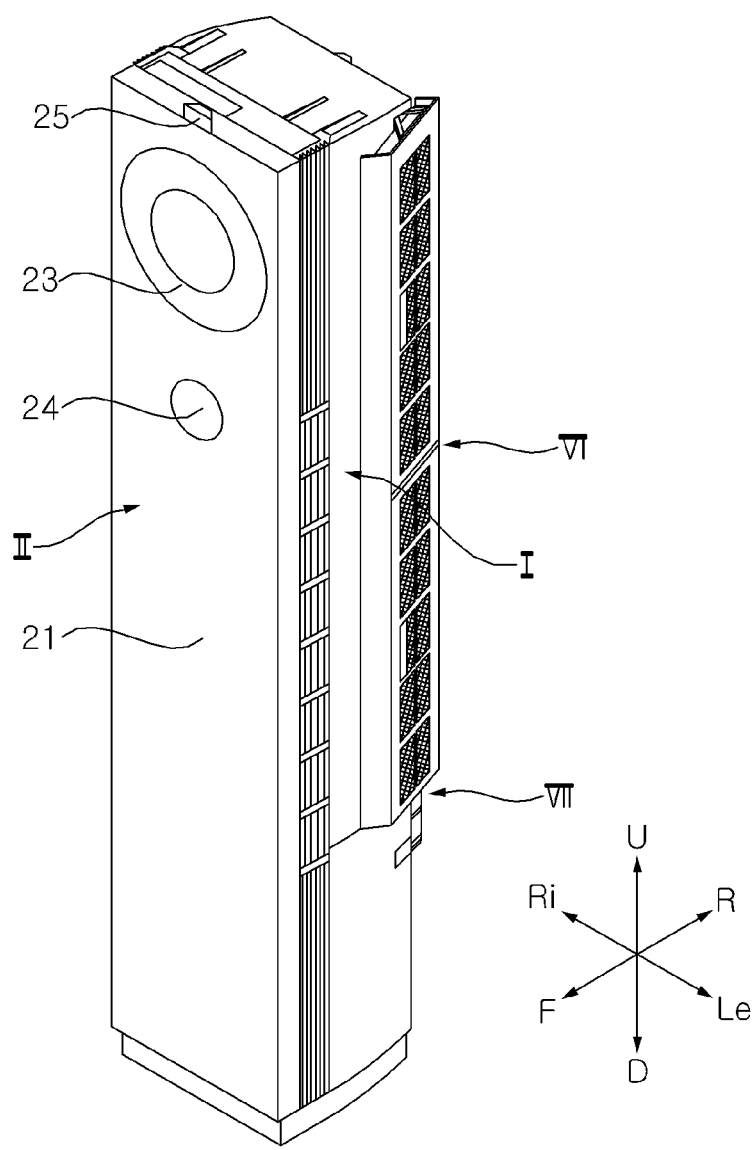
FIG. 1B is a front perspective view of an indoor unit with a filter assembly moved according to an embodiment of the present invention.
Figure 2:
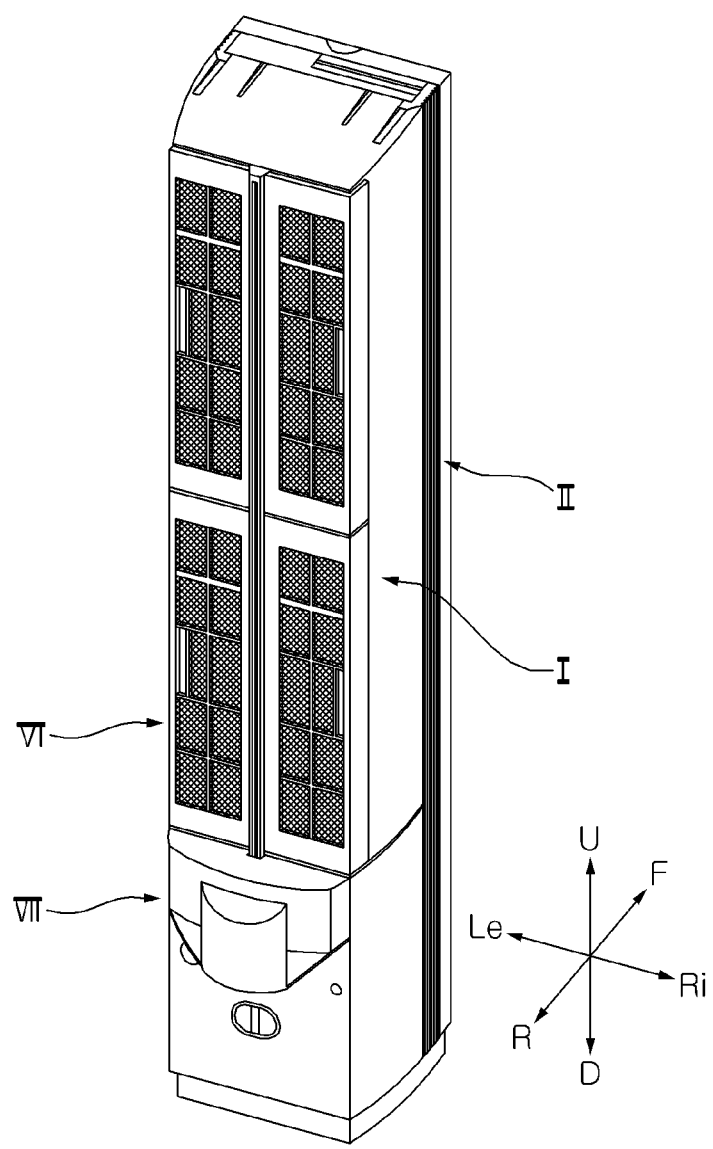
FIG. 2 is a rear perspective view of an indoor unit according to an embodiment of the present invention.
Figure 3:
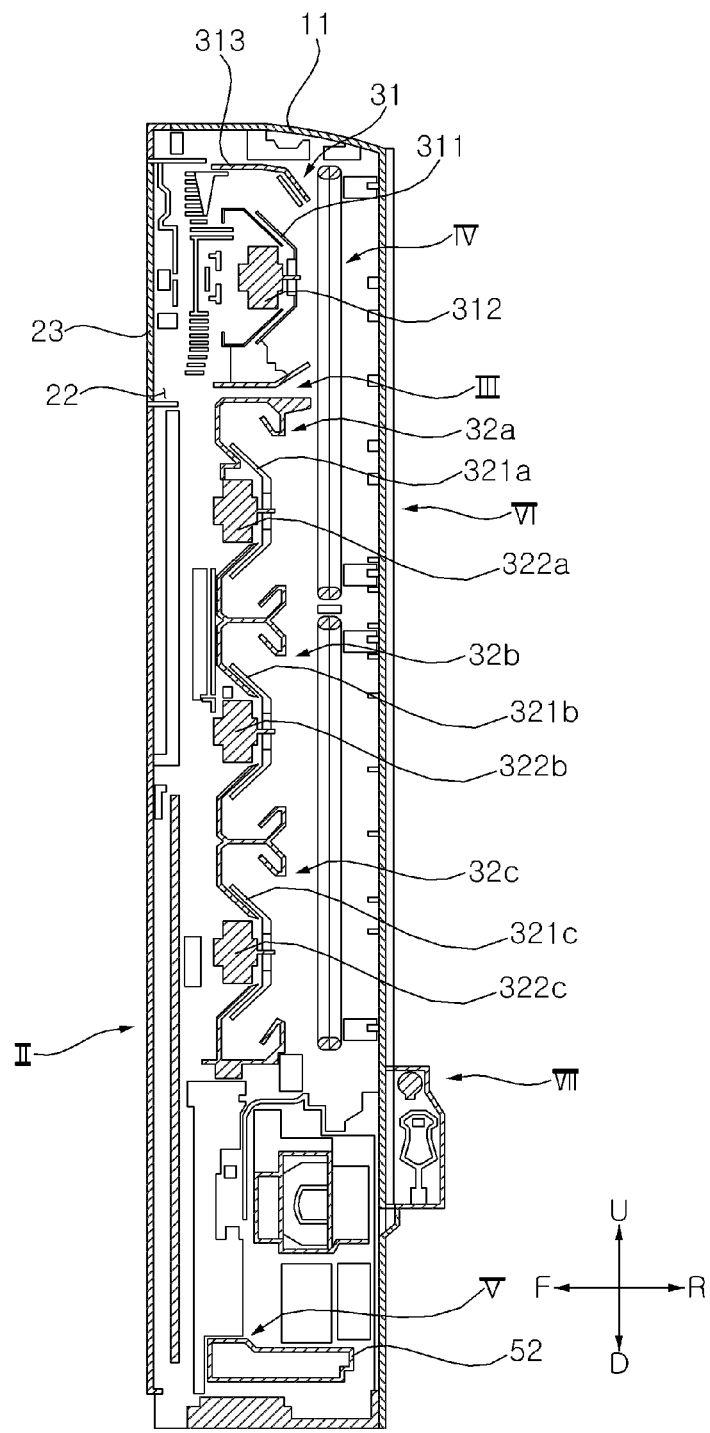
FIG. 3 is a side cross-sectional view of an indoor unit according to an embodiment of the present invention.
Figure 4:
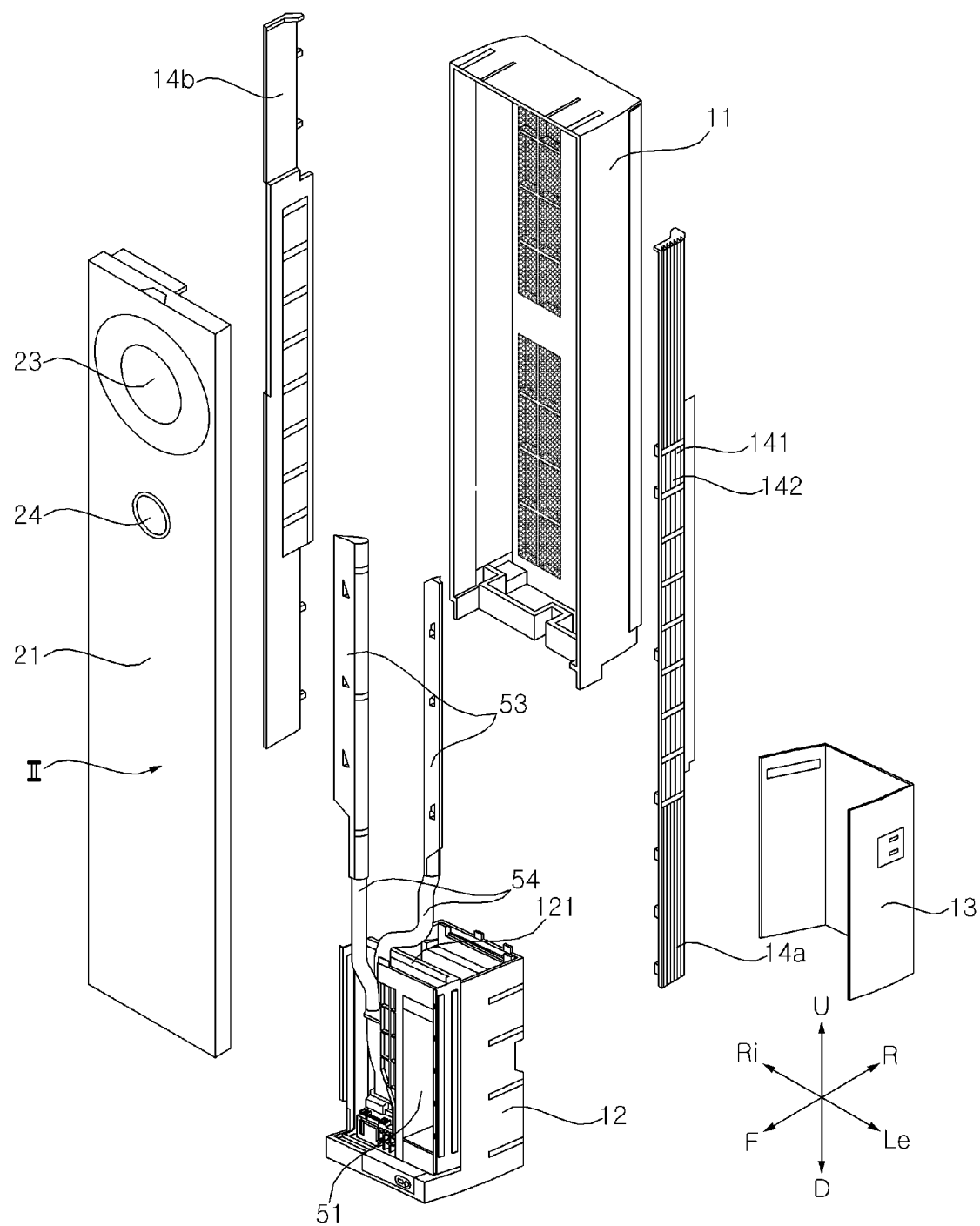
FIG. 4 is an exploded perspective view of a cabinet assembly and a door assembly according to an embodiment of the present invention.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to a person skilled in the relevant art and having possession of this disclosure, are to be considered within the scope of the invention.

As used herein, the terms "first," "second," etc. are used only to avoid confusion between components, and do not indicate the sequence or importance of the components. The directions of "upward (U)", "downward (D)", "leftward (Le)", "rightward (Ri)", "forward (F)", and "rearward (R)" in drawings are used for convenience of explanation but do not limit the scope of the present invention. Thus, the aforementioned directions may be differently defined.

As used herein, various singular forms "a," "an" and "the" are intended to include various plural forms as well, unless context clearly indicates otherwise. For example, a term "a" or "an" shall mean "one or more," even though a phrase "one or more" is also used herein. Use of the optional plural "(s)," "(es)," "(ies)" means that one or more of the indicated feature is present.

As used herein, a term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, features described with respect to certain embodiments may be combined in or with various other embodiments in any permutational or combinatory manner. Different aspects or elements of example embodiments, as disclosed herein, may be combined in a similar manner.

Various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

Hereinafter, an indoor unit for an air conditioner according to embodiments of the present invention will be described with reference to the accompanying drawings.

First, referring to FIGS. 1 to 4, all assembly structures of an air conditioner according to an embodiment will be described schematically, and each assembly structure will be described schematically.

<Overall Configuration>

An indoor unit for an air conditioner according to an embodiment may include at least the following structure: a cabinet assembly I defining an external appearance of the indoor unit and having an open front surface, a door assembly II covering the open front surface of the cabinet assembly I, a blower assembly III disposed within the cabinet assembly I to generate airflow; a heat exchange assembly IV exchanging heat of air flowing by the blower assembly III with a refrigerant, a filter assembly VI filtering air introduced into the cabinet assembly I, a filter cleaning assembly VII removing foreign substances existing on one side surface of the filter assembly VI, and a humidifying assembly V discharging humidified air to the outside of the cabinet assembly I.

<Cabinet Assembly>

The cabinet assembly I according to the present embodiment may include an upper cabinet 11 having a suction port 1143 formed on a rear surface thereof and forming a space where a heat exchanger 41 is installed, a base unit 12 disposed below the upper cabinet 11 and forming a space where at least some elements of the humidifying assembly V are disposed, a lower cabinet 13 covering the rear side and lateral sides of the base unit 12, and side discharge members 14a and 14b disposed between the upper cabinet 11 and the door assembly II and forming a side discharge port 141 through which air is discharged.

At a portion where the suction port 1143 is formed on the rear surface of the upper cabinet 11, the filter assembly VI is mounted. On the open front surface of the upper cabinet 11, the door assembly II is disposed. The upper cabinet 11 is disposed over the lower cabinet 13 and the base unit 12. The upper cabinet 11 is disposed behind the door assembly II such that it is covered by the door assembly II.

The upper cabinet 11 may form a space where the heat exchanger 41, and a blowing module 31, 32a, 32b, and 32c are disposed. Within the upper cabinet 11, a heat exchanger mounting member (not shown) to which the heat exchanger 41 is mounted, a front blowing module mounting member (not shown) to which the front blowing module 31 is mounted, and a lateral blowing module mounting member (not shown) to which the lateral blowing modules 32a, 32b, and 32c are mounted may be disposed.

The upper cabinet 11 may be disposed in rear of the side discharge members 14a and 14b relative to the door assembly II. The upper cabinet 11 may be disposed over the base unit 12.

Detailed configuration and arrangement of the upper cabinet 11 will be described in the following.

The base unit 12 may be disposed below the upper cabinet 11. The base unit 12 may form a space in which elements of the humidifying assembly V, such as a water tank 51, a heater 52, etc., are disposed. A power line tension maintaining part (not shown) wound around by a power line (not shown) connected to the filter cleaning assembly VII may be disposed within the base unit 12.

The base unit 12 may be shaped like a box having an open front surface. The lower cabinet 13 and part of the side discharge members 14a and 14b may be disposed on an outer circumference of the base unit 12. A power line through-hole which is penetrated by the power line connected to the filter cleaning assembly VII, and a humidifying tube through hole (hot shown) which is penetrated by a humidifying tube 54 the humidifying assembly V may be formed in the base unit 12. The door assembly II may be disposed on the front surface of the base unit 12. The upper cabinet 11 may be mounted to an upper side of the base unit 12. On the upper side of the base unit 12, an separate support member 121 for supporting a structure disposed on the upper side of the base unit 12 may be further mounted.

The base unit 12 and the upper cabinet 11 are disposed vertically and coupled to each other, and the door assembly II is disposed on the front surfaces of the base unit 12 and the upper cabinet 11.

The lower cabinet 13 may cover the lateral surfaces and the rear surface of the base unit 12. Since the lower cabinet 13 is disposed external to the base unit 12, the lower cabinet 13 may also function as a reinforcement structure for the base unit 12. A lower plate (not shown) for limiting downward movement of the filter cleaning assembly VII may be disposed on a rear surface of the lower cabinet 13. A guide rail 116 for guiding movement of the filter cleaning assembly VII may be disposed on the rear surface of the lower cabinet 13. A refrigerant tub hole (not shown) penetrated by a refrigerant tube (not shown) of the heat exchange assembly IV may be formed in the rear surface of the lower cabinet 13. A power line hole (not shown) penetrated by a power line (not shown) supplying power from an external power source may be formed in the rear surface of the lower cabinet 13.

The side discharge members 14a and 14b may be disposed between the upper cabinet 11 and the door assembly II. The side discharge members 14a and 14b may be disposed between the lower cabinet 13 and the door assembly II. The side discharge members 14a and 14b may cover a portion of side surfaces of the indoor unit for the air conditioner.

The side discharge port 141 for discharging air flowing by the lateral blowing modules 32a, 32b, and 32c described below may be formed on both side surfaces of the side discharge members 14a and 14b. A plurality of vanes 142 guiding a direction of air to be discharged may be disposed at the side discharge port 141. The plurality of vanes may be integrally formed with the side discharge members 14a and 14b. The plurality of vanes according to the present embodiment may be inclined in a forward direction, enabled to guide air discharged to the outside of the cabinet to flow in the forward direction.

<Door Assembly>

The door assembly II may include a door plate 21 covering the front surface of the indoor unit and having a front discharge port 22 at one side thereof, a door moving member (not shown) moving the door plate 21 in a horizontal direction, a discharge port cover 23 opening and closing the front discharge port 22 formed in the door plate 21, and a cover moving member (not shown) moving the front discharge port cover 23 in a vertical direction.

The door moving member according to the present embodiment is capable of moving the door plate 21 in the horizontal direction in the front of the cabinet assembly I. The cover moving member according to the present embodiment may move the discharge port cover 23 to open or close the front discharge port 22 by moving the discharge port cover 23. The cover moving member may move the discharge port cover 23 in a direction downward of the front discharge port 22. When the front discharge port 22 is opened by the movement of the discharge port cover 23, the front blowing module 31 described below may be exposed to an outside. The front blowing module 31 may move in a forward-backward direction of the front discharge port 22 which is open.

The door assembly II may further include a display unit 24 to display an operation state of the indoor unit or receive a user's command, and a camera sensor 25 to sense a condition of an indoor space. For example, the condition of the indoor space may include, among other conditions, a size of the indoor space, the number of people existing in the indoor space, and a position of a person in the indoor space.

The display unit 24 according to the present embodiment may be disposed below the front discharge port 22. The camera sensor 25 according to the present embodiment may be disposed in the upper side of the door plate 21.

<Blower Assembly>

A blower assembly III may include a front blowing module 31 discharging air in a direction forward of the indoor unit, and lateral blowing modules 32a, 32b, or 32c discharging air in directions from both side surfaces of the indoor unit. The blowing assembly III according to the present embodiment may include one front blowing module 31 and three lateral blowing modules 32a, 32b, and 32c. The front blowing module 31 and the lateral blowing modules 32a, 32b, and 32c may be disposed in front of the heat exchange assembly IV.

The front blowing module 31 may be disposed above the lateral blowing modules 32a, 32b, and 32c. The front blowing module 31 discharges air toward a front discharge port 22 that is formed in a door plate 21.

The front blowing module 31 according to the present embodiment may be configured such that a direction which the discharge port faces is capable of rotating upward, downward, leftward, rightward, or diagonally. Thus, while the discharge port of the front blowing module 31 is disposed in front of the front discharge port 22, the front blowing module 31 may adjust an air discharging direction in a manner in which an air discharging portion rotates upward, downward, leftward, rightward, or diagonally.

The front blowing module 31 may include a front blowing fan 311, a front blowing motor 312, and a front blowing fan housing 313. The front blowing module 31 according to the present embodiment is a structure of the front blowing fan 311 and the front blowing housing 313, and air discharged therefrom may reach a far distance forward.

The lateral blowing module 32a, 32b, and 32c may be disposed below the front blowing module 31. The lateral blowing module 32a, 32b, and 32c according to the present embodiment may be vertically provided in plural. Each of the plurality of the lateral blowing modules 32a, 32b, and 32c may discharge air through a side discharge port 141. The plurality of lateral blowing modules 32a, 32b, and 32c may respectively include a lateral blowing fan 321a, 321b, and 321c, lateral blowing motors 322a, 322b, and 322c, and lateral blowing guides.

The lateral blowing module 32a, 32b, and 32c may be disposed in front of the heat exchanger 41, and discharge heat-exchanged air toward the side discharge port 141. Air flowing by the lateral blowing module 32a, 32b, and 32c may flow along the vanes 142 disposed in the side discharge port 141.

<Heat Exchange Assembly>

A heat exchange assembly IV exchanges heat of indoor air, suctioned into an upper cabinet 11, with a refrigerant. The heat exchange assembly IV may include a heat exchanger 41 in which the refrigerant to exchange heat with the indoor air flows, and a refrigerant tube (not shown) forming a refrigerant flow path along which the refrigerant is introduced into or exhausted from the heat exchanger 41.

The refrigerant tube may include a refrigerant inflow tube (not shown) in which a refrigerant introduced into the heat exchanger 41 flows, and a refrigerant exhaust tube (not shown) in which a refrigerant exhausted from the heat exchanger 41 flows.

The heat exchanger 41 may be disposed at a rear side of a blower assembly III. The heat exchange 41 may be disposed between an suction port 1143 and an discharge port to allowing air flowing in the indoor unit to be heat-exchanged. The heat exchanger 41 may be disposed between a filter assembly VI and the blower assembly III. The heat exchanger 41 may have a length corresponding to a height by which the plurality of lateral blowing modules 32a, 32b, and 32c and the front blowing module 31 are disposed vertically.

The heat exchanger 41 may be disposed within the upper cabinet 11. The heat exchanger 41 may be fastened to a heat exchanger mount member 1123 formed in the upper cabinet 11.

<Humidifying Assembly>

A humidifying assembly V may discharge humidified air to the outside of the indoor unit. The humidifying assembly V may include, among other components, a water tank 51 to contain water, a heating unit 52 to receive the water from the water tank 51 and heat the water, a humidifying discharge nozzle 53 in which a humidifying discharge port (not shown) for discharging heated humidified air is formed, and a humidifying flow path 54 to guide humidified air, heated by the heating unit 52, toward the humidifying discharge nozzle 53.

The water tank 51 and the heating unit 52 may be disposed in an inner space of the base unit 12. The humidifying discharge nozzle 53, which is formed at an end portion of the humidifying flow tube 54, may be disposed at a portion at which a side discharge port 141 is formed. Thus, humidified air discharged along the humidifying discharge port may be discharged to the outside of the indoor unit by lateral blowing modules 32a, 32b, and 32c together with air flowing toward the side discharge port 141.

The humidifying flow path 52 may allow humid air, heated by the heating unit 52 disposed within the base unit 12, to flow toward the humidifying discharge port. The humidifying flow path 54 may connect the heating unit 52, which is disposed within the base unit 12, and the humidifying discharge port, which is formed at the side discharge port 141 at a height at which the upper cabinet 11 is positioned.

<Filter Cleaning Assembly>

A filter cleaning assembly VII may be movably disposed at a rear side of a filter assembly VI to move dust existing on an outer side of the filter assembly VI. The filter cleaning assembly VII may move vertically (upward and downward) along a guide rail 116 disposed in rear of the upper cabinet 11.

The filter cleaning assembly VII may move vertically (upward and downward) along the guide rail 116, separate dust existing on the outer side of the filter assembly VI, and suction the separated dust, thereby removing dust existing in filter modules 62a, 62b, 62c, and 62d.

The filter cleaning assembly may include, among other components: a filter cleaner 71 moving along the guide rail 116 to remove dust existing in the filter modules 62a, 62b, 62c, and 62d; and a power supply device (not shown) connected to the filter cleaner 71 via a power line (not shown) to supply power to the filter cleaner 71.

Thus, in the guide rail 116, there may be formed a guide groove 116a where the power line is disposed in an upward and downward direction in which the filter cleaner 71 moves.

Hereinafter, the structure of an upper cabinet and the structure of a filter assembly according to the present embodiment will be described with reference to FIGS. 5 to 35.

<Filter Assembly>

Figure 5:
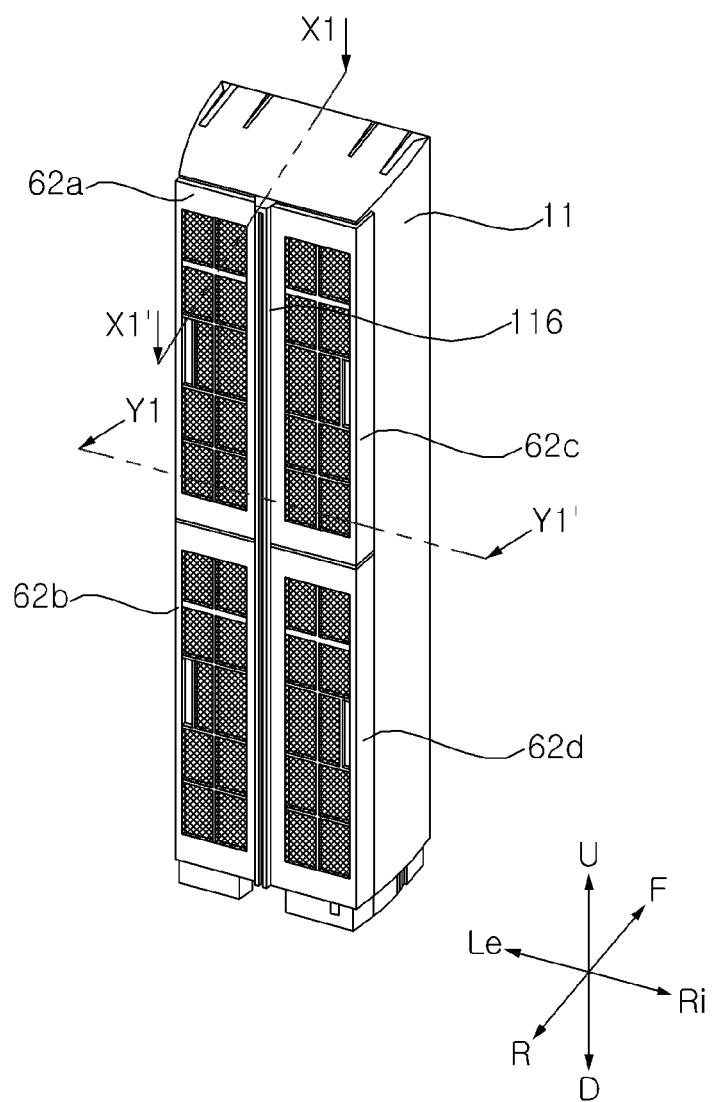
FIG. 5 is a rear perspective view of an upper cabinet and a filter assembly according to an embodiment of the present invention.
Figure 6:
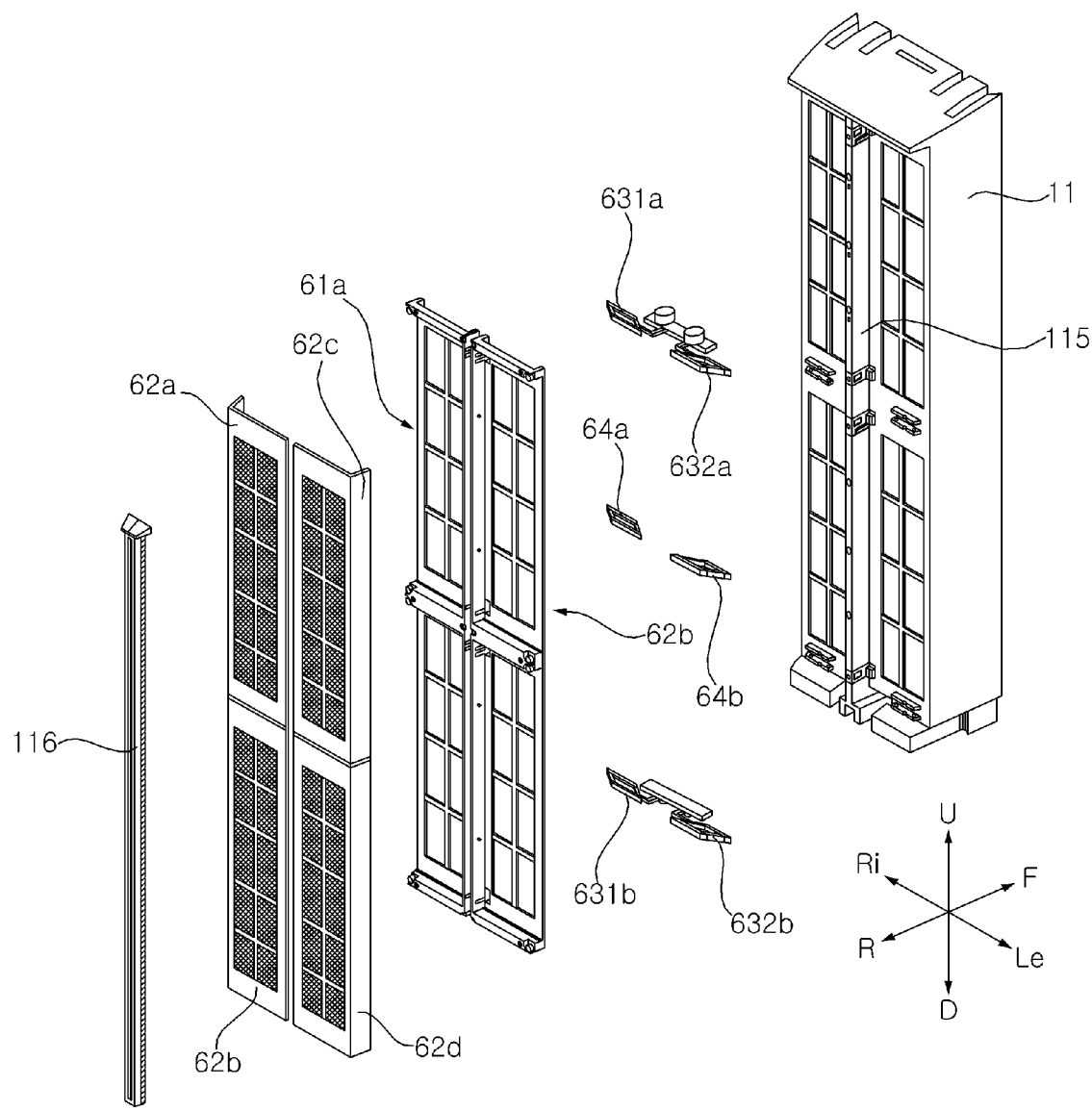
FIG. 6 is an exploded perspective view of an upper cabinet and a filter assembly according to an embodiment of the present invention.
Figure 7:
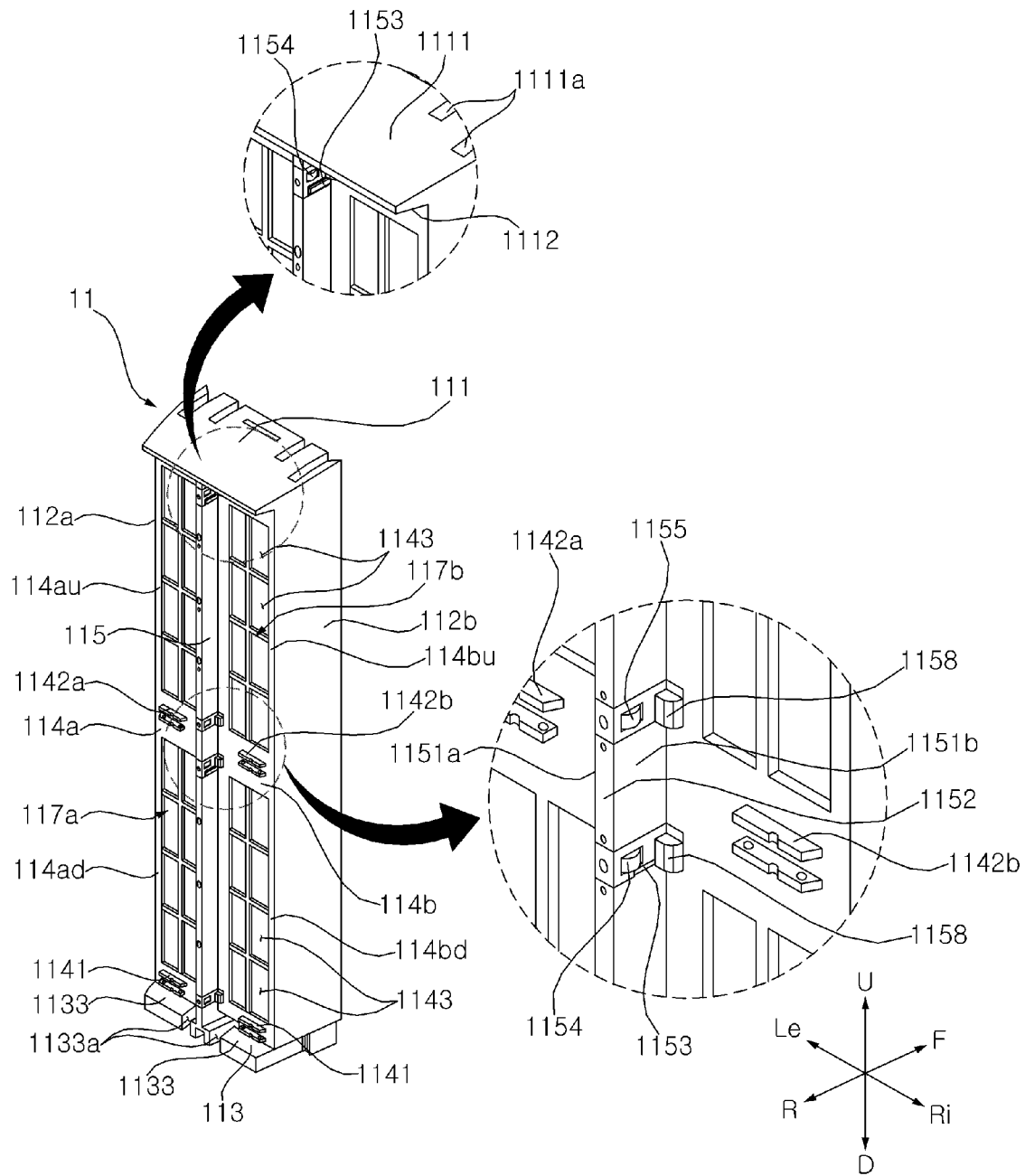
FIG. 7 is a rear perspective view of an upper cabinet according to an embodiment of the present invention.
Figure 8:
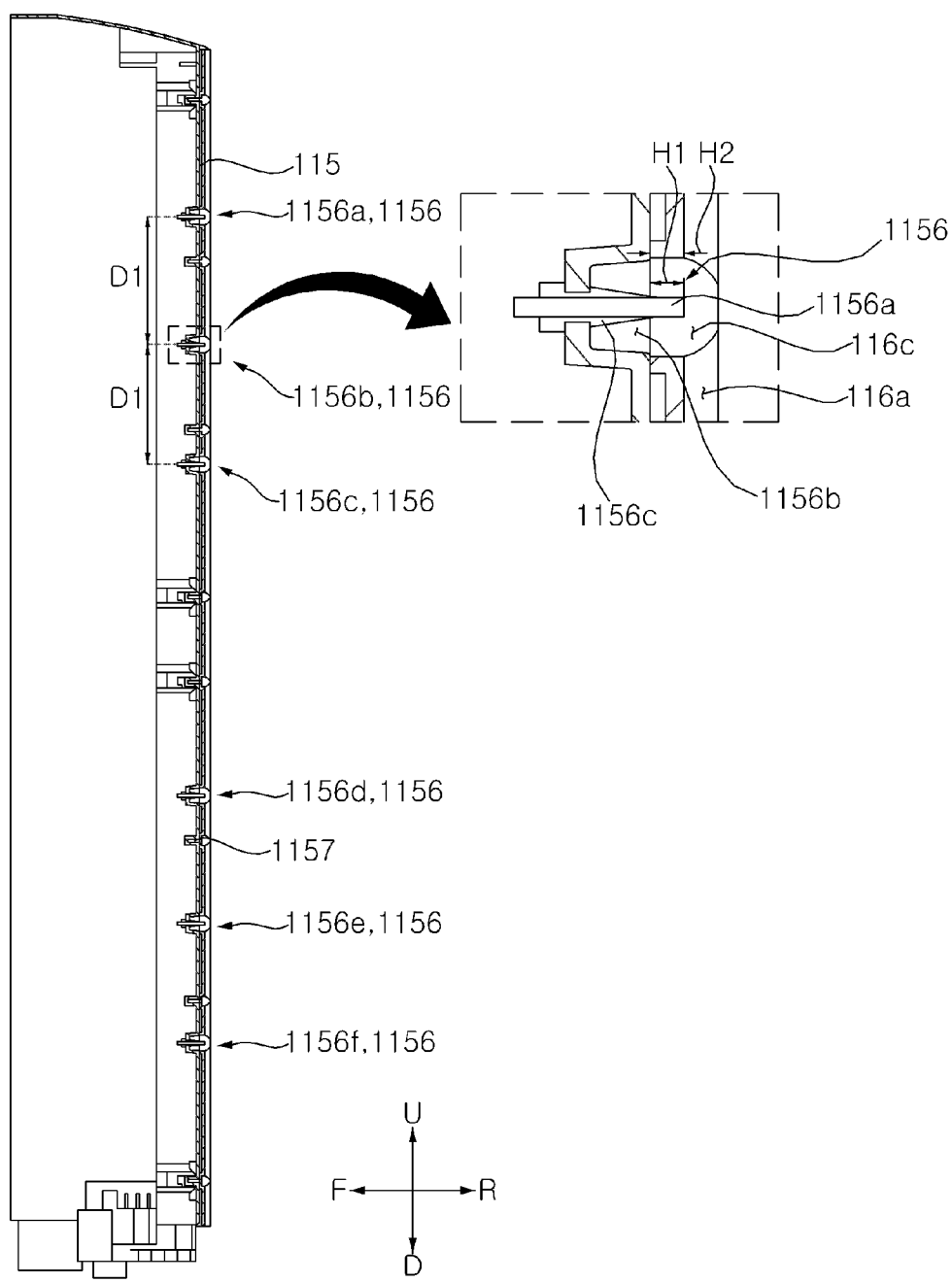
FIG. 8 is a cross-sectional view cut along line X1-X1' in FIG. 5.

Referring to FIGS. 5 and 6, a filter assembly VI according to the present embodiment is movably disposed at a rear side of an upper cabinet 11. The filter assembly VI may be disposed at the suction port 1143 formed in the rear surface of the upper cabinet 11 and filter indoor air flowing through the suction port 1143. The filter assembly VI is disposed movably with respect to the upper cabinet 11.

The filter assembly VI according to the present embodiment includes a filter modules 62a, 62b, 62c, and 62d for removing foreign substances from air suctioned into the suction port 1143. In the filter assembly VI, the filter modules 62a, 62b, 62c, and 62d may be disposed at the suction port 1143 or disposed external to side surfaces 112a and 112b of the upper cabinet 11.

The filter assembly VI may include: the filter modules 62a, 62b, 62c, and 62d for removing dust contained in airflow; filter mounting members 61a and 61b to which the filter modules 62a, 62b, 62c modules 62a, 62b, 62c, and 62d are mounted; and mobile members 631a, 631b, 632a, and 632b for changing a position of the filter mounting members 61a and 61b. The filter assembly may further include driving devices 633a, 633b, 633a', and 633b' connected to the filter mounting members 61a and 61b to move the position of the filter mounting members 61a and 61b. The filter assembly VI may further include guide members 64a and 64b moving in accordance with movement of the mobile members 631a, 631b, 632a, and 632b and assisting movement of the filter amounting members 61a and 61b.

The filter assembly VI may include: a first filter mounting member 61a disposed on the left side in rear of the upper cabinet 11; and a second filter mounting member 61b disposed on the left side in rear of the upper cabinet 11. The filter assembly VI may include an upper filter module 62a and a lower filter module 62b disposed in the upward and downward direction with respect to the first filter mounting member 61a; and a second upper filter module 62c and a second lower filter module 62d disposed in the upward and downward direction with respect to the second filter mounting member 61b.

The filter assembly VI may include: first mobile members 631a and 631b connected to the first filter mounting member 61a to move the position of the first filter mounting member 61a; and second mobile members 632a and 632b connected to the second filter mounting member 61b to move the position of the second filter mounting member 61b. The first mobile members 631a and 631b may move the position of the first filter mounting member 61a disposed on a rear left side of the upper cabinet 11. The second mobile members 632a and 632b may move the position of the second filter mounting member 61b disposed on a rear right side of the upper cabinet 11.

The first mobile members 631a and 631b may include: a first upper mobile member 631a disposed in an upper portion of the upper cabinet 111, and a first lower mobile member 631b disposed in a lower portion of the upper cabinet 11. The second mobile members 632a and 632b may include: a second upper mobile member 632a disposed in the upper portion of the upper cabinet 11; and a second lower mobile member 632b disposed in the lower portion of the upper cabinet 11.

The guide members 64a and 64b may include: a first guide member 64a connected to the first filter mounting member 61a; and a second guide member 64b connected to the second filter mounting member 61b. The first guide member 64a may be disposed between the first upper mobile member 631a and the first lower mobile member 631b to guide position change by the first filter mounting member 61a. The second guide member 64b may be disposed between the second upper mobile member 632a and the second lower mobile member 632b to guide position change by the second filter mounting member 61b.

In the filter assembly VI according to the present embodiment, the driving devices 633a, 633b, 633a', and 633b' press the mobile members 631a 631b, 632a, and 632b, and the mobile members 631a, 631b, 632a, and 632b change the position of the filter mounting members 61a and 61b. However, this is merely an example. It is understood that the driving device may be omitted. In this case, the position of the filter mounting members 61a and 61b may be manually changed by a user. However, a changed position of the filter mounting members 61a and 61b may be guided by the mobile members 631a 631b, 632a, 632b connected to both the cabinet assembly I and the filter mounting members 61a and 61b.

<Cabinet Assembly-Upper Cabinet>

Referring to FIGS. 6 to 9, 12, and 24, an upper cabinet 11 according to the present embodiment has a box shape having an open front surface, and a plurality of suction ports in the rear thereof. A filter assembly VI is disposed in rear of the upper cabinet 11. The filter assembly is movably disposed in rear of the upper cabinet 11.

The upper cabinet 11 may include: an top part 111 disposed to cover the top; lateral parts 112a and 112b disposed to cover both side surfaces; a bottom part 113 disposed at the bottom and fastened to a base unit 12; and rear parts 114a and 114b in which the filter assembly VI is movably disposed.

The top part 111 may include: a top cover surface 1111 disposed external to the top of the indoor unit; and a top surface 1112 of the filter mounting member mount bases 117a and 117b covering the top of a mobile member receiving space 612s where the upper mobile members 631a and 632a are received. The top cover surface 1111 may have a shape that is inclined upward from the rear to the front, and a plurality of reinforcing grooves 111a concave downward may be formed in the front of the top cover surface 111 in the forward and rearward direction.

The bottom part 113 may include a bottom surface 1133 of the filter mounting part mount bases 117a and 117b that covers the bottom of the mobile member receiving space 612s where the lower mobile member 631b and 632b when the filter mounting members 61a and 61b are mounted to the upper cabinet 11. On the bottom surfaces of the filter mounting part mount bases 117a and 117b, there may be formed a link hole 1133 penetrated by vertical link bars 6364a' and 6364b' of motor links 636a' and 636b' of the lower mobile members 631b and 632b, which will be described in the following.

Figure 9:
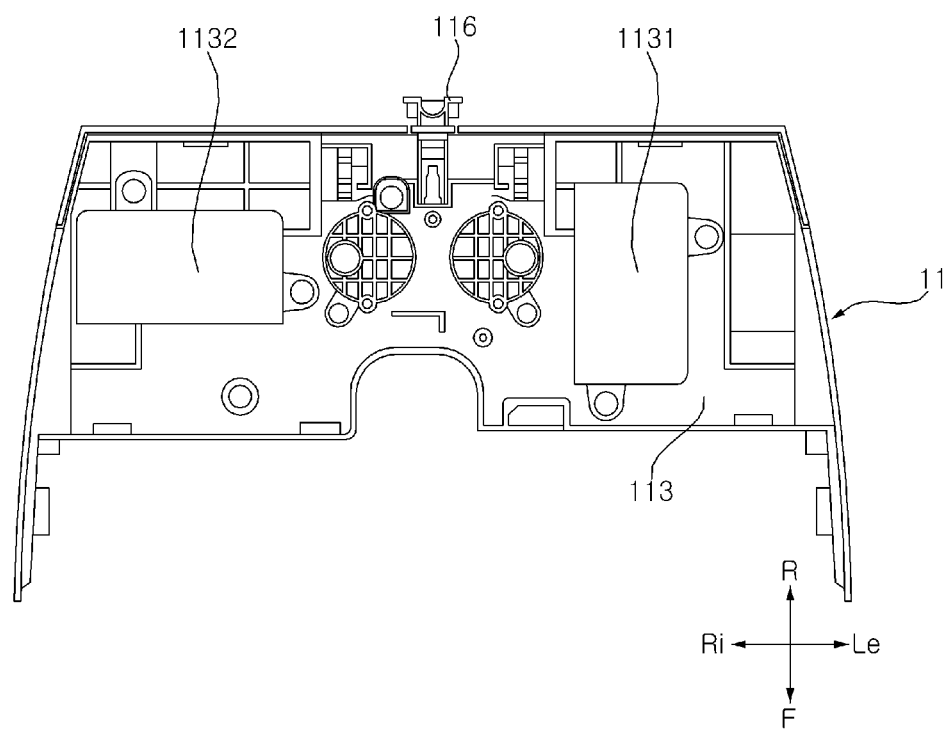
FIG. 9 is a bottom view of an upper cabinet according to an embodiment of the present invention.
Figure 10:
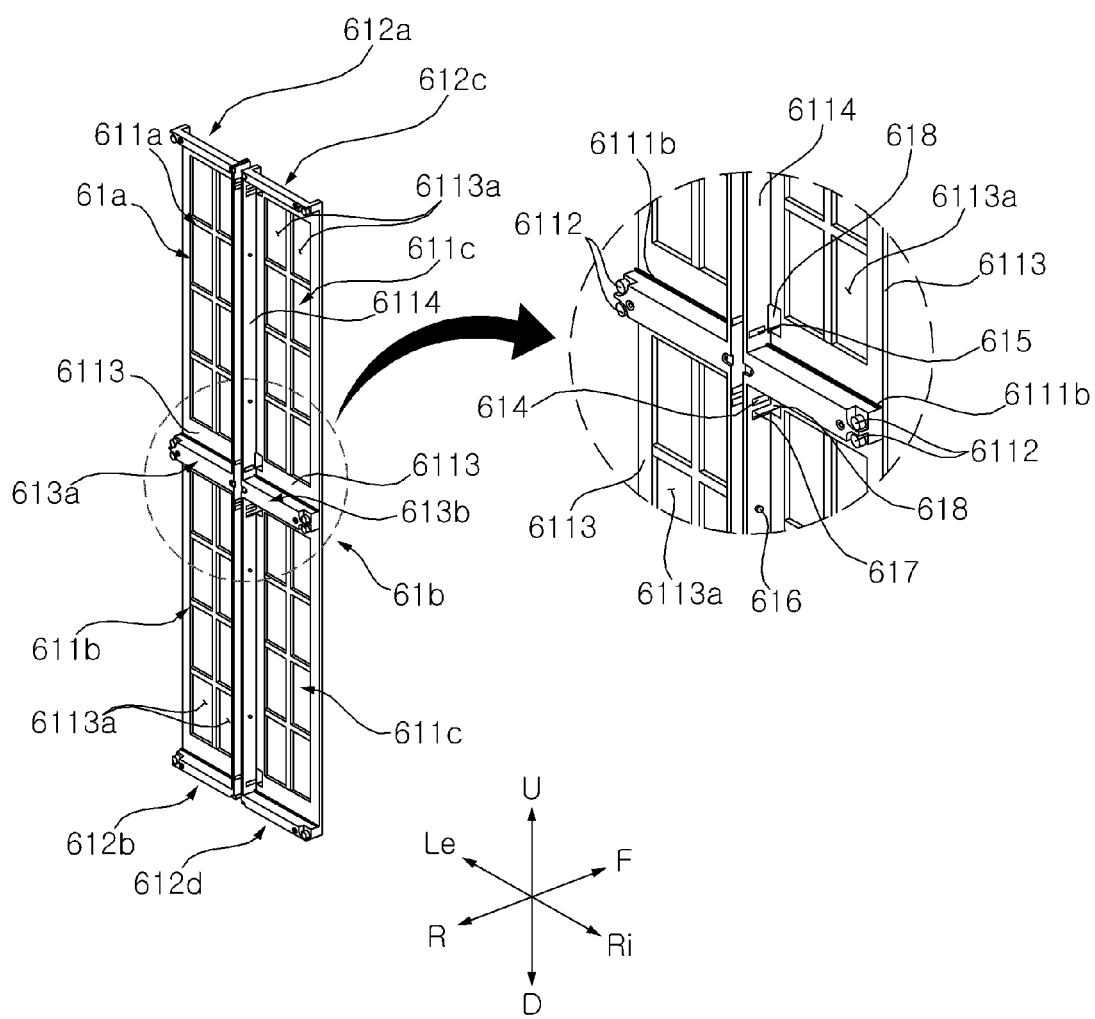
FIG. 10 is a rear perspective view of a filter mounting member according to an embodiment of the present invention.
Figure 11:
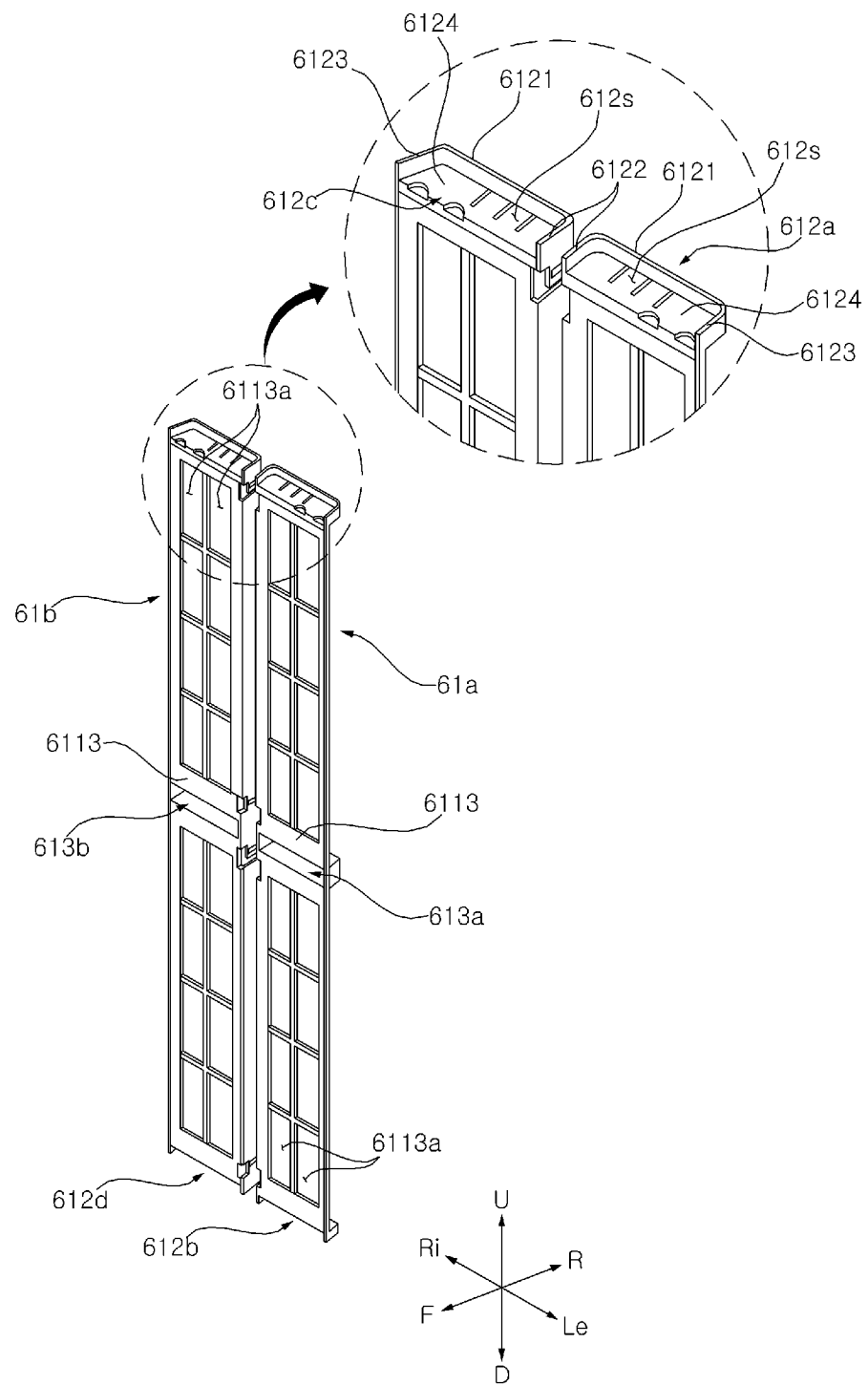
FIG. 11 is a front perspective view of a filter mounting member according to an embodiment of the present invention.
Figure 12:
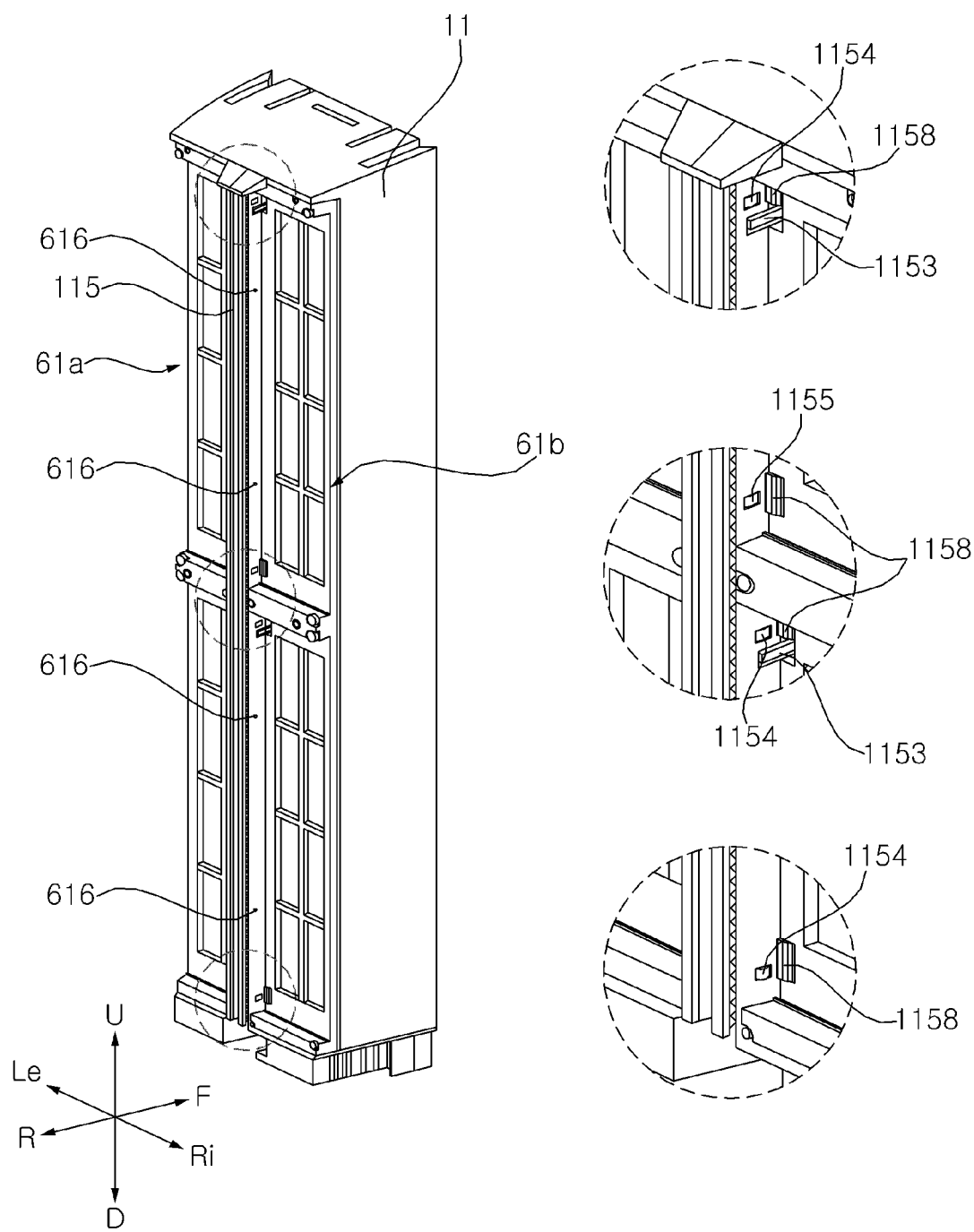
FIG. 12 is a rear perspective view of an upper cabinet with a filter mounting member mounted thereto according to an embodiment of the present invention.
Figure 13:
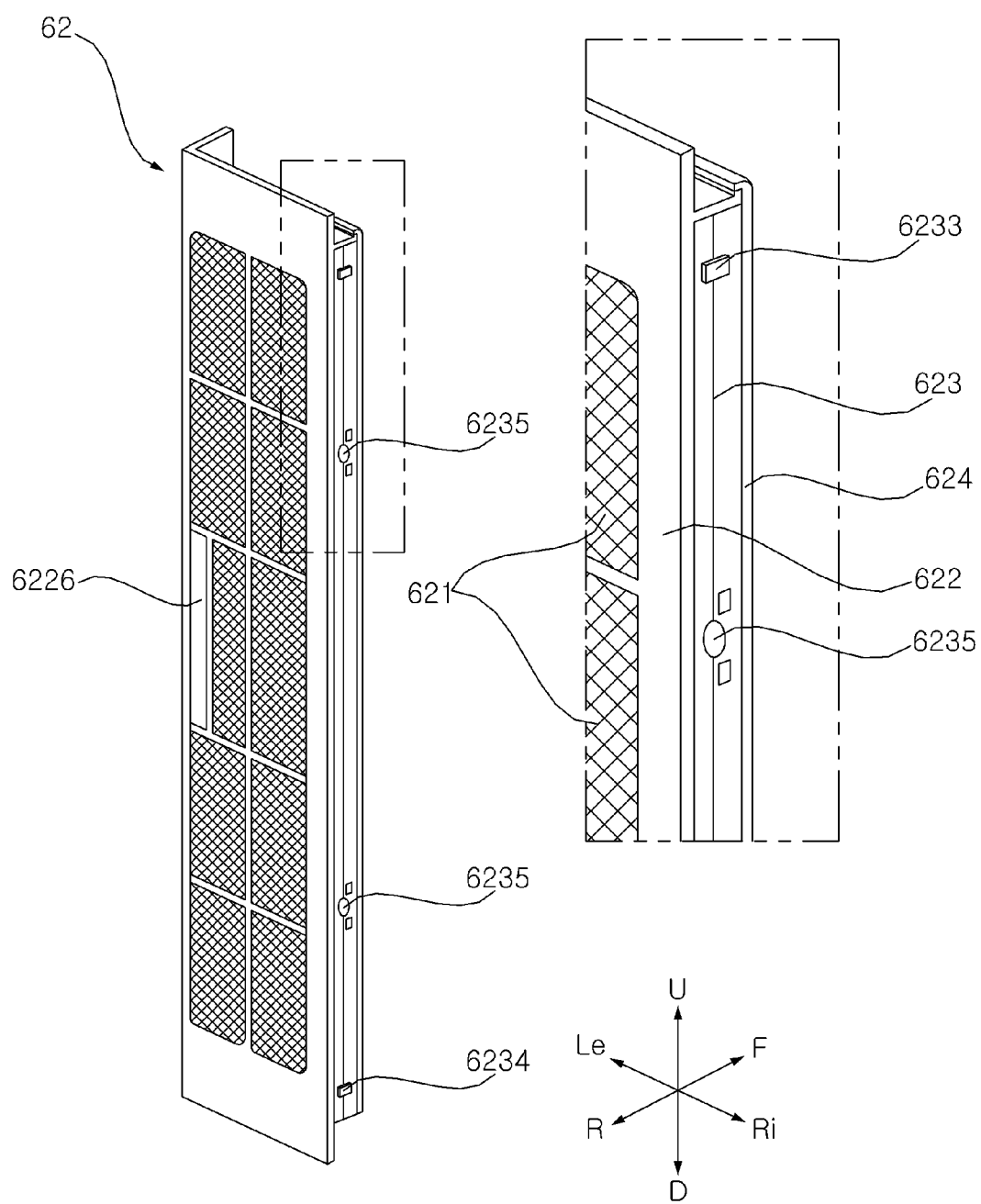
FIG. 13 is a rear perspective view of a filter module according to an embodiment of the present invention.
Figure 14:
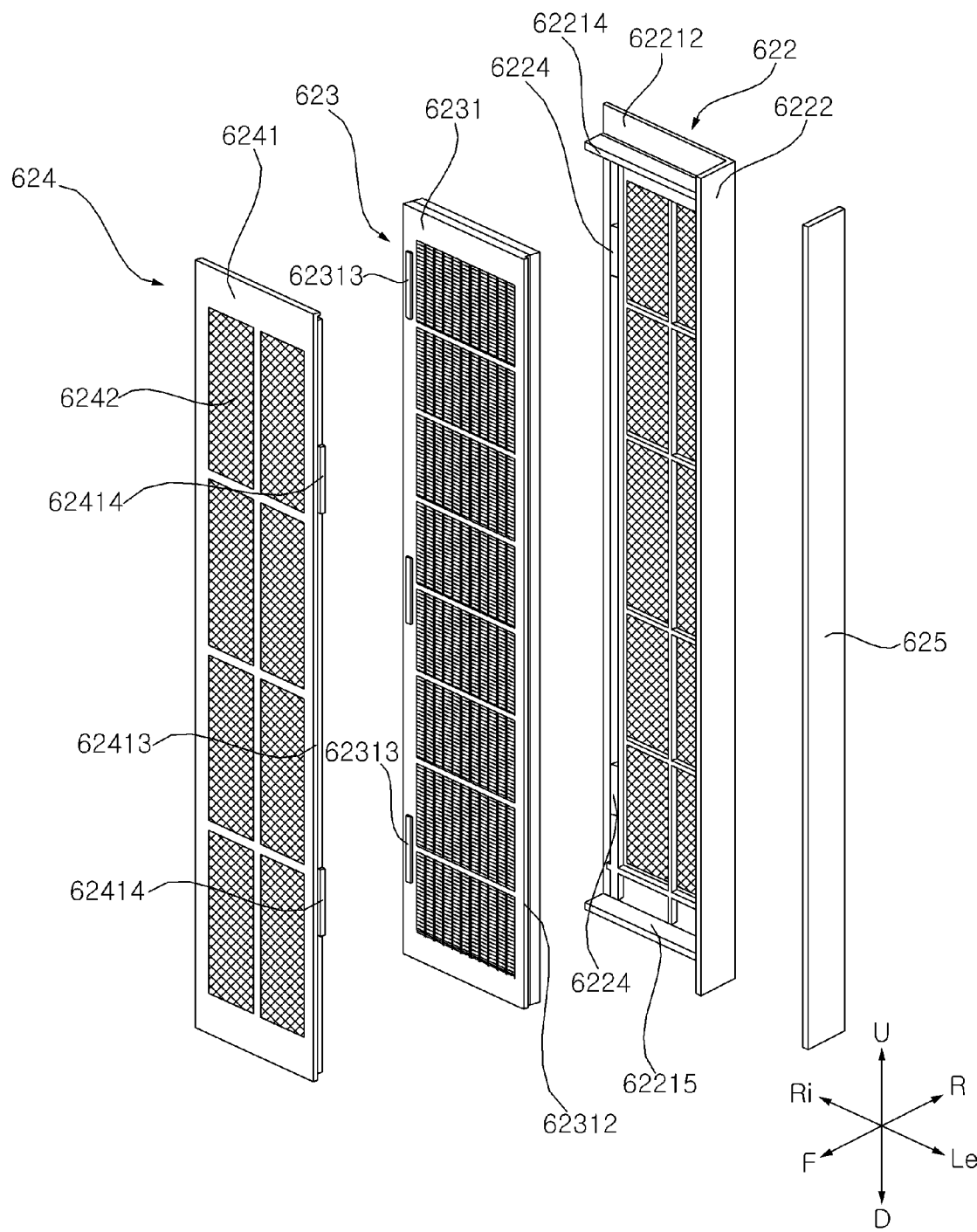
FIG. 14 is a front exploded perspective view of a filter module according to an embodiment of the present invention.
Figure 15:
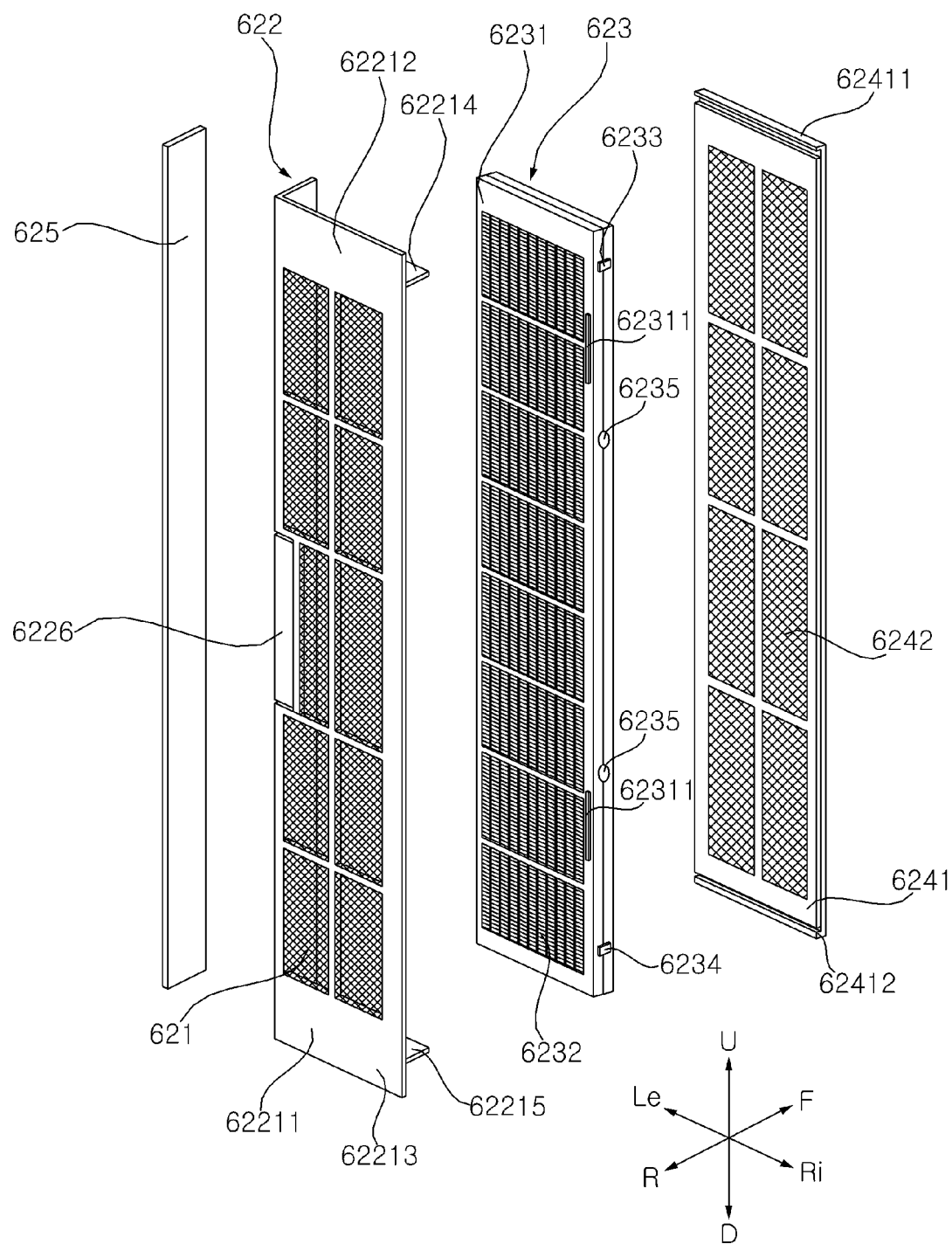
FIG. 15 is a rear exploded perspective view of a filter module according to an embodiment of the present invention.
Figure 16:
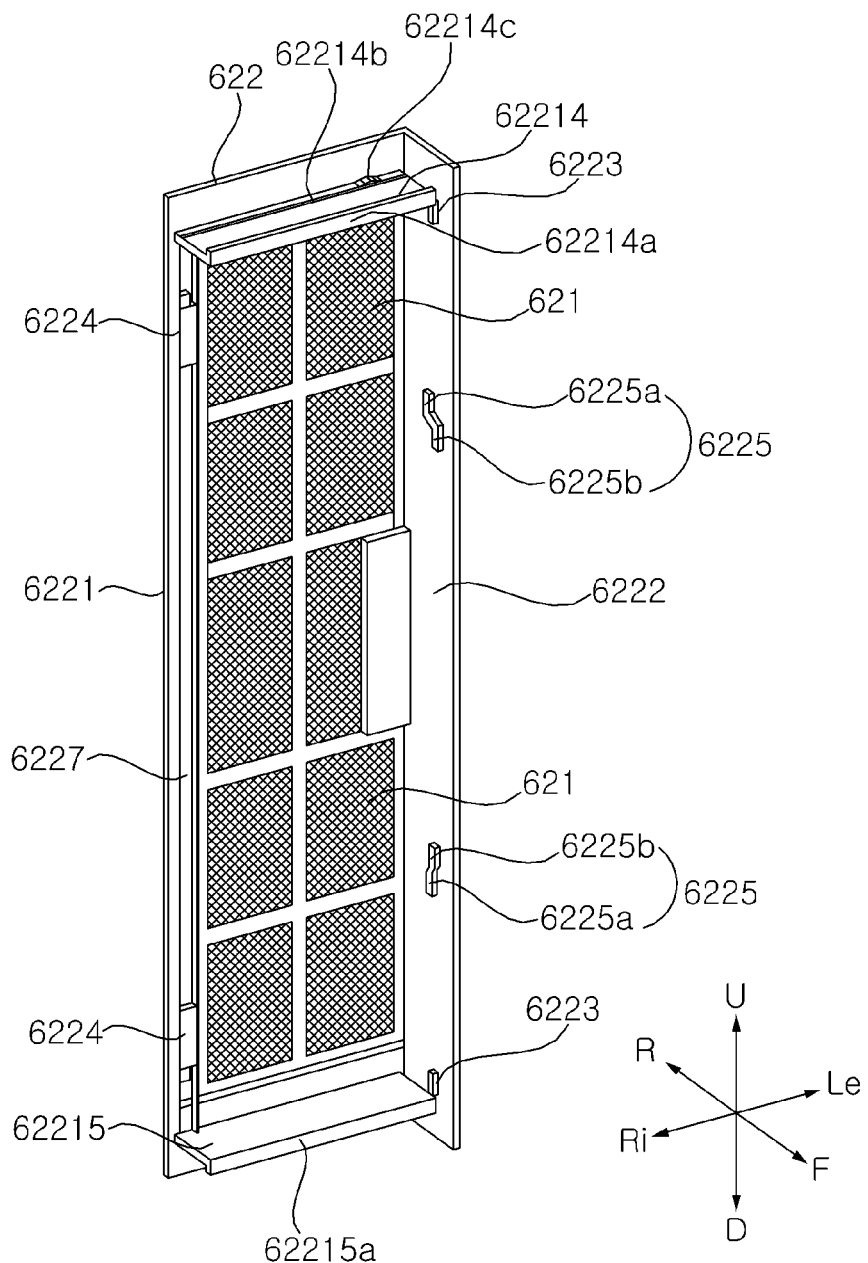
FIG. 16 is a front perspective view of a filter case according to an embodiment of the present invention.
Figure 17:
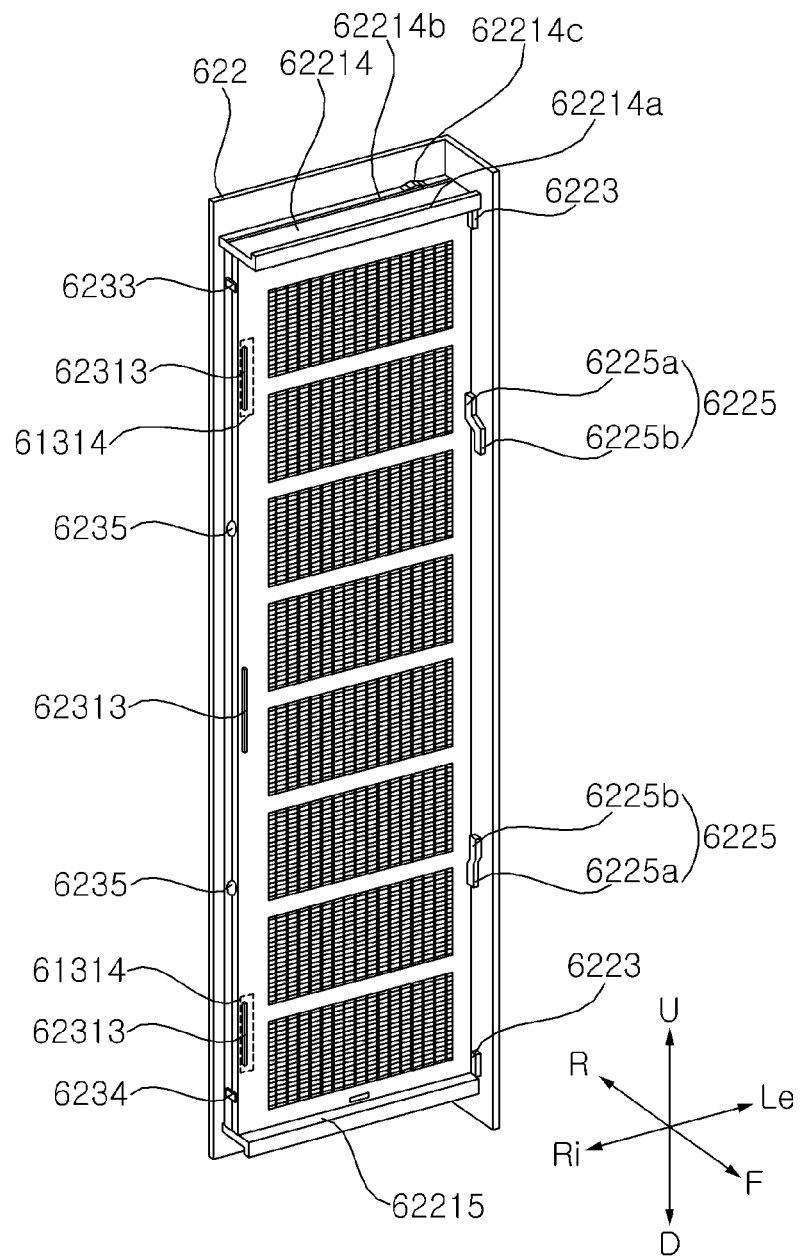
FIG. 17 is a front perspective view of FIG. 16 with a dust collecting filter unit mounted thereto.
Figure 18:
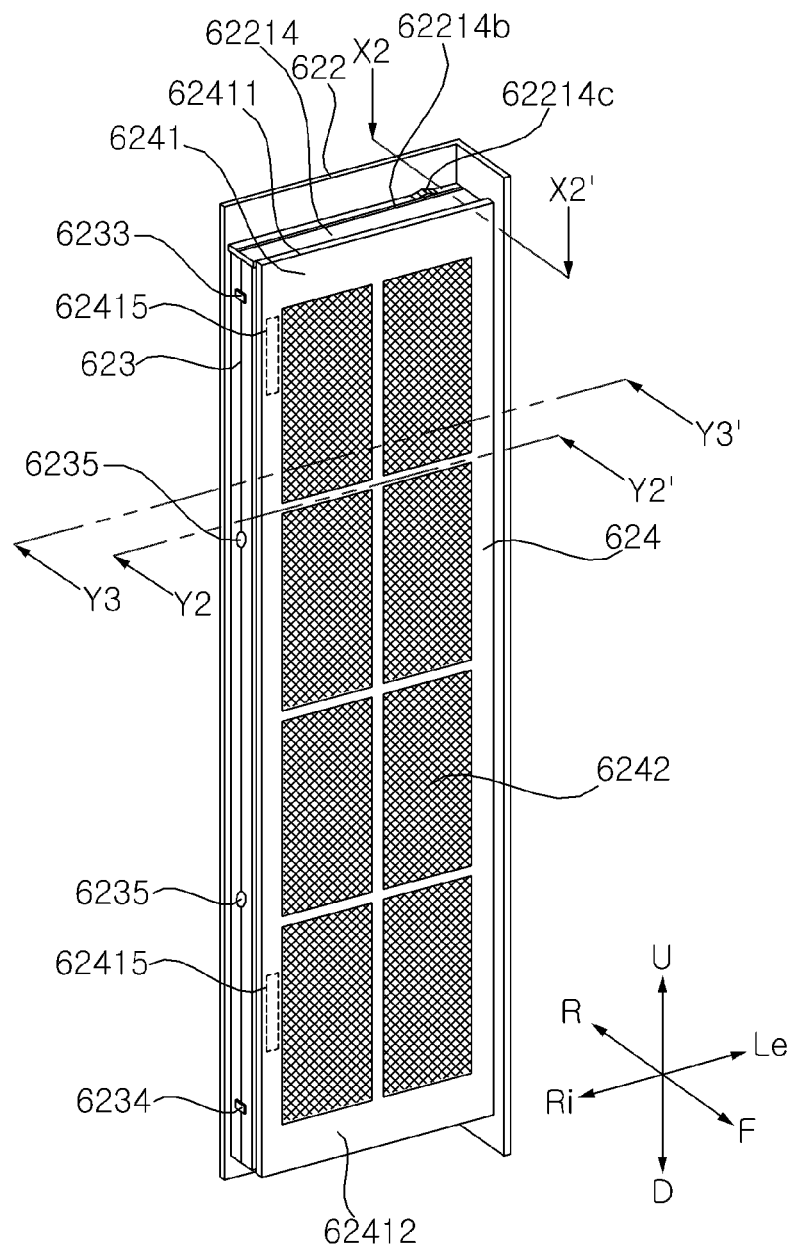
FIG. 18 is a front perspective view of FIG. 17 with a deodorization filter unit mounted thereto.
Figure 19:
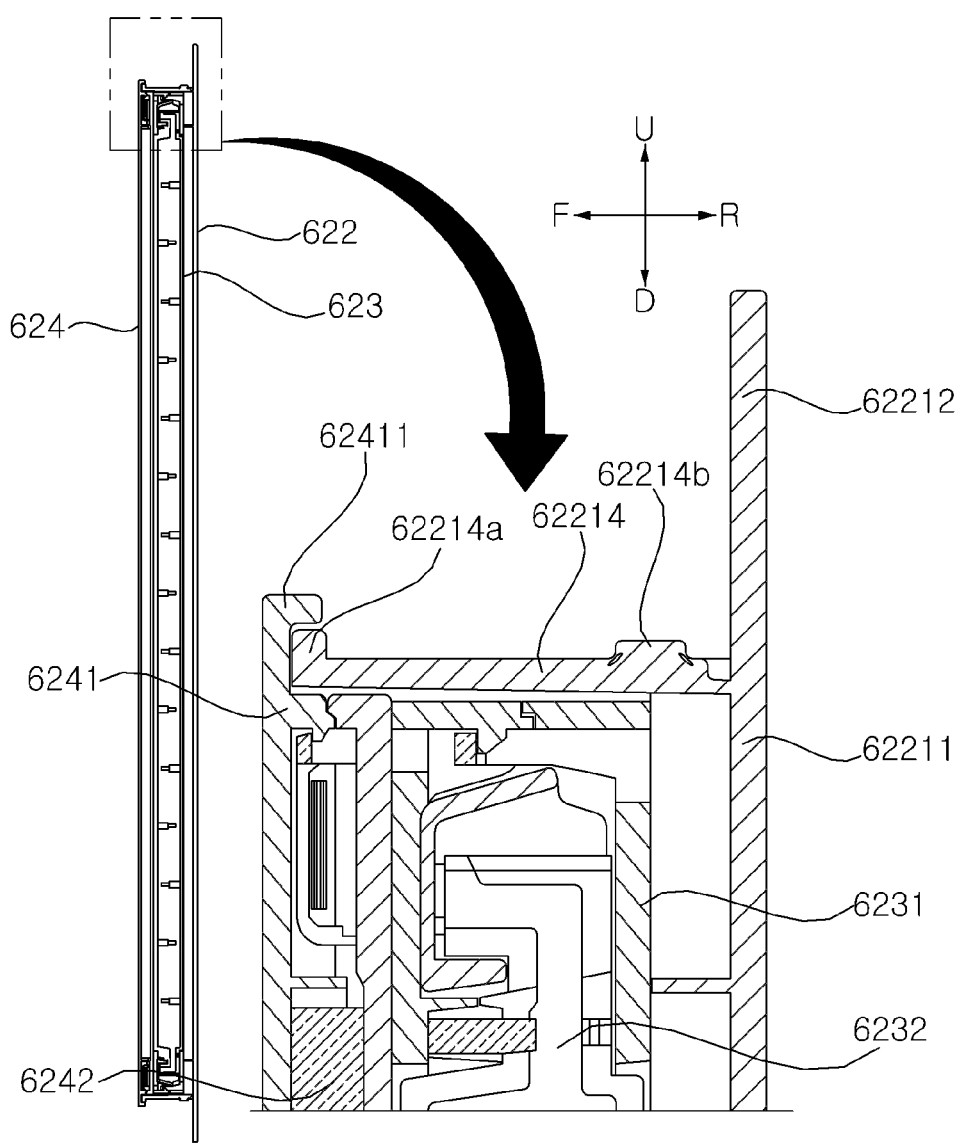
FIG. 19 is a cross-sectional view cut along line X2-X2' in FIG. 18.
Figure 20:
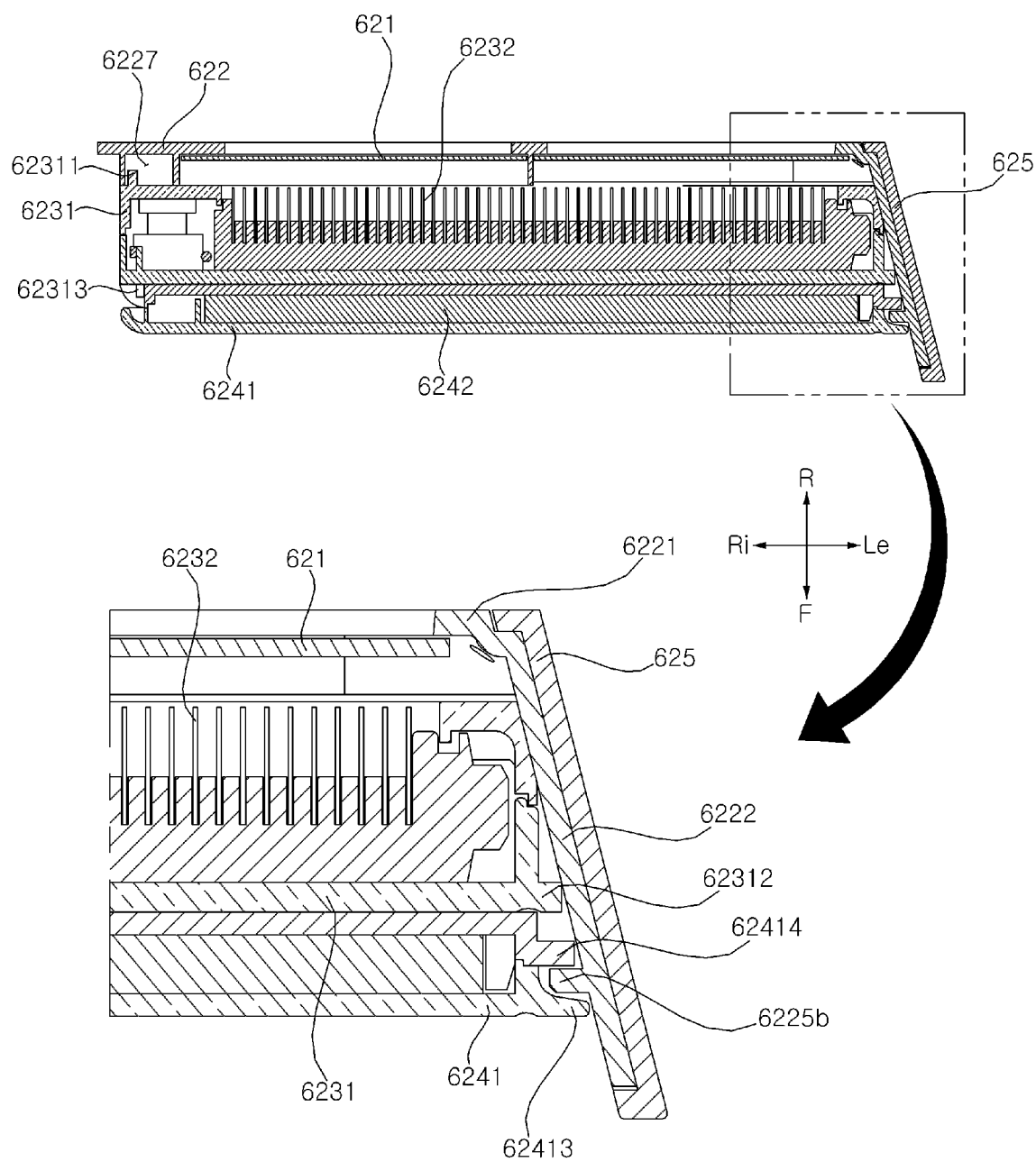
FIG. 20 is a cross-sectional view cut along line Y2-Y2' in FIG. 18.
Figure 21:
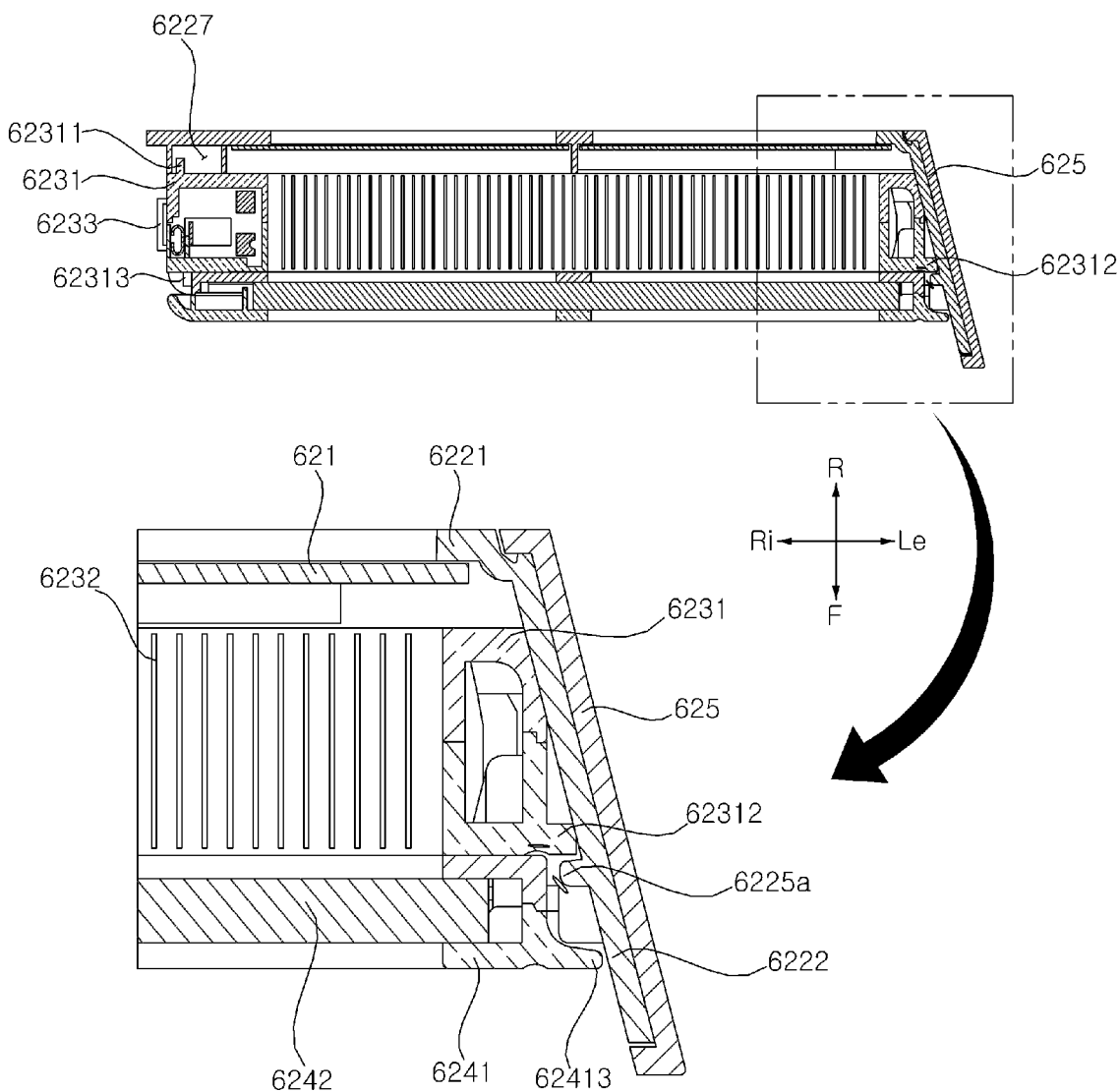
FIG. 21 is a cross-sectional view cut along line Z2-Z2' in FIG. 18.
Figure 22:
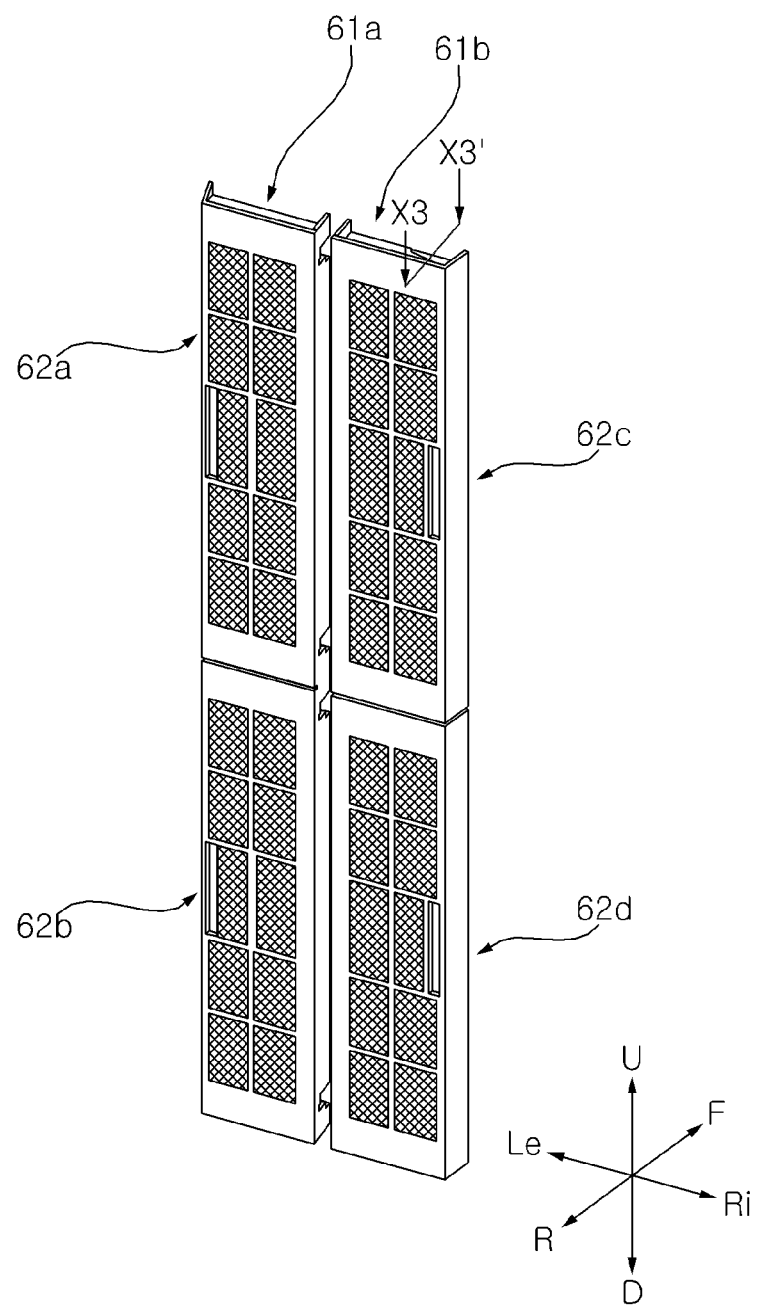
FIG. 22 is a rear perspective view of a filter mounting member with a filter module mounted thereto according to an embodiment of the present invention.
Figure 23:
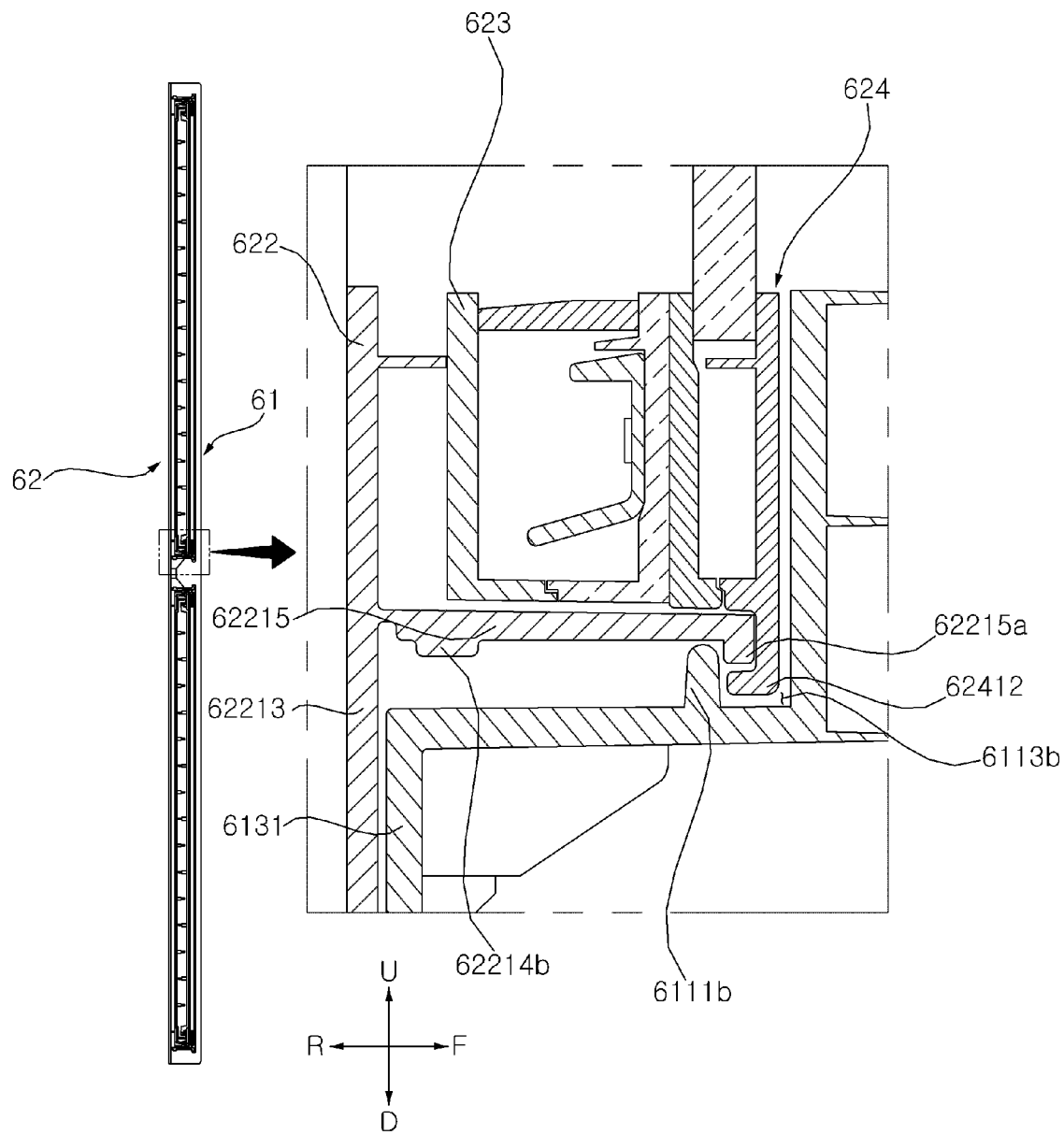
FIG. 23 is a cross-sectional view cut along line X3-X3' in FIG. 22.
Figure 24:
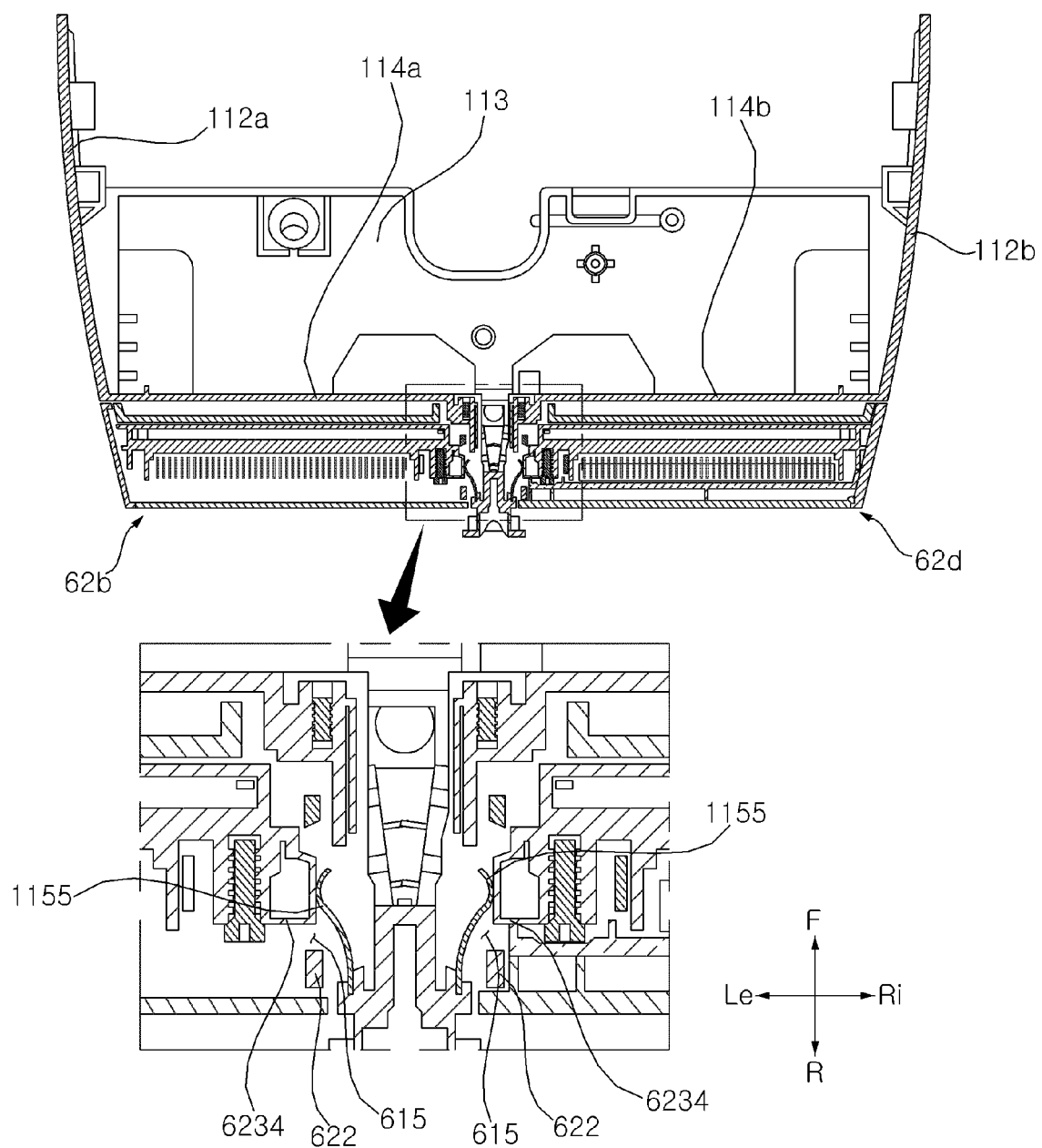
FIG. 24 is a cross-sectional view cut along line Y1-Y1' in FIG. 5.
Figure 25:
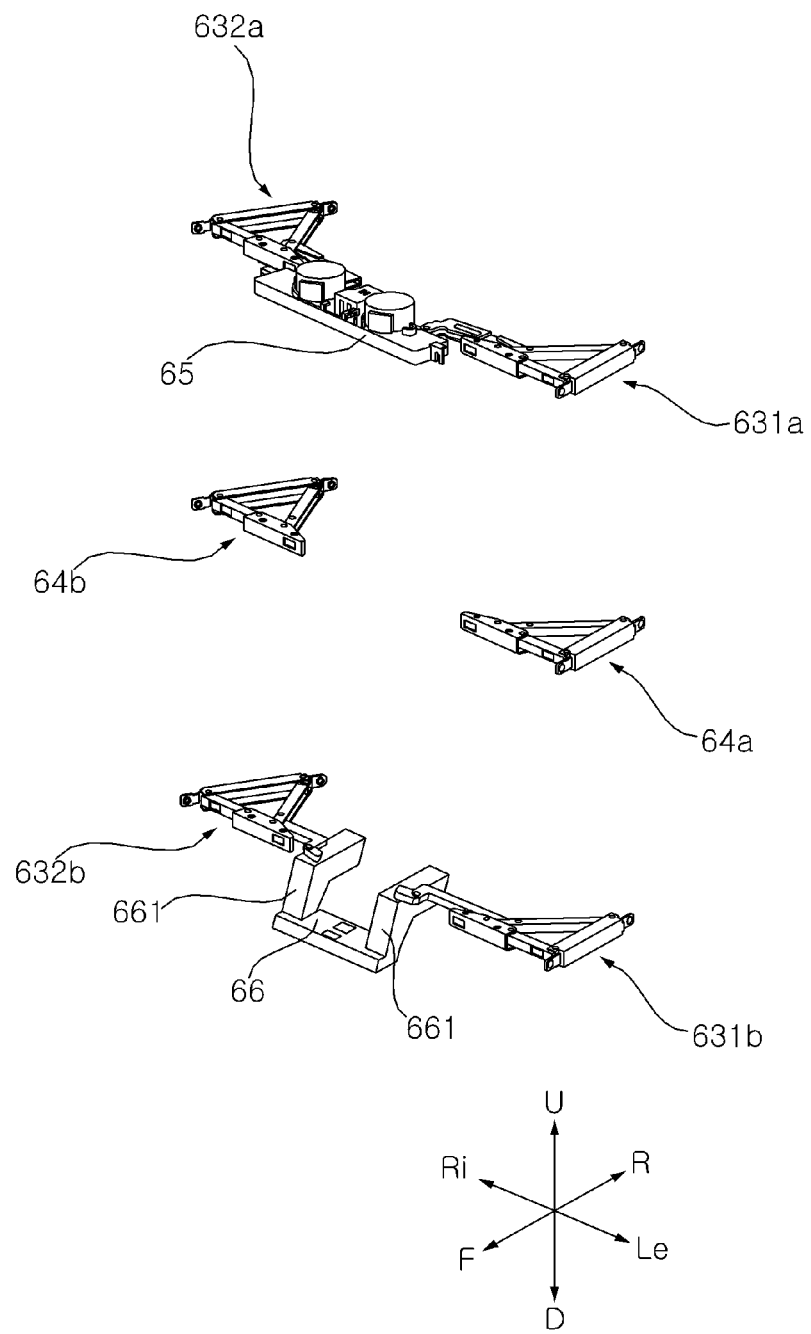
FIG. 25 is a front perspective view of a mobile member and a guide member according to an embodiment of the present invention.
Figure 26:
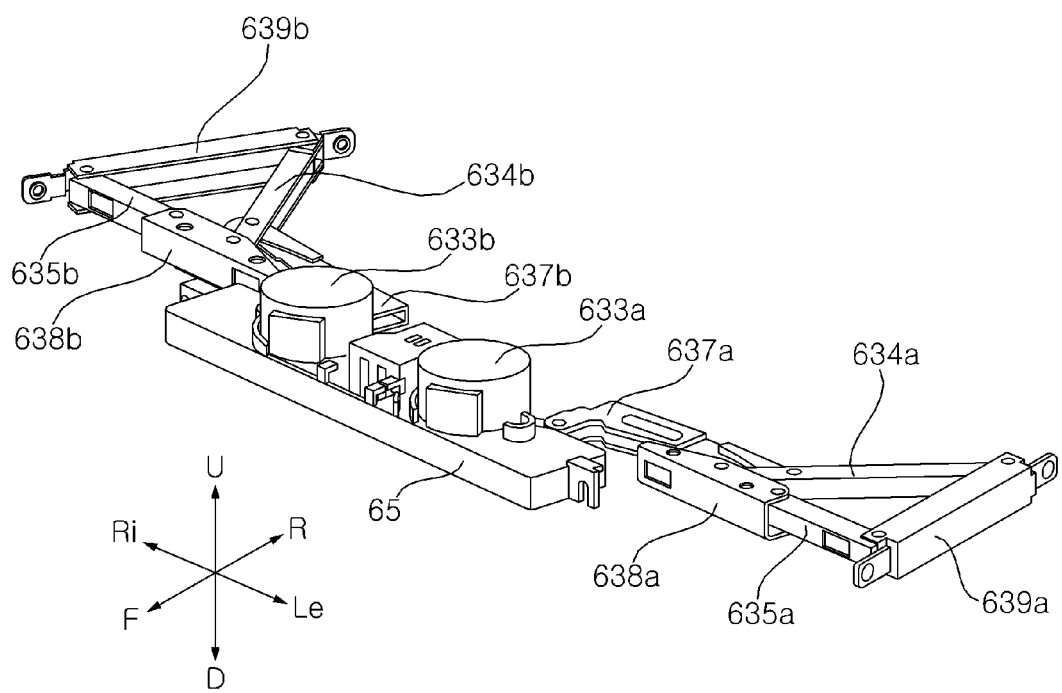
FIG. 26 is a perspective view of a first upper mobile member, a second upper mobile member, and an upper driving device fixing plate according to an embodiment of the present invention.
Figure 27:
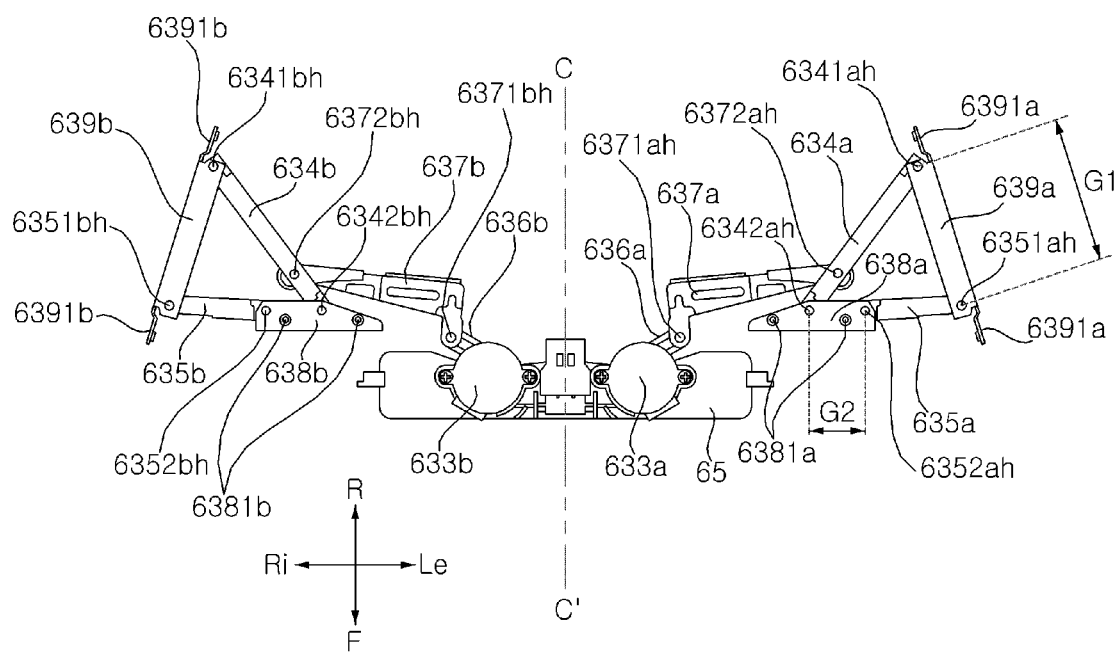
FIG. 27 is a plan view of a first upper mobile member, a second upper mobile member, and an upper driving device fixing plate at a second position P2 according to an embodiment of the present invention.
Figure 28:
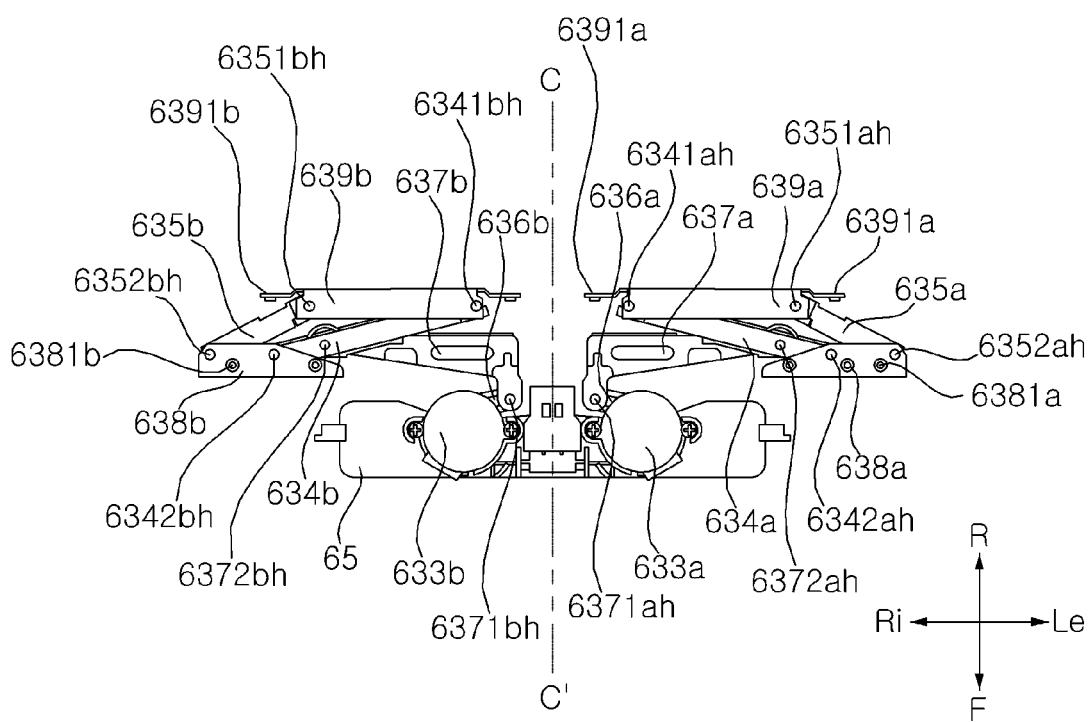
FIG. 28 is a plan view of a first upper mobile member, a second upper mobile member, and an upper driving device fixing plate at a first position P1 according to an embodiment of the present invention.
Figure 29:
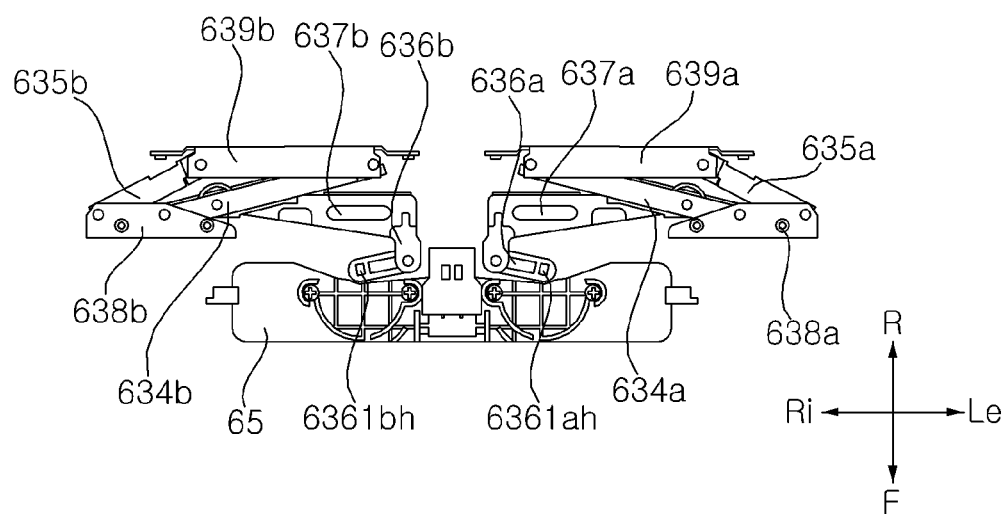
FIG. 29 is a plane view of FIG. 28 with a driving device removed.
Figure 30:
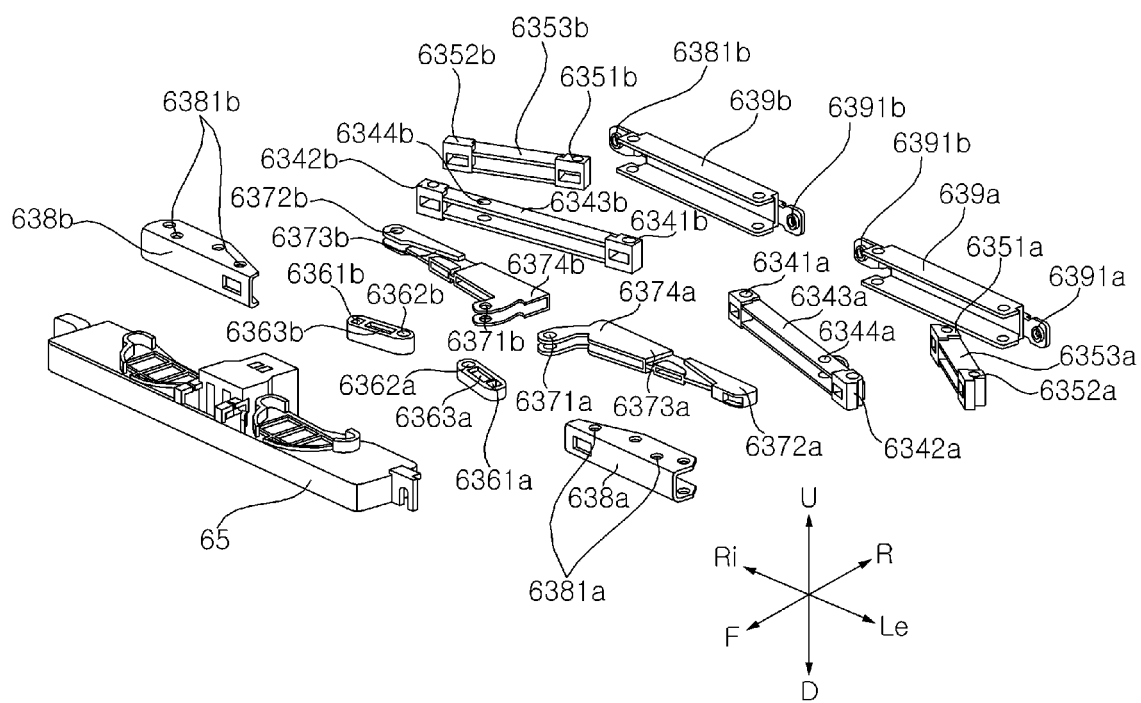
FIG. 30 is an exploded perspective view of a structure shown in FIG. 28.

Referring to FIG. 9, a first high voltage generator 1131 to supply a voltage to a power terminal 1154 or ground terminal 1155 or to provide a ground, and a second high voltage generator 1132 to apply a high voltage to an ionizing part 1156 may be disposed on a lower side of the bottom part 113.

The rear parts 114a and 114b may be spaced apart from the rear ends of the upper part 111 and the lower end 113 so as to form a space where the filter assembly VI is disposed.

In the rear parts 114a and 114b of the upper cabinet 11, the mobile members 631a, 631b, 632a, and 632b moving the filter mounting parts 61a and 61b of the filter assembly VI is disposed. In the rear parts 114a and 114b of the upper cabinet 11, there are formed the guide members 64a and 64b moving in accordance with movement of the mobile members 631a, 631b, 632a, and 632b and assisting movement of the filter mounting members 61a and 61b. The rear parts 114a and 114b of the upper cabinet 11 may include: a first rear part 114a in which the first filter mounting member 61a; and a second rear part 114b in which the second filter mounting member 61b. The first rear part 114a may be disposed on the rear left side of the upper cabinet 11, and the second rear part 114b may be disposed on the rear right side of the upper cabinet 11.

The mobile member fixing part 1141, to which the mobile members 631a 631b, 632a, and 632b are fixed, and the guide member fixing parts 1142a and 1142b, to which the guide members 64a and 64b are fixed, may be formed in each of the first rear part 114a and the second rear part 114b. In each of the first rear part 114a and the second rear part 114b, a plurality of suction ports 1143 may be formed vertically with respect to the guide member fixing parts 1142a and 1142b.

The first rear part 114a may be divided into a first rear part-upper portion 114au on which the first upper filter module 62a is disposed, and a first rear part-lower portion 114ad on which the lower filter module 62b is disposed. Likewise, the second rear part 114b may be divided into a second rear part-upper portion 114bu on which the second upper filter module 62c is disposed, and a second rear part-lower portion 114bd on which the second lower filter module 62d is disposed.

When the filter mounting member 61a is disposed in the rear of the first rear part 114a, the first upper filter module 62a is disposed in rear of the first rear part-upper portion 114au and the first lower filter module 62b is disposed in rear of the first rear part-lower portion 114ad.

When the second filter mounting member 61b is disposed in rear of the second rear part 114b, the second upper filter module 62c is disposed in rear of the second rear part-upper portion 114bu and the second lower filter module 62d is disposed in rear of the second lower part-lower portion 114bd.

The upper cabinet may further include a rearward protruding member 115 disposed in the middle of the rear parts 114a and 114b and protruding rearward. The upper cabinet 11 may further comprise the rearward protruding member 115 disposed between the first rear part 114a and the second rear part 114b and protruding rearward. The rearward protruding member 115 may protrude rearward from the middle of the rear parts 114a and 114b. The rearward protruding member 115 may be elongated in the upward and downward direction in rear of the upper cabinet 11.

The rearward protruding member 114 may include: protruding surfaces 1151a and 1151b which protrude rearward from the rear parts 114a and 114b to form a surface opposing one side surface of the filter mounting members 61a and 61b; and a guiderail mounting surface 1152 which forms a surface parallel to the rear parts 114a and 114b at an end portion of the protruding surfaces 1151a and 1151b, and to which the guiderail 116 is mounted.

The rearward protruding member 115 may include a first protruding surface 1151a protruding rearward from the first rear part 114a, and a second protruding surface 1151b protruding rearward from the second rear part 114b. The guiderail mounting surface 1142 may be formed as a surface that connects a rear end of the first rear part 114a and a rear end of the second rear surface.

The first protruding surface 1151a and the second protruding surface 1151b may be formed vertical to the first rear part 114a and the second rear part 114b, respectively, and the guiderail mounting surface 1152 may be formed vertical to each of the first rear part 114a and the second rear part 114b.

The upper cabinet 11 may include the filter mounting part mount bases 117a and 117b to which the filter mounting members 61a and 61b are respectively mounted. The filter mounting part mount bases 117a and 117b may include: the rear parts 114a and 114b in which the suction ports 1143 are formed; and the protruding surfaces 1151a and 1151b which are formed in the rear parts 114a and 114b in a protruding manner.

When the filter mounting members 61a and 61b are mounted to the filter mounting member mount bases 117a and 117b, each of the rear parts 114a and 114b and the protruding surfaces 1151a and 1151b may be disposed in contact with surfaces corresponding to the filter mounting members 61a and 61b, or may be disposed to oppose to the surface corresponding to the filter mounting members 61a and 61b.

The upper cabinet 11 may include: a first filter mounting member mount 117a to which the first filter mounting member 61a is mounted; and a second filter mounting member mount 117b to which the second filter mounting member 61b is mounted. Thus, the first filter mounting member mount 117a may include the first rear part 114a and the first protruding surface 1151a, and the second filter mounting member mount 117b may include the second rear part 114b and the second protruding surface 1151b.

When the filter mounting members 61a and 61b are mounted to the filter mounting member mount bases 117a and 117b, the filter mounting members 61a and 61b are disposed such that air flowing toward the suction ports 1143 of the upper cabinet 11 passes through the filter modules 62a, 62b, 62c, and 62d of the filter mounting members 61a and 61b. Here, the case where the filter mounting members 61a and 61b are mounted to the filter mounting member mount bases 117a and 117b or the upper cabinet 11 may refer to a state in which the filter mounting members 61a and 61b are no longer allowed to move in a forward direction or in a center direction of the upper cabinet 11.

Thus, when the filter mounting members 61a and 61b are mounted to the filter mounting member mount bases 117a and 117b, the power terminal 1154 installed on the upper cabinet 11, which will be described later, is brought into contact with a power receiving terminal 6233 of the filter modules 62a, 62b, 62c, and 62d, and the ground terminal 1155 installed on the upper cabinet 11 is brought into contact with a ground receiving terminal 6234 of the filter modules 62a, 62b, 62c, and 62d.

In the rearward protruding member 1115, the guiderail 116 guiding movement of a filter cleaning assembly VII may be mounted.

The guiderail 116 may be fastened to the rear of the rearward protruding member 115. The guide rail 116 may be fastened to a guiderail mounting surface 1152 of the rearward protruding member 115. A fastening groove 1157 for fastening the guide rail 116 to a separate fastening member (not shown) may be formed in the rearward protruding member 115.

In the guide rail 116, a guide groove 116a in which a power line connected to the filter cleaner 71 is disposed may be formed. In the guide rail 116, a fastening hole 116b to which a separate fastening member is mounted may be formed at a position corresponding to the fastening groove 1157 of the rearward protruding member 115. In the guide rail 116, an electrode hole 116c in which an electrode 1156a protruding from the ionization part 1156 is disposed may be formed. The electrode hole 116c may be formed rearward from the rear of the electrode groove 1156b of the ionization part 1156, and an electrode may be positioned after passing through the electrode groove 1156b and the electrode hole 116c.

In the rearward protruding member 115, a filter module recognition sensor 1153 configured to recognize or determine mounting of the filter modules 62a, 62b, 62c, and 62d may be disposed.

In the rearward protruding member 115, a plurality of filter modules recognition sensors 1153 may be disposed to recognize the plurality of filter modules 62a, 62b, 62c, and 63, respectively. The filter module recognition sensor 1153 may sense whether the filter modules 62a, 62b, 62c, and 63 are disposed in rear of the suction port 1143, which will be described later.

The filter module recognition sensor 1153 has a structure of recognizing the presence of the filter modules 62a, 62b, 62c, and 62d when pressed against by inner portions of the filter modules 62a, 62b, 62c, and 62d. When pressed against by inner portions of the filter modules 62a, 62b, 62c, and 62d, the filter module recognition sensor 1153 may recognize that the filter mounting members 61a and 61b with the filter modules 62a, 62b, 62c, and 62d mounted thereto are mounted to the filter mounting member mount bases 117a and 117b.

In this case, the inner portions of the filter modules 62a, 62b, 62c, and 62d correspond to surfaces which faces the insertion face 6114 of the filter mounting members 61a and 61b when the filter modules 62a, 62b, 62c, and 62d are mounted to the filter mounting members 61a and 61b, and which is a surface most closest to the insertion surface 6114. In addition, the inner portions of the filter modules 62a, 62b, 62c, and 62d pressing against the filter module recognition sensor 1153 may correspond to an inner portion of the dust collecting filter unit 623 or an inner portion of the deodorization filter unit 624.

When the filter mounting members 61a and 61b with the filter modules 62a, 62b, 62c, and 62d mounted thereto are mounted to the filter mounting member mount bases 117a and 117b, the filter module recognition sensor 1153 may recognize the filter modules 62a, 62b, 62c, and 62d when the filter mounting members 61a and 61b with the filter modules 62a, 62b, 62c, and 62d mounted thereto are mounted to the filter mounting member mount bases 117a and 117b.

The filter module recognition sensor 1153 may include a plurality of filter module recognition sensors 1153 that are respectively disposed on a first protruding surface 151a and a second protruding surface 1151b, which are formed on both side surfaces of the rearward protruding member 115. The plurality of filter module recognition sensors 1153 may be disposed at positions respectively corresponding to the first upper filter module 62a, the first lower filter module 62b, the second upper filter module 62c, and the second lower filter module 62d.

A power terminal 1154 to supply power to the filter modules 62a, 62b, 62c, and 62d when the filter mounting members 61a and 61b are mounted to the rear of the upper cabinet 11, and a ground terminal 1155 to provide a ground to the filter modules 62a, 62b, 62c, and 62d are disposed in the rearward protruding member 115. A plurality of power terminals 1154 to supply power to the filter modules 62a, 62b, 62c, and 62d, respectively, and a plurality of ground terminals 1155 to provide a ground to the filter modules 62a, 62b, 62c, and 62d, respectively, may be disposed in the rearward protruding member 115.

When the filter modules 62a, 62b, 62c, and 62d mounted to the filter mounting members 61a and 61b are disposed in rear of the suction port 1143, the power terminal 1154 may be brought into contact with a power receiving terminal 6233. When the filter mounting members 61a and 61b with the filter modules 62a, 62b, 62c, and 62d mounted thereto are mounted to the filter mounting member mount bases 117a and 117b, the power terminal 1154 may be brought into contact with the power receiving terminal 6233 of the filter modules 62a, 62b, 62c, and 62d.

When the filter modules 62a, 62b, 62c, and 62d mounted to the filter mounting members 61a and 61b are disposed in rear of the suction port 1143, the ground terminal 1155 may be brought into contact with a ground receiving terminal 6234. When the filter mounting members 61a and 61b with the filter modules 62a, 62b, 62c, and 62d mounted thereto are mounted to the filter mounting member mount bases 117a and 117b, the ground terminal 1155 may be brought into contact with the ground receiving terminal 6234 of the filter modules 62a, 62b, 62c, and 62d.

The power terminal 1154 and the ground terminal 1155 may be disposed on the filter mounting member mount bases 117a and 117b. The power terminal 1154 and the ground terminal 1155 may be disposed on the protruding surfaces 1151a and 1151b. The power terminal 1154 may include a plurality of power terminals 1154 and the ground terminal 1155 may include a plurality of ground terminals 1155 that may be disposed on the first protruding surface 1151a and the second protruding surfaces 1151b, respectively. The plurality of power terminals 1154 and the plurality of ground terminals 1155 may be disposed at positions respectively corresponding to the first upper filter module 62a, the first lower filter module 62b, the second upper filter module 62c, and the second lower filter module 62d.

A mounting protrusion 1158 for mounting the filter mounting members 61a and 61b to a designated or predetermined position in rear of the upper cabinet 11 and maintaining the mounted state may be formed in the rearward protruding member 115. The mounting protrusion 1158 may be formed in plural at portions where the rear parts 114a and 114b and the rearward protruding member 115 are in contact.

When the filter mounting members 61a and 61b are mounted to the upper cabinet 11, the mounting protrusion 1158 may be inserted into a mounting protrusion groove 618 of the filter mounting members 61a and 61b.

An ionization part 1156 to ionize molecules in air, flowing into the suction part 1143, by electric discharge may be disposed in the rearward protruding member 115. A plurality of ionization parts 1156a, 1156b, 1156c, and 1156d may be installed in the rearward protruding member 115 in the upward and downward direction. The ionization part 1156 may be disposed between the first rear part 114a and the second rear part 114b to ionize molecules in air flowing into a plurality of suction ports 1143 formed in the first rear part 114a and the second rear part 114b.

The ionization parts 1156a, 1156b, 1156c, and 1156d may include: a plurality of upper ionization parts 1156a, 1156b, and 1156c disposed between the first upper filter module 62a and the second upper filter module 62c; and a plurality of lower ionization parts 1156d, 1156e, and 1156f disposed between the first lower filter module 62b and the second lower filter module 62d. The plurality of upper ionization parts 1156a, 1156b, and 1156c are preferably spaced apart from each other at a predetermined interval in the upward and downward direction. The plurality of lower ionization parts 1156d, 1156e, and 1156f are preferably spaced apart from each other at a predetermined interval in the upward and downward direction. A distance D1 by which the plurality of upper ionization parts 1156a, 1156b, and 1156c are spaced apart from each other may be correspond to a size of the filter modules 62a, 62b, 62c, and 62d or an intensity of a voltage applied to the electrode 1156a. This may be applied to the plurality of lower ionization parts 1156d, 1156e, and 1156f.

The ionization part 1156 may include: an electrode 1156a to ionize molecules in air by discharging a high voltage; an electrode groove 1156b that forms a space where the electrode 1156a is disposed; and an installation member to fix the electrode 1156a to the electrode groove 1156b.

The electrode 1156a may receive a high voltage from a high voltage generator 1132 generating the high voltage, and ionize molecules in air by electric discharge. The electrode 1156a may be disposed in a direction vertical to the rear parts 114a and 114b. The electrode groove 1156b may form a groove portion concave in the guide rail mounting surface 1152 of the rearward protruding member 115 in the forward direction. At the center of the electrode groove 1156b, an electrode 1156a may be disposed. The electrode groove 1156b may have a cylindrical shape forming a predetermined space around the electrode 1156a.

The electrode 1156a may be disposed such that a portion thereof is exposed rearward of the electrode groove 1156b. The electrode 1156a may be disposed in the electrode groove 1156b of the rearward protruding member 115 and the electrode hole 116c of the guide rail 116. The electrode 1156 may protrude rearward of the electrode groove 1156b within a distance so as to not contact a power line disposed in the guide groove 116a of the guide rail 116. A length H1 by which the electrode 1156a is exposed rearward of the electrode groove 1156b may be less than or equal to a depth H2 of the electrode hole 116c.

<Filter Assembly-Filter Mounting Member>

Hereinafter, a filter mounting member will be described with reference to FIGS. 6, 10 to 12, and 22 to 23. A filter Assembly VI may include a plurality of filter mounting members 61a and 61b according to an embodiment of the invention.

Filter mounting members 61a and 61b may be mounted to filter modules 62a, 62b, 62c, and 62d on one side, and connected to an upper cabinet 11 via mobile members 631a 631b, 632a, and 632b on the other side. The filter mounting member 61a 61b may change the position of the filter modules 62a, 62b, 62c, and 62d. The filter mounting members 61a and 61b may include: a first filter mounting member 61a disposed on the rear left side of the upper cabinet 11, and a second filter mounting member 61b disposed on the rear right side of the upper cabinet 11.

Each of the first filter mounting member 61a and the second filter mounting member 61b may include: a plurality of filter module mount 611a, 611b, 611c, and 611d where which a plurality of filter modules 62a, 62b, 62c, and 62d are respectively inserted and mounted; and a plurality of mobile member fastener 612a, 612b, 612c, and 612d to which a plurality of mobile members 631a, 631b, 632a, and 632b are respectively fastened. Each of the first filter mounting member 61a and the second filter mounting member 61b may further include a first guide member fastener 613a and a second guide member fastener 613b respectively fastened to a first guide member 64a and a second guide member 64b.

The plurality of filter module mounts 611a, 611b, 611c, and 611d may be formed on rear surfaces of the filter mounting members 61a and 61b. In this case, a forward direction and a rearward direction may be set with reference to the case where the filter mounting members 61a and 61b are mounted to the filter mounting member mount bases 117a and 117b. This is merely an example for convenience of explanation, and does not limit the scope of the present invention.

Each of the first filter mounting member 61a and the second filter mounting member 61b may include a plurality of filter module mounts 611a, 611b, 611c, and 611d to receive the plurality of filter modules 62a, 62b, 62c, and 62d, respectively.

The first filter mounting member 61a may include: a first upper filter module mount 611a where the first filter module 62a is inserted and mounted; a first lower filter module mount 611b where the first lower filter module 62b is inserted and mounted; a first upper mobile member fastener 612a to which a first upper mobile member 631a disposed above the first upper filter module mount 611a is fastened; a first lower mobile member fastener 612b to which a first lower mobile member 631b disposed below the first lower filter module mount 611b is fastened; and a first guide member fastener 613a disposed between the first filter module mount 611a and the first lower filter module mount 611b to be fastened to the first guide member 64a.

The second filter mounting member 61b may include: a second upper filter module mount 611c where the second filter module 62c is inserted and mounted; a second lower filter module mount 611d where the second lower filter module 62d is inserted and mounted; a second upper mobile member fastener 612c to which a second upper mobile member 631c disposed above the second upper filter module mount 611c is fastened; a second lower mobile member fastener 612d to which a second lower mobile member 631d disposed below the second lower filter module mount 611d is fastened; and a second guide member fastener 613b disposed between the second filter module mount 611c and the second lower filter module mount 611c to be fastened to the second guide member 64b.

Each of the plurality of filter module mounts 611a, 611b, 611c, and 611d may include: a guide part guiding the filter modules 62a, 62b, 62c, and 62d to be inserted and drawn; a communication hole surface 6113 on which a communication hole 6113a being open in a direction toward a suction port 1143 is formed; and an insertion surface 6114 in which an insertion portion is formed in a direction in which the filter modules 62a, 62b, 62c, and 62d is inserted.

The guide part 6111 and 6112 may be disposed above and below the filter module mount 611a, 611b, 611c, and 611d. The guide part 6111 and 6112 may guide upper ends and lower ends of the filter modules 62a, 62b, 62c, and 62d being inserted or drawn. The guide part 6111 and 6112 may be disposed above and below the filter module mounts 611a, 611b, 611c, and 611d. The guide part 6111 and 6112 may include: a guide rib 6111 protruding to guide the filter modules 62a, 62b, 62c, and 62d to be inserted or drawn; and a guide roller 6112 allowing the filter modules 62a, 62b, 62c, and 62d to be easily inserted or drawn.

The guide rib 6111 may protrude downward from an upper surface of the filter module mount 611a, 611b, 611c, and 611d or may protrude upward from a lower surface of the filter module mount 611a, 611b, 611c, and 611d. The guide rib 6111 may be elongated in a direction in which the filter modules 62a, 62b, 62c, and 62d are inserted. The guide rib 6111 may be spaced apart from the communication hole surface 6113 by a predetermined distance. Part of the filter modules 62a, 62b, 62c, and 62d may be inserted into a space between the guide rib 6111 and the communication hole surface 6113.

The guide rib 6111 may include: an upper guide rib 6111 protruding downward from the upper surface of the filter module mount 611a, 611b, 611c, and 611d; and a lower guide rib 6111 protruding upward from the lower surface of the filter module mount 611a, 611b, 611c, and 611d.

An upper guide groove (not shown) may be formed between the upper guide rib 6111 and the communication hole surface 6113. An upper banding portion 62214a and an upper cover rib 62411 of the filter modules 62a, 62b, 62c, and 62d, which will be described later, may be inserted into the upper guide groove. A lower guide groove 6113b may be formed between the lower guide rib 6111 and the communication hole surface 6113. A lower bending portion 62215a and a lower cover rib 62412 of the filter module, which will be described later, may be inserted into the lower guide groove 6113b.

The guide roller 6112 may be disposed on the filter mounting members 61a and 61b so as to come into contact with the upper surfaces and the lower surfaces of the filter modules 62a, 62b, 62c, and 62d. The guide roller 6112 may include: an upper guide roller 6112 is rotatably mounted to upper portions of the filter module mount 611a, 611b, 611c, and 611d so as to come into contact with upper portions of the filter modules 62a, 62b, 62c, and 62d; and a lower guide roller 6112 rotatably mounted to lower portions of the filter module mount 611a, 611b, 611c, and 611d so as to come into contact with lower portions of the filter modules 62a, 62b, 62c, and 62d.

The guide rib 6111 may be disposed closer to the communication hole surface 6113 than to the guide roller 6112. The guide roller 6112 may be disposed at a start portion at which the filter modules 62a, 62b, 62c, and 62d start to be inserted.

A plurality of communication holes 6113a allowing the inside of the upper cabinet 11 and the filter modules 62a, 62b, 62c, and 62d to communicate with each other may be formed in the communication hole surface 6113. The plurality of communication holes 6113a may be formed in a shape corresponding to a plurality of suction ports formed in a rear parts 114a and 114b of the upper cabinet 11. The plurality of communication holes 6113a may be disposed at positions corresponding to the plurality of suction ports 1143 when the filter mounting members 61a and 61b are mounted to the filter mounting member mount bases 117a and 117b.

A power terminal hole 614a may be formed in the filter mount members 61a and 61b at a portion corresponding to a position of a power terminal 1154. A ground terminal hole 615 may be formed in the filter mounting members 61a and 61b at a portion corresponding to a position of a ground terminal 1155. When the filter mounting members 61a and 61b are mounted to the upper cabinet 11, the power terminal 1154 and a power receiving terminal 6233 may be brought into contact with each other via the power terminal hole 614. When the filter mounting members 61a and 61b are mounted to the upper cabinet 11, the ground terminal 1155 and a ground receiving terminal 6234 may be brought into contact with each other via the ground terminal hole 615. The power terminal hole 614 and the ground terminal hole 615 may be formed in the insertion surface 6114 of the filter mounting members 61a and 61b.

A filter module recognition sensor hole 617 may be formed in the filter mounting members 61a and 61b at a portion corresponding to a filter module recognition sensor 1158 disposed in the upper cabinet 11. When the filter mounting members 61a and 61b are mounted to a rear of the upper cabinet 11, the filter module recognition sensor 1153 may protrude to the outside through the filter module recognition sensor hole 617.

Thus, when the filter mounting members 61a and 61b with the filter modules 62a, 62b, 62c, and 62d mounted thereto are mounted to the rear of the upper cabinet 11, inner portions of the filter modules 62a, 62b, 62c, and 62d may press the filter module recognition sensor 1163 protruding through the filter module recognition sensor hole 617. In this case, the filter module recognition sensor 1153 may detect that the filter mounting members 61*a* and 61*b* with the filter modules 62*a*, 62*b*, 62*c*, and 62*d* mounted thereto is mounted to the rear of the upper cabinet 11. The filter module recognition sensor hole 617 and the filter mounting members 61*a* and 61*b* may be formed in the insertion surface 6114.

A mounting protrusion groove 618 may be formed in the filter mounting members 61*a* and 61*b* at a portion corresponding to a mounting protrusion 1158. When the filter mounting members 61*a* and 61*b* are mounted to the rear of the upper cabinet 11, the mounting protrusion 1158 may be inserted into the mounting protrusion groove 618, thereby maintaining the position of the filter mounting members 61*a* and 61*b*. The mounting protrusion 618 may be formed at a portion where the insertion surface 6114 and the communication hole surface 6113 are in contact with each other.

A short circuit protrusion 616 for turning off a short circuit switch 6235 installed at the filer modules 62*a*, 62*b*, 62*c*, and 62*d* to prevent a short circuit may be disposed in the filter mounting members 61*a* and 61*b*. When the filter modules 62*a*, 62*b*, 62*c*, and 62*d* are mounted to the filter mounting members 61*a* and 61*b*, the short circuit protrusion 616 presses the short circuit switch 6235 so as to turn off the short circuit switch 6235.

The short circuit protrusion 616 may be disposed at each of the plurality of filter module mounts 611*a*, 611*b*, 611*c*, and 611*d*, and turn off short circuit switches of a plurality of filter modules 62*a*, 62*b*, 62*c*, and 62*d* respectively mounted to the plurality of filter module mounts 611*a*, 611*b*, 611*c*, and 611*d*. The short circuit protrusion 616 may be disposed on the insertion surface 6114 of the filter mounting member.

The mobile member fastener 612*a*, 612*b*, 612*c*, and 612*d* may be disposed on front surfaces of the filter mounting members 61*a* and 61*b*. A portion of the mobile member 631*a*, 631*b*, 632*a*, and 632*b* may be fastened to the mobile member fastener 612*a*, 612*b*, 612*c*, and 612*d*. The mobile member fastener 612*a*, 612*b*, 612*c*, and 612*d* may be disposed above or below the filter module mount 611*a*, 611*b*, 611*c*, and 611*d*.

The mobile member fastener 612*a*, 612*b*, 612*c*, and 612*d* may be disposed on the upper sides and the lower sides of the filter mount members 61*a* and 61*b*.

The mobile member fastener 612*a*, 612*b*, 612*c*, and 612*d* may include: a first upper mobile member fastener 612*a* disposed above the first upper filter module mount 611*a* and fastened to the upper mobile member 631*a*; a first lower mobile member fastener 612*b* disposed below the first lower filter module mount 611*b* and fastened to the first lower mobile member 631*b*; a second upper mobile member fastener 612*c* disposed above the second upper filter module mount 611*c* and fastened to the second upper mobile member 632*a*; and a second lower mobile member fastener 612*d* disposed below the second lower filter module mount 611*d* and fastened to the second lower mobile member 632*b*.

Each of the first upper mobile member fastener 612*a* and the second upper mobile member fastener 612*c* may be open in a forward direction and include: a mobile member receiving space 612*s* which forms a space where the first mobile member 631*a* is disposed when the first filter mounting member 64*a* is mounted to the upper cabinet 11; a mobile member fastening surface 6121 to which part of the mobile member 631*a* is coupled; a rearward protruding member opposing surface 6122 which is bent at one side end of the mobile member fastening surface 6121 to extend, and which is disposed to oppose a first protruding surface 1151*a* of the rearward protruding member 115 when the first filter mounting member 61*a* is mounted to the upper cabinet 11; an outer cover surface 6123 which is bent at the other side end of the mobile member fastening surface 6121 to extend; and a partition 6124 which separates the mobile member receiving space 612*a* and the first upper filter module mount 611*a*.

Each of the first lower mobile member fastener 612*a* and the second lower mobile member fastener 612*d* may have elements performing the same functions of the mobile member receiving space 612*s*, the mobile member fastening surface 6121, the rearward protruding member opposing surface 6122, and the outer cover surface 6123. However, because each of the first lower mobile member fastener 612*a* and the second lower mobile member fastener 612*d* are disposed below the first lower filter module mount 611*b* and the second lower filter module mount 611*d*, a partition (not shown) included in each of the first lower mobile member fastener 612*a* and the second lower mobile member fastener 612*d* may be disposed above the mobile member receiving space 612*s*.

The mobile member fastener 612*a*, 612*b*, 612*c*, and 612*d* may be open in a forward direction, and forms a space where the mobile members 631*a* 631*b*, 632*a*, and 632*b* are disposed. The mobile member fastener 612*a*, 612*b*, 612*c*, and 612*d* includes the mobile member fastening surface 6121 to which part of the mobile members 631*a* 631*b*, 632*a*, and 632*b* are coupled. The mobile member fastening surface 6121 may be disposed to be brought into contact with an upper cover 62212 or a lower cover 62213 of a filter case 622 when the filter modules 62*a*, 62*b*, 62*c*, and 62*d* are mounted to the filter mounting members 61*a* and 61*b*.

Each of the first guide member fastener 613*a* and the second guide member fastener 613*b* may be disposed between a plurality of filter module mounts 611*a*, 611*b*, 611*c*, and 611*d* disposed in upward and downward directions. The first guide member fastener 613*a* may be disposed between the first upper filter module mount 611*a* and the first lower filter module mount 611*b* and coupled to the first guide member 64*a*. The second guide member fastener 613*b* may be disposed between the second upper filter module mount 611*c* and the second lower filter module mount 611*d* and fastened to the second guide member 64*b*.

Each of the first guide member fastener 613*a* and the second guide member fastener 613*b* may be open in a forward direction, and forms a space where the first guide member 62*a* or the second guide member 62*b* is disposed. Each of the first guide member fastener 613*a* and the second guide member fastener 613*b* includes the guide member fastening surface 6131 to which part of the first guide member 62*a* or part of the second guide member 64*b* is fastened. The guide member fastening surface 6131 may be disposed to be brought into contact with the upper cover 62212 or the lower cover 62213 of the filter case 622 when the filter modules 62*a*, 62*b*, 62*c*, and 62*d* are coupled to the filter mounting members 61*a* and 61*b*.

<Filter Assembly-Filter Module>

Hereinafter, a filter module according to an embodiment of the invention will be described with reference to FIGS. 5, 6, and 13-24.

A filter assembly VI may include a plurality of filter modules 62*a*, 62*b*, 62*c*, and 62*d*. In the following description, a filter module 62 may be applied to all of a first upper filter module 62*a*, a first lower filter module 62*b*, a second upper filter module 62*c*, and a second lower filter module 62*d*. In addition, a filter mounting member 61 may be applied to all of a first filter mounting member 61*a* and a second filter mounting member 61*b*.

Here, the upward, downward, leftward, rightward, forward, and rearward directions are described with reference to the case where the filter module 62 is mounted to the filter mounting member 61 to be disposed in rear of the upper cabinet 11. In addition, an upward and downward direction is defined as a longitudinal direction of the filter module 62, a leftward and rightward direction is defined as a lateral direction of the filter module 62, and a forward and rearward direction is defined as a width direction of the filter module 62.

The filter module 62 is detachably mounted to the filter mounting member. The filter module 62 may filter foreign substances contained air flowing into a suction port 1143. The filter module 62 according may include: a pre-filter 621 to filter large-sized dust from the air flowing into the suction port 1143; a dust collecting filter unit 623 to filter air by collecting air particles ionized by an ionizing unit 1156; and a deodorization filter unit 624 to remove odor from the air.

The filter module 62 may further include a filter case 622 in which the pre-filter is fixed, and to which the dust collecting filter unit 623 and the deodorization filter unit 624 are mounted. With the dust collecting filter unit 623 and the deodorization filter unit 624 mounted thereto, the filter case 622 may be mounted to the filter mounting member 61. A plurality of suction holes may be formed in the filter case 622 in a direction in which the pre-filter 621 is mounted, and the pre-filter 621 is disposed at the plurality of suction holes. The filter case 622 may include a vertical rib 62211*a* and a horizontal rib 62211*b* which are arranged between the plurality of suction holes on a surface where the pre-filter 621 is mounted.

The vertical rib 62211*a* and the horizontal rib 62211*b* may form a grid shape and reinforce of strength of the filter case. The pre-filter 621 may have a mesh shape to filter large-sized foreign substances from air flowing into the filter module 62. The size of the mesh may vary depending on design considerations.

The filter case 622 may include: a rear cover 6221 disposed at a rear when the filter module 62 is disposed in rear of the upper cabinet 11; and a lateral cover 6222 disposed at a side when the filter module 62 is disposed in rear of the upper cabinet 11.

The rear cover 6221 may include: a pre-filter part 62211 to which the pre-filter 621 is mounted; an upper cover 62212 disposed above the pre-filter part 62211 to cover one side of the filter mounting member 61; and the lower cover 62213 disposed below the pre-filter part 62211 to cover the other side of the filter mounting member 61.

The filter case 622 may include: an upper fixing plate 62214 to fix an upper end of the dust collecting filter unit 623 when the dust collecting filter unit 623 is mounted to the filter case 622; and a lower fixing plate 62215 to fix a lower end of the dust collecting filter unit 623 when the dust collecting filter unit 623 is mounted to the filter case 622. When the dust collecting filter unit 623 is mounted to the filter case 622, the dust collecting filter unit 623 may be fixed in the longitudinal direction of the filter module 62. When the deodorization filter unit 624 is mounted to the filter case 622, the upper fixing plate 62214 and the lower fixing plate 62215 limits movement of the deodorization filter unit 624 in the longitudinal direction of the filter module 62.

The upper fixing plate 62214 may be disposed between the pre-filter 62211 and the upper cover 62212. The lower fixing plate 62215 may be disposed between the pre-filter 62211 and the lower cover 62213. The upper fixing plate 62214 and the lower fixing plate 62215 may protrude toward a space formed by the rear cover 6221 and the lateral cover 6222 to position the dust collecting filter unit 623 and the deodorization filter unit 624.

An upper bending portion 62214*a* may be disposed on the upper fixing plate 62214, and has a front end to be brought into contact with the deodorization filter unit 624 and bending upward. A lower bending portion 62215*a* may be disposed on the lower fixing plate 62215, and has a front end to be brought into contact with the deodorization filter unit 624 and bending downward.

A roller rib 62214*b* may be disposed on the upper fixing plate 62214 at a portion where the guide roller 6112 of the filter mounting member 61 moves. The roller rib 62214*b* may protrude upward from the upper fixing plate 62214 so that the filter module 62 is brought into contact with the guide roller 6112 when inserted into or drawn from the filter mounting member 61. When the filter module 62 is mounted to the filter mounting member 61, a movement limiting protrusion 62214*c* may be disposed on one side of the roller rib 62214*b* to limit movement of the filter module 62 in a direction of drawing the filter module 62. The movement limiting protrusion 62214*c* protrudes upward further than the roller rib 62214*b*. The movement limiting protrusion 62214*c* may be disposed such that, when the filter module 62 is mounted to the filter mounting member 61, the movement limiting protrusion 62214*c* is brought into contact with the guide roller 6112 in a direction of drawing the filter module 62.

Similarly to the upper fixing plate 62214*a*, the lower fixing plate 62215*a* may have a roller rail (not shown) and a movement limiting protrusion (not shown) disposed thereon.

The filter case 622 may include: a dust collecting filter fixing protrusion 6223 to fix one side of the dust collecting filter unit 623 when the dust collecting filter unit 623 is mounted to the filter case 622; a magnet 6224 to fix the other side of the dust collecting filter unit 623 when the dust collecting filter unit 623 is mounted to the filter case 622; and a dual fixing protrusion 6225 to fix both the dust collecting filter unit 623 and the deodorization filter unit 624 when the dust collecting filter unit 623 or the deodorization filter unit 624 is mounted to the filter case 622.

The dust collecting filter fixing protrusion 6223 may be disposed on an upper side and a lower side of the lateral cover 6222. One side of the dust collecting filter unit 623 may be provided in a space between the pre-filter part 62211 and the dust collecting filter fixing protrusion 6223.

The magnet 6224 may be disposed on one side of the pre-filter part 62211, and fix the other side of the dust collecting filter unit 623 to the filter case 622 using a magnetic force. In the dust collecting filter unit 623, a magnet may be disposed at a position corresponding to the magnet 6224 disposed in the pre-filter part 62211.

The dual fixing protrusion 6225 may include two fixing protrusions 6225*a* and 6225*b* spaced apart from the pre-filter part 62211 in the width direction by different distances. The dual fixing protrusion 6225 may include: a first fixing protrusion 6225*a* protruding from the lateral cover 6222 to fix one side of the dust collecting filter unit 623; and a second fixing protrusion 6225*b* protruding from the lateral cover 6222 to fix one side of the deodorization filter unit 624.

A distance of the first fixing protrusion 6225*a* from the pre-filter part 62211 in the width direction is less than a distance of the second fixing protrusion 6225*b* from the pre-filter part 62211 in the width direction. The first fixing protrusion 6225*a* and the second fixing protrusion 6225*b* may be connected at an end portion.

The dust collecting filter fixing protrusion 6223, the magnet 6224, and the dual fixing protrusion 6225 of the filter case 622 prevent the dust collecting filter unit 623 and the deodorization filter unit 624 from moving in the width direction of the filter module 62 when the dust collecting filter unit 623 or the deodorization filter unit 624 is mounted to the filter case 622.

A fixing groove 6227 to prevent movement of the dust collecting filter unit 623 in the lateral direction of the filter module 62 may be formed in the filter case 622. When the dust collecting filter unit 623 is mounted to the filter case 622, a rear protrusion 62311 of the dust collecting filter unit 623 may be inserted into the fixing groove 6227.

The filter case 622 may include a handle 6226 disposed on a rear surface of the rear cover 6221. The handle 6226 may be disposed on a lateral side of the rear of the filter case 622 so as to allow a user to easily draw the filter module 62 from the filter mounting member 61.

The dust collecting filter unit 623 may include: a plurality of electrodes 6232*a* and 6232*b* for generating a magnetic field to collect ionized dust particles; and a dust collecting filter case 6231 forming an external appearance of the dust collecting filter unit 623 and forming an inner space where the plurality of electrodes 6232*a* and 6232*b* is disposed. The electrodes 6232*a* and 6232*b* may be formed in a thin plate The electrodes 6232*a* and 6232*b* may include a high voltage electrode 6232*a* to which a relatively high voltage is applied; and a low voltage electrode 6232*b* to which a low voltage is applied compared to the high voltage electrode 6232*a*. A plurality of high voltage electrodes 6232*a* and a plurality of low voltage electrodes 6232*b* may be arranged side by side. The electrodes 6232*a* and 6232*b* are provided in plural to face each other and form a gap therebetween.

The dust collecting filter unit 623 may include a power receiving terminal 6233 and a ground receiving terminal 6234 to be respectively brought into contact with the power terminal 1154 and the ground terminal 1155. The power receiving terminal 6223 may contact the power terminal 1154 to connect power to the dust collecting filter unit 623. Thus, when the power receiving terminal 6233 is in contact with the power terminal 1154, a high voltage may be applied to the dust collecting filter unit 623.

The ground receiving terminal 6234 may contact the ground terminal 1155 to provide a ground to the dust collecting filter unit 623.

The power receiving terminal 6233 and the ground receiving terminal 6234 may be disposed on one side of the dust collecting filter case 6231. The power receiving terminal 6233 and the ground receiving terminal 6234 may be disposed on the same surface of the dust collecting filter case 6231. The power receiving terminal 6233 and the ground receiving terminal 6234 may be disposed in a direction in which the filter module 62 is inserted to the filter mounting member 61.

The dust collecting filter unit 623 may include the short circuit switch 6235 such that the high voltage electrode 6232*a* and the low voltage electrode 6232*b* are short circuited when the short circuit switch 6235 is turned on, and the high voltage electrode 6232*a* and the low voltage electrode 6232*b* are not short circuited when the short circuit switch 6235 is turned off. The short circuit switch 6235 may be turned off in a state in which the filter module 62 with the dust collecting filter unit 623 mounted thereto is positioned in the filter mounting member 61, and the short circuit switch 6235 may be turned on in a state in which the filter module 62 with the dust collecting filter unit 623 mounted thereto is separated from the filter mounting member 61.

When the filter module 62 is separated from the filter mounting member 61, the high voltage electrode 6232*a* and the low voltage electrode 6232*b* may be short circuited, and thus, an electric charge transferred to the dust collecting filter unit 623 may be removed. When the short circuit switch 6235 is released from pressure, the high voltage electrode 6232*a* and the low voltage electrode 6232*b* may be short circuited.

When the filter module 62 is inserted and positioned in the filter mounting member 61, the short circuit between the high voltage electrode 6232*a* and the low voltage electrode 6232*b* may be released, and thus, a charge may be transferred to the dust collecting filter unit 623, thereby generating a magnetic field.

The short circuit switch 6235 may be disposed on one side surface of the dust collecting filter case 6231. The short circuit switch 6235 may be disposed on the same surface as a surface of the dust collecting filter case 6231 on which the power receiving terminal 6233 and the ground receiving terminal 6234 are disposed. The short circuit switch 6235 may be disposed in a direction in which the filter module 62 is inserted into the filter mounting member 61.

A short circuit protrusion 616 pressing the short circuit switch 6235 when the filter module 62 is inserted and positioned in the filter mounting member 61 may be disposed in the filter mounting member 61. The short circuit protrusion 616 may protrude in a direction of drawing the filter module 62.

The dust collecting filter case 6231 may include: a dust collecting filter suction port through which air flows toward an inner space where the electrodes 6232*a* and 6232*b* are disposed; and a dust collecting filter discharge port through which air with foreign substances removed therefrom flows.

The dust collecting filter case 6231 may include a plurality of fixing protrusions 62311, 62312, and 62313 for fixing a position of the dust collecting filter unit 623 when the dust collecting filter unit 623 is mounted to the filter case 622. The dust collecting filter case 622 may include: a rear protrusion 62311 inserted into the fixing groove 6227, formed in the rear cover 6221 of the filter case 622, when the dust collecting filter unit 623 is mounted to the filter case 622; a lateral protrusion 62312 to be brought into contact with the dust collecting filter fixing protrusion 6223 or the first fixing protrusion 6225*a* of the dual fixing protrusion 6225 which is formed on the lateral cover 6222 of the filter case 622; and a front protrusion 62313 protruding forward of the dust collecting filter case 6231 to be brought into contact with an end portion of the deodorization filter unit 624 disposed in front of the dust collecting filter unit 623. The front protrusion 62313 may limit movement of the deodorization filter unit 624, disposed in front of the dust collecting filter unit 623, in the longitudinal direction of the filter module 62.

The dust collecting filter case 6231 may include a dust collecting filter magnet 61314 to fix the dust collecting filter case 6231 to the filter case 622 using a magnetic force together with the magnet 6224 disposed in the filter case 622. The dust collecting filter magnet 61314 may generate a magnetic force even in relation to a magnet 6224 of the deodorization filter unit 624 disposed in front of the dust collecting filter unit 623.

The deodorization filter unit 624 may physically and/or chemically remove odor components from air by coating a porous base with a deodorant photocatalyst. The deodorization filter unit 624 may include: a deodorization filter case 6241 forming an external appearance to be mounted to the filter case 622; and a deodorization filter 6242 supported by the deodorization filter case 6241. The deodorization filter 6242 may be formed by coating a base member having air gaps with a deodorant photocatalyst or may be manufactured by forming air gaps in a member having a photocatalytic property. Such a photocatalyst may include active carbon.

When the filter mounting member 61 with the filter module 62 mounted thereto is disposed in rear of the upper cabinet 11, an inner portion of the deodorization filter unit 624 may press a filter module recognition sensor 1153 disposed in the upper cabinet 11. Accordingly, a protruding structure for pressing the filter module recognition sensor 1153 may be included at the inner portion of the deodorization filter unit 624.

The deodorization filter case 6241 includes: an upper cover rib 62411 covering the upper bending portion 62214a of the upper fixing plate 62214 of the filter case 622; and a lower cover rib 62412 covering the lower bending portion 62215a of the lower fixing plate 62215 of the filter case 622. The lower cover rib 62412 limits movement of the deodorization filter unit 624 in the upward and downward direction of the filter module 62 when the deodorization filter case 6241 is mounted to the filter case 622.

The deodorization filter case 6241 may further include an outer fixing rib 62413 and 62414 protruding toward the lateral cover 6222 to fix the deodorization filter 6242 to the filter case 622. The outer fixing rib 62413 and 62414 is disposed on one side surface of the deodorization filter case 6241 opposing the lateral cover 6222. The outer fixing rib 62413 and 62414 may include: a first outer fixing rib 62413 formed at a front end of the deodorization filter case 6241; and a second outer fixing rib 62414 spaced apart from the first outer fixing rib 62413 by a predetermined distance in the width direction of the filter module 62. When the deodorization filter unit 624 is mounted to the filter case 622, the first outer fixing rib 62413 and the second outer fixing rib 62414 may be disposed on both sides of the second fixing protrusion 6225b of the dual fixing protrusion 6225 to limit movement of the deodorization filter unit 624 in the width direction of the filter module 62. The first outer fixing rib 62413 may extend from the upper end of the deodorization filter case 6241 to the lower end of the deodorization filter case 6241 in the longitudinal direction. The second outer fixing rib 62414 may be formed on one side of the deodorization filter case 6241 at a position where the second fixing protrusion 6225b is formed.

The deodorization filter unit 624 may include a deodorization filter unit magnet 62415 that is fixed to the magnet 61314 of the dust collecting filter unit 623 by a magnetic force. The deodorization filter unit magnet 62415 may be disposed inside the deodorization filter case 6241. The deodorization filter unit magnet 62415 may be disposed inside the deodorization filter case 6241 at a position corresponding to the magnet 61314 of the dust collecting filter unit 623.

The filter module 62 according to the present embodiment may further include an outer cover 625 that covers the exterior of the lateral cover 6222 of the filter case 622.

The outer cover 615 may be mounted to an outer surface of the lateral cover 6222.

<Coupling Relation of Filter Module/Coupling Relation Between Filter Module and Filter Mounting Member>

Hereinafter, a coupling relation of a filter module and a coupling relation between the filter module and a filter mounting member will be described with reference to FIGS. 19 to 23. A filter module 62 described hereinafter may be applied to a first upper filter module 62a, a first lower filter module 62b, a second upper filter module 62c, and a second lower filter module 62d. In addition, a filter mounting member 61 to be coupled to the filter module 62 may be applied to a first filter mounting member 61a and a second filter mounting member 61b.

Here, the upward, downward, leftward, rightward, forward, and rearward directions are described with reference to the case where the filter module 62 is mounted to the filter mounting member 61 to be disposed in rear of the upper cabinet 11. In addition, an upward and downward direction is defined as a longitudinal direction of the filter module 62, a leftward and rightward direction is defined as a lateral direction of the filter module 62, and a forward and rearward direction is defined as a width direction of the filter module 62.

The filter module 62 may be mounted to the filter mounting member 61 when coupling of the filter module 62 is completed. When a dust collecting filter unit 623 and a deodorization filter unit 624 are mounted to a filter case 622, it may be considered that coupling of the filter module 62 is completed.

The filter module 62 may be slidably mounted to the filter mounting member 61. The filter module 62 is slidably mounted to the filter mounting member 61 in a manner in which an upper bending portion 62214a of the filter module 62 and an upper cover rib 62411 are inserted into an upper guide groove formed on an upper side of the filter mounting member 61. The filter module 62 may be slidably mounted to the filter mounting member 61 in a manner in which a lower bending portion 62215a of the filter module 62 and a lower cover rib 62412 62 are inserted into a lower guide groove 6113b formed on a lower side of the filter mounting member 61. The filter module 62 may be inserted into the filter mounting member 61 in the width direction of the lateral direction of the filter module 62 to be mounted thereto.

When the filter module 62 is being mounted to the filter mounting member 61, a movement limiting protrusion 62214c may be disposed on one side of a guide roller 6112, thereby limiting movement of the filter module 62. When the filter module 62 is being mounted to the filter mounting member 61, the movement limiting protrusion 62214c may be disposed on one side of the guide roller 6112 in a direction of drawing the filter module 62. Accordingly, the movement limiting protrusion 62214c may limit movement of the guide roller 6112 in a drawing direction, thereby maintaining a state in which the filter module 62 is mounted to the filter mounting member 61.

When coupling of the filter module 62 is completed, the dust collecting filter unit 623 is disposed between the filter case 622 and the deodorization filter unit 624. When coupling of the filter module 62 is completed, the upper cover rib 62411 of the deodorization filter unit 624 may be disposed to surround the upper bending portion 62214a of the filter case 622. When coupling of the filter module 62 is completed, the upper cover rib 62411 of the deodorization filter unit 624 may be disposed to surround the top and the front of the upper bending portion 62214a of the filter case 622. Likewise, when coupling of the filter module 62 is completed, the lower cover rib 62412 of the deodorization filter unit 624 may be disposed to surround the lower bending portion 62215a of the filter case 622.

When coupling of the filter module 62 is completed, a rear protrusion of the dust collecting filter unit 623 may be inserted into a fixing groove 6227 of the filter case 622. When coupling of the filter module 62 is completed, a front protrusion 62313 of the dust collecting filter unit 623 may be disposed at an end portion of the deodorization filter unit 624. When coupling of the filter module 62 is completed, a lateral protrusion 62312 of the dust collecting filter unit 623 may be disposed to be brought into contact with a dust collecting filter fixing protrusion 6223 formed on a lateral cover 6222 of the filter case 622 or a first fixing protrusion 6225a of a dual fixing protrusion.

When coupling of the filter module 62 is completed, a second fixing protrusion 6225b of the dual fixing protrusion 6225 of the filter case 622 may be disposed between a first outer fixing rib 62413 and a second outer fixing rib 62414 of the deodorization filter unit 624.

When the filter module 62 is mounted to the filter mounting member 61, the upper bending portion 62214a of the filter module 62 and the upper cover rib 62411 are inserted into the upper guide groove formed on the upper side of the filter mounting member 61, and the lower bending portion 62215a of the filter module 62 and the lower cover rib 62412 62 are inserted into the lower guide groove 6113b formed on the lower side of the filter mounting member 61.

When the filter module 62 is mounted to the filter mounting member 61, an upper cover 62212 or a lower cover 62213 of the filter case 622 may cover a mobile member fastening surface 6121 or a guide member fastening surface 6131 of the filter mounting member 61.

<Filter Assembly-Mobile Member/Guide Member>

Hereinafter, a mobile member and a guide member according to an embodiment of the invention will be described with reference to FIGS. 6 and 25 to 33.

Mobile members 631a, 631b, 632a, and 632b according to the present embodiment may be rotatably connected to a cabinet assembly I and filter mounting members 61a and 61b. The mobile members 631a, 631b, 632a, and 632b may position filter modules 62a, 62b, 62c, and 62d mounted to the filter mounting members 61a and 61b at a suction port 1143, or position the filter mounting members 61a and 61b such that a direction of drawing the filter modules 62a, 62b, 62c, and 62d faces forward.

The filter modules 62a, 62b, 62c, and 62d may be inserted into or drawn from the filter mounting members 61a and 61b in the lateral direction of the filter modules. Accordingly, the mobile members 631a, 631b, 632a, and 632b move the filter mounting members 61a and 61b between a first position P1, at which the filter modules 62a, 62b, 62c, and 62d are positioned at the suction port 1143, and a second position P2, at which the filter modules 62a, 62b, 62c, and 62d are positioned with the lateral direction thereof facing forward.

In this case, it is understood that being positioned to face forward may include being positioned vertically in a forward direction, and being positioned to be inclined in a forward direction.

A filter assembly VI according may include: first mobile members 631a and 631b rotatably connected to an upper cabinet 11 and a first filter mounting member 61a, respectively, to move the position of the first filter mounting member 61a; and second mobile members 632a and 632b rotatably connected to the upper cabinet 11 and a second filter mounting member 61b, respectively, to move the position of the second filter mounting member 61b.

The filter assembly VI may include: first driving devices 633a and 633a' respectively pressing the first mobile members 631a and 631b to change the position of the first filter mounting member 61a; and second driving devices 633b and 633b' respectively pressing the second mobile members 632a and 632b to change the position of the second filter mounting member 61b.

Driving devices may include: upper driving devices 633a and 633b respectively pressing a first upper mobile member 631a and a second upper mobile member 632a; and lower driving devices 633a' and 633b' respectively pressing a first lower mobile members 631b and a second lower mobile member 632b.

Driving devices may further include a stepping motor that operates electrically. However, this is merely an example—a solenoid valve operating electrically or a cylinder structure may be used.

The filter assembly VI may include an upper driving device fixing plate 65 to which the first upper driving device 633a and the second upper driving device 633b are mounted. The upper driving device fixing plate 65 may have the first upper driving device 633a and the second upper driving device 633b mounted thereto, and may be fixed to an upper side of the upper cabinet 11.

The filter assembly VI may include a lower driving device fixing plate 66 to which the first lower driving device 633a' and the second lower driving device 633b' are mounted. The lower driving device fixing plate 66 may have the first lower driving device 633a' and the second lower driving device 633b' mounted thereto, and may be fixed to a lower side of the upper cabinet 11.

The first mobile members 631a and 631b and the second mobile members 632a and 632b may extend from the center of the indoor unit in the forward and rearward direction, and may be disposed symmetric with reference to a center line C-C' that divides the indoor unit into left and right sides.

The first mobile members 631a and 631b may include the first upper mobile member 631a disposed in an upper portion of the upper cabinet 11, and the first lower mobile member 631b disposed in a lower portion of the upper cabinet 11. The second mobile members 632a and 632b may include the second upper mobile member 632a disposed in the upper portion of the upper cabinet 11, and the second lower mobile member 632b disposed in the lower portion of the upper cabinet 11.

The first upper mobile member 631a and the second upper mobile members 632a may have the same configuration, and may be disposed symmetric to each other with reference to the center line C-C' that extends from the center of the indoor unit in the forward and rearward direction. In addition, the first lower mobile member 631b and the second lower mobile members 632b may have the same configuration, and may be disposed symmetric to each other with reference to the center line C-C' that extends from the center of the indoor unit in the forward and rearward direction Hereinafter, the first upper mobile member 631a and the second mobile member 632a will be described with reference to FIGS. 26 to 30.

Each of the first upper mobile member 631a and the second upper mobile member 632a may include: dual links 634a, 634b, 635a, and 635b having different lengths and rotatably connected to the filter mounting members 61a and 61b; and drive transmission links 636a, 636b, 637a, and 637b transferring driving forces of the driving devices 633a and 633b to the dual links 634a, 634b, 635a, and 635b. The first upper mobile member 631a and the second upper mobile member 632a may further include: cabinet fixing frames 638a and 638b fixed to the upper cabinet 11 and rotatably connected to the dual links 634a, 634b, 635a, and 635b; and filter mounting member connection frames 639a and 639b fixed to the filter mounting members 61a and 61b and rotatably connected to the dual links 634a, 634b, 635a, and 635b.

Two links included in the dual links 634a, 634b, 635a, and 635b are rotatably connected to the cabinet fixing frames 638a and 638b and the filter mounting member connection frames 639a and 639b Accordingly, if one link rotates, the other link may rotate as well.

The dual links 634a, 634b, 635a, and 635b may include: first links 634a and 634b rotatably connected to the cabinet fixing frames 638a and 638b and the filter mounting member connection frames 639a and 639b and connected to the drive transmission links 636a, 636b, 637a, and 637b; and second links 635a and 635b spaced apart from the first links 634a and 634b and rotatably connected to the cabinet fixing frames 638a and 638b and the filter mounting member connection frames 639a and 639b.

The first links 634a and 634b have a length that is longer than a length of the second links 635a and 635b. The first links 634a and 634b are disposed closer to the middle portion of the upper cabinet 11, by which the upper cabinet 11 is divided into left and right sides, than the second links 635a and 635b are.

The first links 634a and 634b may include: first connection frame couplers 6341a and 6341b rotatably connected to the filter mounting member connection frames 639a and 639b; first fixing frame couplers 6342a and 6342b rotatably connected to the cabinet fixing frames 638a and 638b; first link bars 6343a and 6343b connecting the first connection frame couplers 6341a and 6341b and the first fixing frame couplers 6342a and 6342b; and transmission link connection parts 6344a and 6344b formed in the first link bars 6343a and 6343b and rotatably connected to the drive transmission links 636a, 636b, 637a, and 637b.

The first links 634a and 634b may be rotatably coupled to the filter mounting member connection frames 639a and 639b with reference to first link-first hinge shafts 6341ah and 6341bh that are formed in the first connection frame couplers 6341a and 6341b. The first links 634a and 634b may be rotatably coupled to the cabinet fixing frames 638a and 638b with reference to first link-second hinge shafts 6342ah and 6342bh that are formed in the first fixing frame couplers 6342a and 6342b.

The transmission link connection parts 6344a and 6344b may be disposed adjacent to the first fixing frame couplers 6342a and 6342b.

The second links 635a and 635b may include: second connection frame couplers 6351a and 6351b rotatably connected to the filter mounting member connection frames 639a and 639b; second fixing frame couplers 6352a and 6352b rotatably connected to the cabinet fixing frames 638a and 638b; and second link bars 6353a and 6353b connecting the second connection frame couplers 6351a and 6351b and the second fixing frame couplers 6352a and 6352b.

The second links 635a and 635b may be rotatably coupled to the filter mounting member connection frames 639a and 639b with reference to second link-first hinge shafts 6351ah and 6351bh that are formed in the first connection frame couplers 6341a and 6341b. The second links 635a and 635b may be rotatably coupled to the cabinet fixing frames 638a and 638b with reference to second link-second hinge shafts 6352ah and 6352bh that are formed in the second fixing frame couplers 6352a and 6352b. A length of the first links 634a and 634b is longer than a length of the second links 635a and 635b. The first links 634a and 634b may be disposed at an inner side relative to the second links 635a and 635b. A gap G1 between the first connection frame couplers 6241 and 6241b, corresponding to one ends of the first links 634a and 634b, and the second connection frame couplers 6351a and 6351b, corresponding to one ends of the second links 635a and 635b, is greater than a gap G2 between the first fixing frame couplers 6342a and 6342b, corresponding to the other ends of the first links 634a and 634b, and the second fixing frame couplers 6352a and 6352b, corresponding to the other ends of the second links 635a and 635b.

Thus, when the first links 634a and 634b rotates by a predetermined angle in a wide range, the second links 635a and 635b may rotate by an angle greater than the angle of rotation of the first links 634a and 634b and in a range narrower than the range of rotation of the first links 634a and 634b.

The drive transmission links 636a, 636b, 637a, and 637b may be connected to the driving devices 633a and 633b to transfer driving forces of the driving devices 633a and 633b to the first links 634a and 634b. The drive transmission links 636a, 636b, 637a, and 637b may include: motor links 636a and 636b fixedly connected to the driving devices 633a and 633b; and bending links 637a and 637b rotatably connected to the motor links 636a and 636b at one ends and connected to the first links 634a and 634b at the other ends.

The motor links 636 and 636b may be fixedly connected to the driving devices 633a and 633b at one end, and rotatably connected to the bending links 637a and 637b at the other end. The motor links 636a and 636b may include: motor fixing parts 6361a and 6361b fixedly connected to the driving devices 633a and 633b; bending link connecting parts 6362a and 6362b rotatably connected to the bending links 637a and 637b; and motor link bars 6363a and 6363b connecting the motor fixing parts 6361a and 6361b and the bending link connecting parts 6362a and 6362b.

In the motor fixing parts 6361a and 6361b, polygonal shaped fixing grooves 6361ah and 6361bh may be formed at a portion to be fastened to the driving devices 633a and 633b. Since the motor links 636a and 636b is connected to the driving devices 633a and 633b through the fixing grooves 6361ah and 6361bh, the motor links 636a and 636b may be fixedly connected to the driving devices 633a and 633b.

Since the motor links 636a and 636b are fixedly connected to the driving devices 633a and 633b at one end, the motor link bars 6363a and 6363b rotate on the motor fixing parts 6361a and 6361b when the driving devices 633a and 633b are operated. When the driving devices 633a and 633b are operated, the bending link connecting parts 6362a and 6362b of the motor links 636a and 636b rotate with a radius corresponding to the motor link bars 6363a and 6363b. Accordingly, when the driving devices 633a and 633b are operated, the bending links 637a and 637b rotatably connected to the bending link connecting parts 6362a and 6362b move.

The bending links 637a and 637b may have a bent shape of "⌐". The bending links 637a and 637b include: motor link connecting parts 6371a and 6371b rotatably connected to the motor links 636a and 636b; dual link connecting parts 6372a and 6372b rotatably connected to the first links 634a and 634b of the dual links 634a, 634b, 635a, and 635b; and bending link bars 6373a and 6373b having the bending portions 6374a and 6374b and connecting the motor link connecting parts 6371a and 6371b and the dual link connecting parts 6372a and 6372b. The bending portions 6374a and 6374b may have a vertically bent shape. The bending portions 6374a and 6374b are disposed closer to the motor link connecting parts 6371a and 6371b than the dual link connecting parts 6372a and 6372b. In this case, the bending portion having a vertically bent shape may include a shape perfectly vertical or a shape approximately vertical in a range between 80° and 100°.

The bending links 637a and 637b may be rotatably coupled to the motor links 636a and 636b with reference to bending link-first hinge shafts 6371ah and 6371bh that are formed in the motor link connecting parts 6371a and 6371b. The bending links 637a and 637b may be coupled to the first links 634a and 634b with reference to bending link-second hinge shafts 6372ah and 6372bh that are formed in the dual link connecting parts 6372a and 6372b.

The cabinet fixing frames 638a and 638b may be fastened to the mobile member fixing part 1141 formed in the rear parts 114a and 114b of the upper cabinet 11. The cabinet fixing frames 638a and 638b may be inserted into the mobile member fixing part 1141 to be fixed to an additional fastening member (not shown). Fastening holes 6381a and 6381b into which the additional fastening member is inserted may be formed in the cabinet fixing frames 638a and 638b. Since the cabinet fixing frames 638a and 638b are fixed to the upper cabinet 11, the cabinet fixing frames 638a and 638b are prevented from moving even when the driving devices 633a and 633b are operated.

Thus, the position of the first link-second hinge shafts 6342ah and 6342bh formed between the cabinet fixing frames 638a and 638b and the first links 634a and 634b remain fixed even when the driving devices 633a and 633b are operated. In addition, the position of the second link-second hinge shafts 6352ah and 6352bh formed between the cabinet fixing frames 638a and 638b and the second links 635a and 635b remain fixed even when the driving devices 633a and 633b are operated.

The cabinet fixing frames 638a and 638b may be rotatably connected to the dual links 634a, 634b, 635a, and 635b. The cabinet fixing frames 638a and 638b may be rotatably connected to the first links 634a and 634b, and rotatably connected to the second links 635a and 635b. The cabinet fixing frames 638a and 638b may be disposed on an outer side of the rear parts 114a and 114b of the upper cabinet 11. In this case, the outer side may indicate a direction distal from the center line. When the filter mounting members 61a and 61b are disposed in rear of the upper cabinet 11, the cabinet fixing frames 638a and 638b may be disposed at a distance far from the center line than the filter mounting member connection frames 639a and 639b.

The filter mounting member connection frames 639a and 639b may be fastened to the mobile member fastener 611a and 611c of the filter mounting members 61a and 61b. The filter mounting member connection frames 639a and 639b may be fixed to the filter mounting members 61a and 61b and rotatably connected to the dual links 634a, 634b, 635a, and 635b. Thus, when the dual links 634a, 634b, 635a, and 635b move, the filter mounting member connection frames 639a and 639b may move the filter mounting members 61a and 61b.

The filter mounting member connection frames 639a and 639b may include filter mounting member fasteners 6391a and 6391b that are fastened to the filter mounting members 61a and 61b. The filter mounting member fasteners 6391a and 6391b may be formed on both ends of the filter mounting member connection frames 639a and 639b, and connected to the filter mounting members 61a and 61b via an separate fastening member (not shown).

The position of the first link-first hinge shafts 6341ah and 6341bh formed between the filter mounting member connection frames 639a and 639b and the first links 634a and 634b changes when the driving devices 633a and 633b are operated. In addition, the position of the second link-first hinge shafts 6351ah and 6351bh formed between the filter mounting member connection frames 639a and 639b and the second links 635a and 635b changes when the driving devices 633a and 633b are operated. The position of the filter mounting member connection frames 639a and 639b may change in response to change in position of the first link-first hinge shafts 6341ah and 6341bh and the second link-first hinge shafts 6351ah and 6351bh.

The filter mounting member connection frames 639a and 639b may be rotatably connected to the dual links 634a, 634b, 635a, and 635b. The filter mounting member connection frames 639a and 639b may be rotatably connected to the first links 634a and 634b, and rotatably connected to the second links 635a and 635b. When the filter mounting members 61a and 61b are disposed in rear of the upper cabinet 11, the filter mounting member connection frames 639a and 639b may be disposed at a distance closer to the center line than the cabinet fixing frames 638a and 638b.

Figure 31:
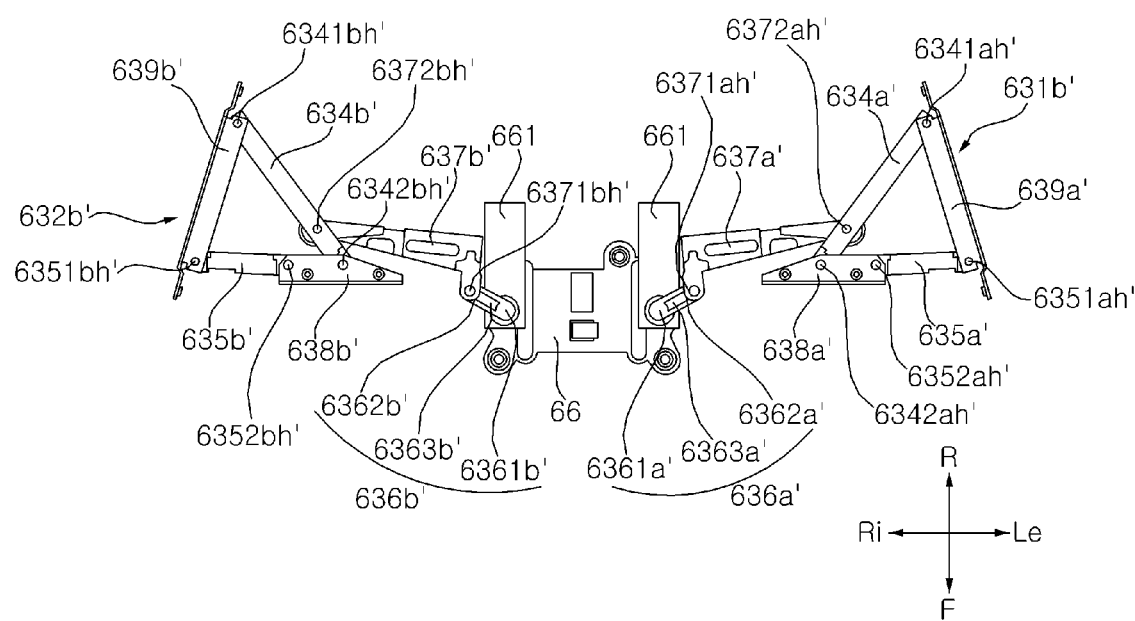
FIG. 31 is a plan view of a first lower mobile member, a second lower mobile member, and a lower driving device fixing plate according to an embodiment of the present invention.
Figure 32:
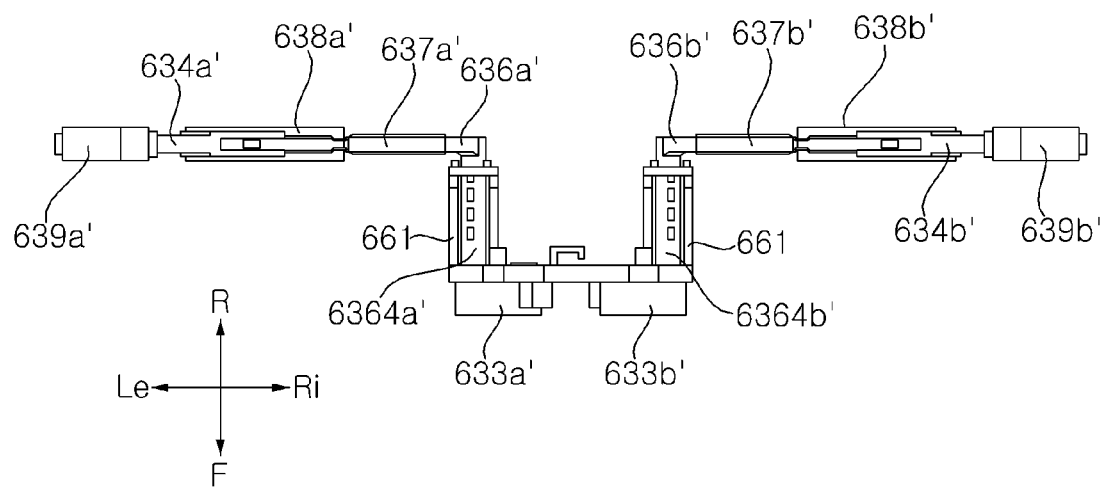
FIG. 32 is a rear view of a first lower mobile member, a second lower mobile member, and a lower driving device fixing plate according to an embodiment of the present invention.

Hereinafter, the first lower mobile member 631b and the second lower mobile member 632 will be described primarily about difference from the first upper mobile member 631a and the second upper mobile member 632a, with reference to FIGS. 31 and 32.

Each of the first lower mobile member 631b and the second lower mobile member 632b may include: dual links 634a', 634b', 635a', and 635b' having different lengths and rotatably connected to the upper cabinet 11 and the filter mounting members 61a and 61b; drive transmission links 636a', 636b', 637a', and 637b' transferring rotational forces of driving devices 633a' and 633b' to the dual links 634a', 634b', 635a', and 635b'; cabinet fixing frames 638a' and 638b' fixed to the upper cabinet 11 and rotatably connected to the dual links 634a', 634b', 635a', and 635b'; and filter mounting member connection frames 639a' and 639b' fixed to the filter mounting members 61a and 61b and rotatably connected to the dual links 634a', 634b', 635a', and 635b'.

The dual links 634a', 634b', 635a', and 635b' may include: first links 634a' and 634b' rotatably connected to the cabinet fixing frames 638a' and 638b' and the filter mounting member connection frames 639a' and 639b' and connected to the drive transmission links 636a', 636b', 637a' and 637b'; and a second links 635a' and 635b' spaced apart from the first links 634a' and 634b' and rotatably connected to the cabinet fixing frames 638a' and 638b' and the filter mounting member connection frames 639a' and 639b'.

The first links 634a' and 634b' may be rotatably coupled to the filter mounting member connection frames 639a' and 639b' with reference to first link-first hinge shafts 6341ah' and 6341bh', and may be rotatably connected to the cabinet fixing frames 638a' and 638b' with reference to first link-second hinge shafts 6342ah' and 6342bh'. The second links 635a' and 635b' may be rotatably coupled to the filter mounting member connection frames 639a' and 639b' with reference to second link-first hinge shafts 6351ah' and 6351bh', and may be rotatably coupled to the cabinet fixing frames 638a' and 638b' with reference to second link-second hinge shafts 6352ah' and 6352bh'.

The drive transmission links 636a', 636b', 637a' and 637b' may include: a motor links 636a' and 636b' fixedly connected to the driving devices 633a' and 633b'; and a bending links 637a' and 637b' rotatably connected to the motor links 636a' and 636b' at one end and connected to the first links 634a' and 634b' at the other end.

The bending links 637a and 637b may be rotatably coupled to the motor links 636a' and 636b' with reference to bending link-first hinge shafts 6371ah' and 6371bh', and may be rotatably connected to the first links 634*a*' and 634*b*' with reference to bending link-second hinge shafts 6372*ah*' and 6372*bh*'.

The motor links 636*a*' and 636*b*' may include: a motor fixing parts 6361*a* 'and 6361*b*' fixedly connected to the driving devices 633*a*' and 633*b*'; bending link connecting parts 6362*a*' and 6362*b*' rotatably connected to the bending links 637*a*' and 637*b*'; motor link bars 6363*a*' and 6363*b*' connecting the motor fixing parts 6361*a*' and 6361*b*' and the bending link connecting parts 6362*a*' and 6362*b*'; and vertical link bars 6364*a*' and 6364*b*' extending vertically from the motor fixing parts 6361*a*' and 6361*b*' that are formed at end portions of the motor link bars 6363*a*' and 6363*b*'.

The vertical link bars 6364*a*' and 6364*b*' may transfer rotational forces generated by the driving devices 633*a*' and 633*b*' to the motor fixing parts 6361*a*' and 6361*b*' to rotate the motor link bars 6363*a*' and 6363*b*' in a clockwise direction or a counter-clockwise direction. In consideration of the lower structure of the upper cabinet 11 and arrangement of the driving devices 633*a*' and 633*b*', the shape of the vertical link bars 6364*a*' and 6364*b*' may be elongated downward. The vertical link bars 6364*a*' and 6364*b*' may be elongated along a rotational axis of the motor links 636*a*' and 636*b*'. The lower driving device fixing plate 66 may include a motor fixing part support member 661 that supports the vertical link bars 6364*a*' and 6364*b*'. The motor fixing part support member 661 may form a space where the vertical link bars 6364*a*' and 6364*b*' are rotatably positioned.

Figure 33:
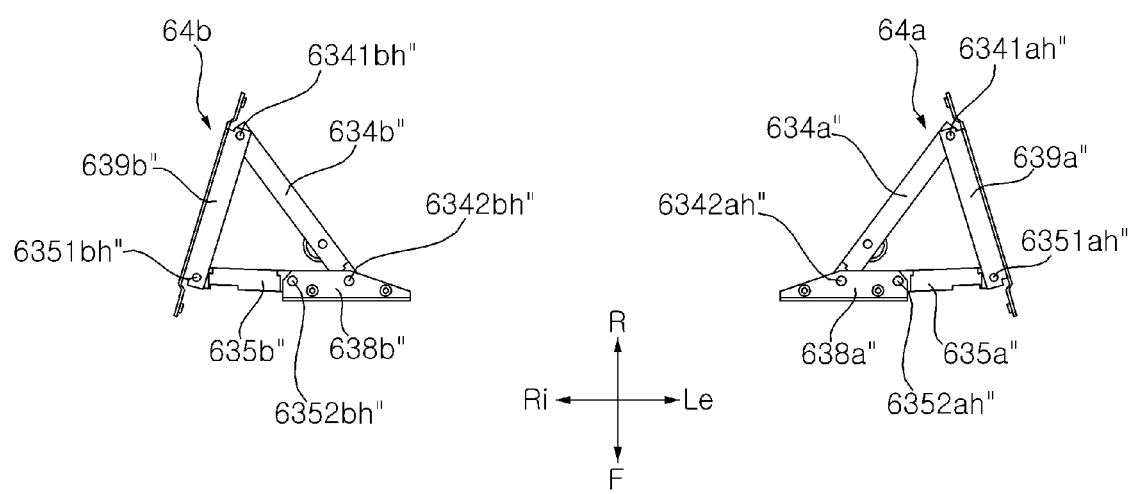
FIG. 33 is a plan view of a first guide member and a second guide member according to an embodiment of the present invention.
Figure 34:
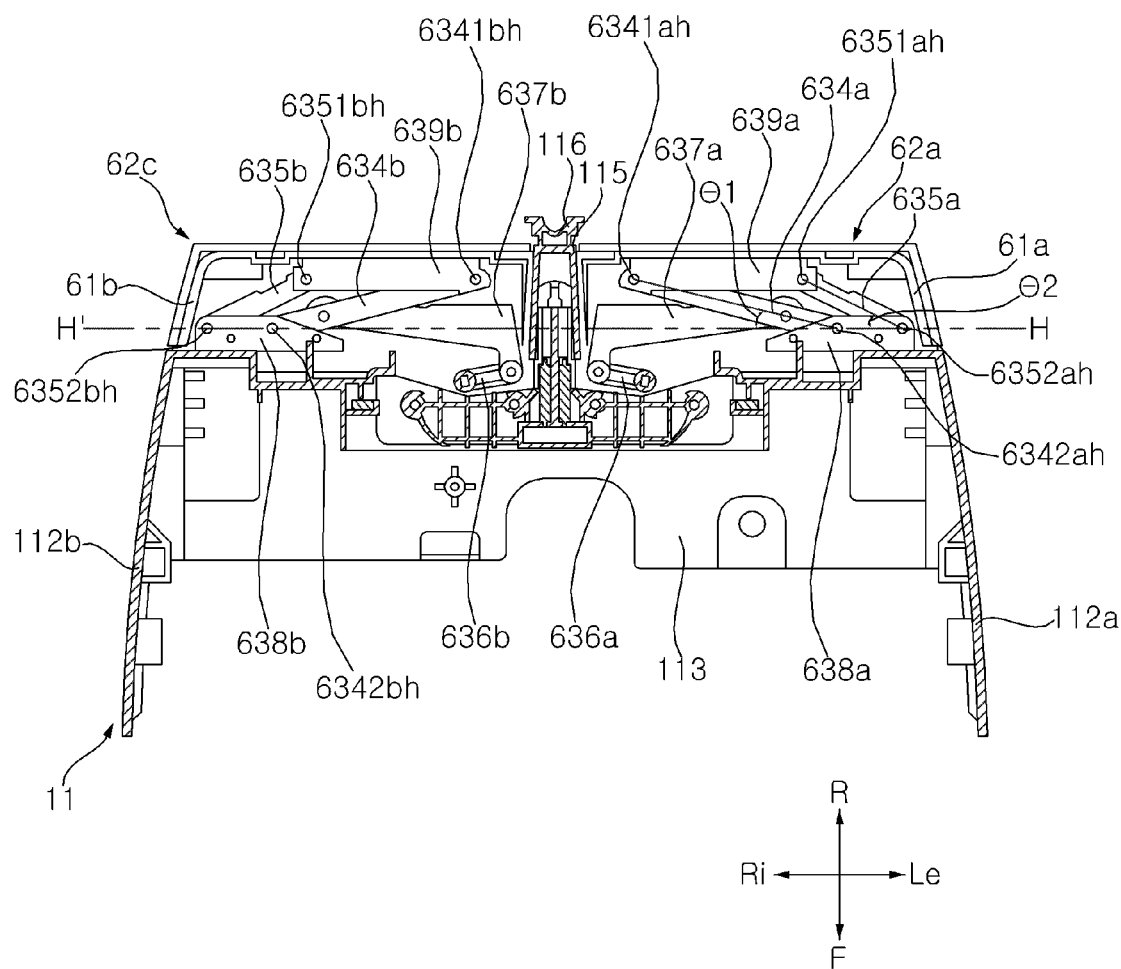
FIG. 34 is a view for explanation of arrangement of a mobile member, a filter mounting member, and a filter module at a first position P1 according to an embodiment of the present invention.
Figure 35:
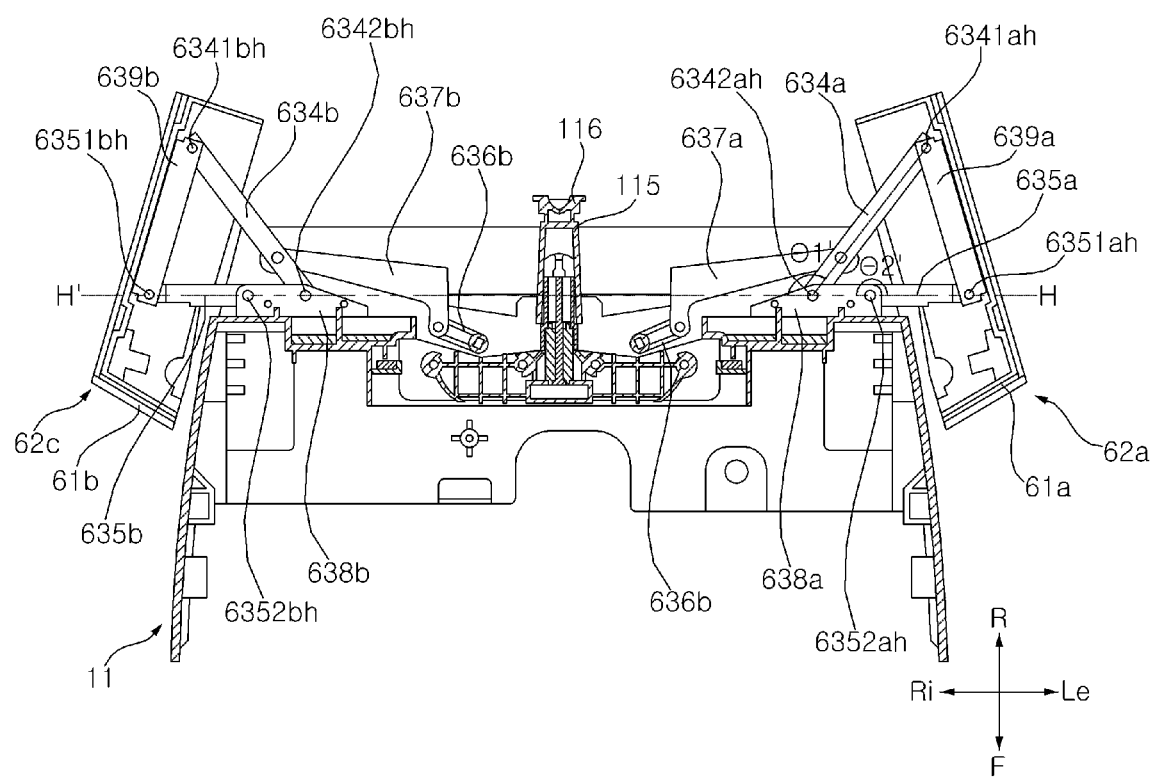
FIG. 35 is a view for explanation of arrangement of a mobile member, a filter mounting member, and a filter module at a second position P2 according to an embodiment of the present invention.

Hereinafter, the first guide member 64*a* and the second guide member 64*b* will be described primarily about difference from the first upper mobile member 631*a* and the second upper mobile member 632*a*, with reference to FIG. 33.

The filter assembly VI may further include a guide members 64*a* and 64*b* that support movement of the filter mounting members 61*a* and 61*b*. The filter assembly VI may include a first guide member 64*a* connected to the first filter mounting member 61*a*, and a second guide member 64*b* connected to the second filter mounting member 61*b*.

The first guide member 64*a* may be fastened to a first guide member fastener 613*a*" of the first filter mounting member 61*a*, and to a first guide member fixing part 1142*a* of the upper cabinet 11. The second guide member 64*b* may be fastened to a second guide member fastener 613*b*" of the second filter mounting member 61*b*, and to a second guide member fixing part 1142*b* of the upper cabinet 11.

The first guide member 64*a* may support the weight of the first filter mounting member 61*a* and the first filter module 62*a* and 62*b*. The second guide member 64*b* may support the weight of the second filter mounting member 61*b* and the second filter module 62*c* and 62*d*.

The first guide member 64*a* and the second guide member 64*b* may include: dual links 634*a*", 634*b*", 635*a*", and 635*b*" having different lengths and rotatably connected to the upper cabinet 11 and the filter mounting members 61*a* and 61*b*; cabinet fixing frames 638*a*" and 638*b*" connected to the upper cabinet 11 and rotatably connected to the upper cabinet 11 and rotatably connected to the dual links 634*a*", 634*b*", 635*a*", and 635*b*"; and filter mounting member connection frames 639*a*" and 639*b*" fixed to the filter mounting members 61*a* and 61*b* and rotatably connected to the dual links 634*a*", 634*b*", 635*a*", and 635*b*".

The dual links 634*a*", 634*b*", 635*a*", and 635*b*" may include: first links 634*a*" and 634*b*" rotatably connected to the cabinet fixing frames 638*a*" and 638*b*" and the filter mounting member connection frames 639*a*" and 639*b*"; and second links 635*a*" and 635*b*" spaced apart from the first links 634*a*" and 634*b*" and rotatably connected to the cabinet fixing frames 638*a*" and 638*b*" and the filter mounting member connection frames 639*a*" and 639*b*".

The first links 634*a*" and 634*b*" may be rotatably coupled to the filter mounting member connection frames 639*a*" and 639*b*" with reference to first link-first hinge shafts 6341*ah*" and 6341*bh*", and rotatably coupled to the cabinet fixing frames 638*a*" and 638*b*" with reference to first link-second hinge shafts 6342*ah*" and 6342*bh*". The second links 635*a*" and 635*b*" are rotatably coupled to the filter mounting member connection frames 639*a*" and 639*b*" with reference to second link-first hinge shafts 6351*ah*" and 6351*bh*", and rotatably coupled to the cabinet fixing frames 638*a*" and 638*b*" with reference to second link-second hinge shafts 6352*ah*" and 6352*bh*".

Each of the first guide member 64*a* and the second guide member 64*b* does not include a separate driving device and a drive transmission link.

<Movement of Mobile Member/Movement of Filter Mounting Member>

Hereinafter, with reference to FIGS. 27, 28, 34, and 35, arrangement of the filter mounting members 61*a* and 61*b* upon movement thereof by the first mobile members 631*a*, 631*b* and the second mobile members 632*a* and 632*b*, and arrangement of the mobile members will be described according to an embodiment of the invention.

The filter mounting members 61*a* and 61*b* and the filter modules 62*a*, 62*b*, 62*c*, and 62*d* may change in position in relation to the upper cabinet 11 by the first mobile members 631 and 631*b* and the second mobile members 632*a* and 632*b*. By the first mobile members 631 and 631*b* and the second mobile members 632*a* and 632*b*, the filter mounting members 61*a* and 61*b* and the filter modules 62*a*, 62*b*, 62*c*, and 62*d* may be positioned at a first position P1 in rear of the upper cabinet 11 or at a second position P2 lateral to the upper cabinet 11.

FIGS. 27, 28, 34, and 35 will be described with reference to movement of the first filter mounting member 61*a* and the second filter mounting member 61*b* in accordance with movement of the first upper mobile member 631*a* and the second upper mobile member 632*a*. When the first upper mobile member 631*a* moves, the first lower mobile member 631*b* and the dual links 634*a*, 634*b*, 635*a*, and 635*b* of the first guide member 64*a* may make the same movement. When the second upper mobile member 632*a* moves, the second lower mobile member 632*b* and the dual links 634*a*, 634*b*, 635*a*, and 635*b* of the second guide member 64*b* may make the same movement.

When the filter mounting members 61*a* and 61*b* and the filter modules 62*a*, 62*b*, 62*c*, and 62*d* are placed at the first position P1, the filter mounting members 61*a* and 61*b* are mounted to the upper cabinet 11. When the filter mounting members 61*a* and 61*b* and the filter modules 62*a*, 62*b*, 62*c*, and 62*d* are placed at the first position P1, air suctioned into the suction port 1143 may pass through the filter modules 62*a*, 62*b*, 62*c*, and 62*d*.

When the filter mounting members 61*a* and 61*b* are placed at the first position P1, the filter mounting member connection frames 639*a* and 639*b* and the cabinet fixing frames 638*a* and 638*b* may be arranged in parallel with each other. When the filter mounting members 61*a* and 61*b* are placed at the first position P1, an angle θ1 formed by a virtual horizontal line H-H', which passes points rotatably connected to the first links 634*a* and 634*b* and points rotatably connected to the second links 635*a* and 635*b* in the cabinet fixing frames 638*a* and 638*b*, and a straight line, which connects the first link-first hinge shafts 6341*ah*,

6341*bh* and the first link-second hinge shafts 6342*ah* and 6342*bh* of the first links 634*a* and 634*b*, (hereinafter, the angle is referred to as an "angle between the horizontal line H-H' and the first links 634*a* and 634*b*") corresponds to an acute angle. When the filter mounting members 61*a* and 61*b* are placed at the first position P1, an angle θ2 formed by the virtual horizontal line and a straight line, which passes the second link-first hinge shafts 6351*ah* and 6351*bh* and the second link-second hinge shafts 6352*ah* and 6352*bh* of the second links 635*a* and 635*b*, (hereinafter, the angle is referred to as an "angle between the horizontal line H-H' and the second links 635*a* and 635*b*) corresponds to an acute angle.

When the filter mounting members 61*a* and 61*b* and the filter modules 62*a*, 62*b*, 62*c*, and 62*d* are placed at the second position, the filter mounting members 61*a* and 61*b* are released from the upper cabinet 11. When the filter mounting members 61*a* and 61*b* and the filter modules 62*a*, 62*b*, 62*c*, and 62*d* are placed at the second position, a user may draw the filter modules 62*a*, 62*b*, 62*c*, and 62*d* from the filter mounting members 61*a* and 61*b* or may mount the filter modules 62*a*, 62*b*, 62*c*, and 62*d* to the filter mounting members 61*a* and 61*b*.

When the filter mounting members 61*a* and 61*b* are placed at the second position P2, the filter mounting member connection frames 639*a* and 639*b* and the cabinet fixing frames 638*a* and 638*b* may be disposed to be inclined with respect to each other. When the filter mounting members 61*a* and 61*b* are placed at the second position P2, an angle θ1' between the virtual horizontal line H-H' and the first links 634*a* and 634*b* corresponds to an obtuse angle. When the filter mounting members 61*a* and 61*b* are placed at the second position P2, an angle θ2' between the virtual horizontal line H-H' and the second links 635*a* and 635*b* corresponds to an approximate straight angle.

When the filter mounting members 61*a* and 61*b* move from the first position P1 to the second position P2, a variation Δθ2 of the angle formed by the virtual horizontal line and the second links 635*a* and 635*b* is greater than a variation of Δθ1 of the angle formed by the virtual horizontal line and the first links 634*a* and 634*b*.

When the filter mounting members 61*a* and 61*b* and the filter modules 62*a*, 62*b*, 62*c*, and 62*d* are placed at the second position, the lateral cover 6222 of the filter modules 62*a*, 62*b*, 62*c*, and 62*d* is disposed to face forward. When the filter mounting members 61*a* and 61*b* and the filter modules 62*a*, 62*b*, 62*c*, and 62*d* are placed at the second position, the filter modules 62*a*, 62*b*, 62*c*, and 62*d* are disposed on an outer side of the lateral parts 112*a* and 112*b* of the upper cabinet 11. When the filter mounting members 61*a* and 61*b* and the filter modules 62*a*, 62*b*, 62*c*, and 62*d* are placed at the second position, the filter mounting member connection frames 639*a* and 639*b* are disposed on outer sides of the lateral parts 112*a* and 112*b* of the upper cabinet 11. Thus, when the filter mounting members 61*a* and 61*b* and the filter modules 62*a*, 62*b*, 62*c*, and 62*d* are placed at the second position, the filter modules 62*a*, 62*b*, 62*c*, and 62*d* may be disposed to be separated in a forward direction along the lateral parts 112*a* and 112*b* of the upper cabinet 11.

<Regarding Controller>

Figure 36:
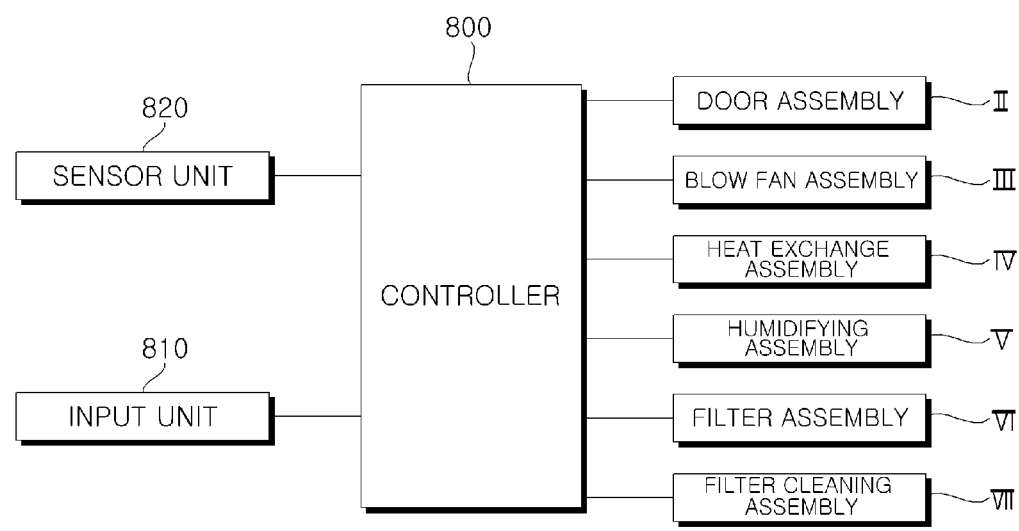
FIG. 36 is a block diagram of a controller and elements relevant thereto according to an embodiment of the present invention.

Hereinafter, with reference to FIG. 36, a controller of an indoor unit for an air conditioner according to an embodiment of the present invention will be described.

An indoor unit for an air conditioner according to the present embodiment may include: an input unit 810 configured to receive a control command (e.g., from a user); a sensor unit 820 configured to receive a variety of information relating to the air conditioner; and a controller 800 configured to control overall operations of the air conditioner.

The controller 800 may control operations of a door assembly II, a blow fan assembly III, a heat exchange assembly IV, a humidifying assembly V, a filter assembly VI, and a filter cleaning assembly VII.

Specifically, the controller 800 may control operation of a door moving member such that a door plate 21 moves to the left or to the right, or may move a cover moving member such that a front discharge port cover 23 opens or closes a front discharge port 22. The controller 800 may control operation of a front blow motor 312 rotating a front blow fan 311, or may control operation of lateral blow motors 322*a*, 322*b*, and 322*c* rotating lateral blow fans 321*a*, 321*b*, and 321*c*.

The controller 800 may control operation of an expansion valve (not shown) that adjusts an amount or pressure of refrigerant flowing into a heat exchanger. The controller 800 may control operation of a heating unit 52 that receives water from a water tank 52 and heats the water. The controller 800 may control operation of a filter cleaner 71 that moves along a guide rail 116.

The controller 800 may control operation of driving devices 633*a*, 633*b*, 633*a'*, and 633*b'* that press mobile members 631*a*, 631*b*, 632*a*, and 632*b*. When a control command is received to change positions of the filter mounting members 61*a* and 61*b*, the controller 800 may control operation of the driving devices 633*a*, 633*b*, 633*a'*, and 633*b'* that press the mobile members 631*a*, 631*b*, 632*a*, and 632*b*.

When the input unit 810 receives a control command to change the positions of the filter mounting members 61*a* and 61*b*, the controller 800 may control operation of the driving devices 633*a*, 633*b*, 633*a'*, and 633*b'* that press the mobile members 631*a*, 631*b*, 632*a*, and 632*b*. When the input unit 810 receives from a user a control command to change the positions of the filter mounting members 61*a* and 61*b*, the input unit 810 transmits a control command to the controller to change the positions of the filter mounting members 61*a* and 61*b*. When the controller 800 receives from the input unit 810 the control signal to change the positions of the filter mounting members 61*a* and 61*b*, the controller may control operation of the driving devices 633*a*, 633*b*, 633*a'*, and 633*b'* that press the mobile members 631*a*, 631*b*, 632*a*, and 632*b*.

The input unit 810 according to an embodiment of the present invention may include a press or touch button device configured to receive a control command in response to pressure by the user; a touch sensor configured to receive a control command based on the user's touch; a microphone sensor configured to receive a control command based on the user's voice; or a camera sensor configured to receive a control command in response to detection of the user's motion. When the controller 800 receives from the sensor unit 820 a control command to change the positions of the filter mounting members 61*a* and 61*b*, the controller 800 may control operation of the driving devices 633*a*, 633*b*, 633*a'*, and 633*b'* that press the mobile members 631*a*, 631*b*, 632*a*, and 632*b*.

The sensor unit 820 may include a filter module detection sensor (not shown) configured to detect an amount of dust contained in the filter modules 62*a*, 62*b*, 62*c*, and 62*d*. According to one embodiment, the filter module detection sensor may include one or more light emitting device and one or more light receiving devices, and may measure an amount of dust stuck in a filter module based on an amount of reflected light which corresponds to a light which is output from a light emitting device, reflected by a floor, and received by a light receiving device. According to another embodiment, the filter module detection sensor may be a sensor that is disposed in the filter modules 62a, 62b, 62c, or 62d to measure an air velocity. Accordingly, the filter module detection sensor may detect an amount of dust stuck in the filter modules 62a, 62b, 62c, and 62d by determining a velocity of air having passed the filter modules 62a, 62b, 62c, and 62d. When it is determined that an amount of dust stuck in the filter modules 62a, 62b, 62c, and 62d is equal to or greater than a threshold, the sensor unit 820 may transmit a control signal to the controller 800 to change the positions of the filter mounting members 61a and 61b. When the controller 800 receives from the sensor unit 820 the control signal to change the positions of the filter mounting members 61a and 61b, the controller 800 may control operation of the driving devices 633a, 633b, 633a', and 633b' that press the mobile members 631a, 631b, 632a, and 632b.

While the present invention has been particularly shown and described with reference to exemplary embodiments thereof, it is understood that the same is by way of illustration and example only and is not to be taken in conjunction with the present invention. It will be understood by those skilled in the art that various changes in form and details may be made therein without departing from the subject matter and scope of the present invention.

What is claimed is:

1. An indoor unit for an air conditioner, comprising:
a cabinet assembly forming an external appearance of the indoor unit and having a suction port formed at a rear surface thereof;
a filter module movably disposed at a rear side of the cabinet assembly, the filter module configured to filter foreign substances in air flowing into the suction port;
a filter mounting member, to which the filter module is mounted; and
a mobile member connected to the filter mounting member to move a position of the filter mounting member,
wherein the mobile member positions the filter mounting member such that a direction of drawing the filter module is forward.

2. The indoor unit of claim 1, further comprising:
a driving device configured to press against the mobile member to change the position of the filter mounting member;
a controller configured to, in response to receiving a control command to change the position of the filter mounting member, operate the driving device to press the mobile member to change the position of the filter mounting member; and
an input unit configured to receive a control command to change the position of the filter mounting member and transmit the control command to the controller,
wherein upon receiving the control command, the controller is configured to operate the driving device that presses the mobile member to change the position of the filter mounting member.

3. The indoor unit of claim 1,
wherein the filter module is configured to be inserted into or drawn from the filter mounting member in a lateral direction of the filter module, and
wherein the filter mounting member is moveable between a first position and a second position, the first position being at which the filter module is positioned at the suction port, and the second position being at which the filter module is positioned with the lateral direction thereof facing forward.

4. The indoor unit of claim 1, wherein the mobile member comprises:
a plurality of dual links, each having a different length and rotatably connected to the cabinet assembly and the filter mounting member, respectively.

5. The indoor unit of claim 4, wherein the dual links comprise:
a first link rotatably connected to the cabinet assembly and the filter mounting member, respectively; and
a second link spaced apart from the first link and rotatably connected to the cabinet assembly and the filter mounting member, respectively, and
wherein the first link is longer than the second link.

6. The indoor unit of claim 5, wherein a gap between a first end of the first link that is connected to the filter mounting member and a first end of the second link that is connected to the filter mounting member is greater than a gap between a second end of the first link that is connected to the cabinet assembly and a second end of the second link that is connected to the cabinet assembly.

7. The indoor unit of claim 5, wherein a distance from the second link to a lateral side of the cabinet assembly is less than a distance from the first link to the lateral side of the cabinet assembly.

8. The indoor unit of claim 5, wherein the drive transmission links comprise:
a motor link fixedly connected to the driving device; and
a bending link having a first end rotatably connected to the motor link and a second end rotatably connected to the first link.

9. The indoor unit of claim 8,
wherein the bending link comprises a bending portion vertically bent between a first end and a second end thereof, and
wherein a distance from the bending portion to the first end of the bending link is less than a distance from the bending portion to the second end of the bending link.

10. The indoor unit of claim 1, wherein the filter mounting member comprises:
a filter module mounting part forming a space to accommodate the filter module, and being open rearward; and
a mobile member fastening part disposed above or below the filter module mounting part, the mobile member fastening part forming a space where the mobile member is disposed, and being open forward.

11. The indoor unit of claim 1,
wherein the cabinet assembly further comprises a rearward protruding member that protrudes rearward,
wherein the filter mounting member is in close contact with the rear protruding member when the filter module is positioned at the suction port.

12. The indoor unit of claim 11,
wherein the rearward protruding member comprises a filter module recognition sensor that protrudes in a direction in which the filter mounting member is mounted and configured so that the filter module recognition sensor is pressable by the filter module,
wherein the filter mounting member comprises a filter module recognition hole that is penetrated by the filter module recognition sensor when the filter mounting member is in close contact with the rearward protruding member.

13. The indoor unit of claim 11,
wherein the rearward protruding member comprises an ionization part having an electrode to ionize molecules in air flowing into the suction port, and
wherein the electrode is disposed to protrude rearward vertically to a rear surface on which the suction port is formed.

14. The indoor unit of claim 13, wherein the filter module comprises:
a pre-filter configured to filter large-sized dust in the air flowing into the suction port;
a dust collecting filter unit configured to collect air particles, ionized by the ionization part, to filter the air;
a deodorization filter unit configured to remove odor from the air flowing into the suction port; and
a filter case with the pre-filter being fixed thereto and the dust collecting filter unit and the deodorization filter unit being mounted thereto.

15. The indoor unit of claim 14, further comprising:
a power terminal configured to supply a voltage to the dust collecting filter unit, and a ground terminal configured to provide a ground to the dust collecting filter unit, wherein the power terminal and the ground terminal are each formed in the rearward protruding member in a direction in which the filter mounting member is mounted;
a power terminal hole configured to be penetrated by the power terminal in response to the filter mounting member being in close contact with the rearward protruding member, and a ground terminal hole configured to be penetrated by the ground terminal in response to the filter mounting member being in close contact with the rearward protruding member, wherein the power terminal hole and the ground terminal hole are each formed in the filter mounting member; and
a power receiving terminal configured to supply power to the dust collecting filter unit in response to contact with the power terminal, and a ground receiving terminal configured to provide a ground to the dust collecting filter unit in response to contact with the ground terminal, wherein the power receiving terminal and the ground receiving terminal are formed in the dust collecting filter unit.

16. An indoor unit for an air conditioner, comprising:
a cabinet assembly having a suction port formed at a rear surface thereof;
a filter module movably disposed at a rear side of the cabinet assembly, the filter module configured to filter foreign substances in air flowing into the suction port;
a filter mounting member to which the filter module is mounted; and
a mobile member connected to the filter mounting member to move a position of the filter mounting member;
wherein the filter module is configured to be inserted into or drawn from the filter mounting member in a lateral direction of the filter module, and
wherein the filter mounting member is moveable between a first position and a second position, the first position being at which the filter module is positioned at the suction port, and the second position being at which the filter module is positioned with the lateral direction thereof facing forward.

17. The indoor unit of claim 16, wherein the filter mounting member comprises:
a filter module mounting part forming a space to accommodate the filter module, and being open rearward; and
a mobile member fastening part disposed above or below the filter module mounting part, the mobile member fastening part forming a space where the mobile member is disposed, and being open forward.

18. The indoor unit of claim 17, wherein the cabinet assembly further comprises a rearward protruding member that protrudes rearward,
wherein the filter mounting member is in close contact with the rear protruding member when the filter module is positioned at the suction port,
wherein the rearward protruding member comprises a filter module recognition sensor that protrudes in a direction in which the filter mounting member is mounted and configured so that the filter module recognition sensor is pressable by the filter module,
wherein the filter mounting member comprises a filter module recognition hole that is penetrated by the filter module recognition sensor when the filter mounting member is in close contact with the rearward protruding member.

19. The indoor unit of claim 5, further comprising:
a driving device configured to press against the mobile member to change the position of the filter mounting member,
wherein the mobile member further comprises a plurality of drive transmission links, each transferring forces generated by the driving device to the dual links.

20. The indoor unit of claim 19, wherein a distance from the first link to the driving device is less than a distance from the second link to the driving device.

* * * * *